(12) United States Patent
Kato et al.

(10) Patent No.: US 10,464,895 B2
(45) Date of Patent: Nov. 5, 2019

(54) COMPOUND, MATERIAL FOR ORGANIC ELECTROLUMINESCENCE ELEMENTS, ORGANIC ELECTROLUMINESCENCE ELEMENT, AND ELECTRONIC DEVICE

(71) Applicant: IDEMITSU KOSAN CO., LTD., Chiyoda-ku (JP)

(72) Inventors: Tomoki Kato, Ichihara (JP); Masahiro Kawamura, Chiba (JP); Masakazu Funahashi, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

(21) Appl. No.: 15/765,639

(22) PCT Filed: Oct. 5, 2016

(86) PCT No.: PCT/JP2016/079647
§ 371 (c)(1),
(2) Date: Apr. 3, 2018

(87) PCT Pub. No.: WO2017/061480
PCT Pub. Date: Apr. 13, 2017

(65) Prior Publication Data
US 2019/0077754 A1    Mar. 14, 2019

(30) Foreign Application Priority Data

Oct. 6, 2015  (JP) .................... 2015-198918

(51) Int. Cl.
*H01L 51/50* (2006.01)
*C07D 209/86* (2006.01)
(Continued)

(52) U.S. Cl.
CPC ......... *C07D 209/86* (2013.01); *C07D 209/82* (2013.01); *H01L 51/0059* (2013.01);
(Continued)

(58) Field of Classification Search
None
See application file for complete search history.

(56) References Cited

U.S. PATENT DOCUMENTS 9,196,839 B2 *  11/2015  Yokoyama ............ C07C 211/54
2002/0128514 A1 *  9/2002  Uemura ................. C09K 11/06
564/426
(Continued)

FOREIGN PATENT DOCUMENTS

EP    2 364 980        9/2011
JP    2010-222261 A   10/2010
(Continued)

OTHER PUBLICATIONS

International Search Report dated Nov. 22, 2016 in PCT/JP2016/079647 filed Oct. 5, 2016.
(Continued)

*Primary Examiner* — Benjamin P Sandvik
(74) *Attorney, Agent, or Firm* — Oblon, McClelland, Maier & Neustadt, L.L.P.

(57) ABSTRACT

A compound represented by formula (1) provides an organic electroluminescence device having a high efficiency and a long lifetime:
(Continued)

(56) References Cited

U.S. PATENT DOCUMENTS

| | | | |
|---|---|---|---|
| 2008/0014464 | A1 | 1/2008 | Kawamura et al. |
| 2011/0278551 | A1 | 11/2011 | Yabunouchi et al. |
| 2011/0315964 | A1 | 12/2011 | Eida et al. |
| 2012/0074395 | A1 | 3/2012 | Yabunouchi et al. |
| 2012/0091438 | A1 | 4/2012 | Yabunouchi et al. |
| 2012/0175600 | A1 | 7/2012 | Yabunouchi et al. |
| 2012/0187391 | A1 | 7/2012 | Kato et al. |
| 2012/0292606 | A1 | 11/2012 | Kato |
| 2015/0014645 | A1 | 1/2015 | Park et al. |
| 2015/0255729 | A1 | 9/2015 | Yabunouchi et al. |
| 2016/0020403 | A1 | 1/2016 | Kawamura et al. |
| 2016/0079542 | A1 | 3/2016 | Itoi |
| 2018/0090688 | A1 | 3/2018 | Cha et al. |

FOREIGN PATENT DOCUMENTS

| | | |
|---|---|---|
| JP | 2011-51936 A | 3/2011 |
| JP | 2011-129275 | 6/2011 |
| JP | 2016-58549 A | 4/2016 |
| JP | 2016-58550 A | 4/2016 |
| KR | 10-2013-0106255 A | 9/2013 |
| WO | WO 2007/148660 A1 | 12/2007 |
| WO | WO 2010/061824 A1 | 6/2010 |
| WO | WO 2010/114017 A1 | 10/2010 |
| WO | WO 2010/114021 A1 | 10/2010 |
| WO | WO 2011/024922 A1 | 3/2011 |
| WO | WO 2011/040607 A1 | 4/2011 |
| WO | WO 2015/041416 A1 | 3/2015 |

OTHER PUBLICATIONS

Extended European Search Report dated Jan. 28, 2019, in the corresponding European Patent Application No. 16853634.
Communication pursuant to Rule 114(2) EPC dated Sep. 10, 2019 in European Patent Application No. 16853634.0 filed Oct. 5, 2016 (15 pages).

\* cited by examiner

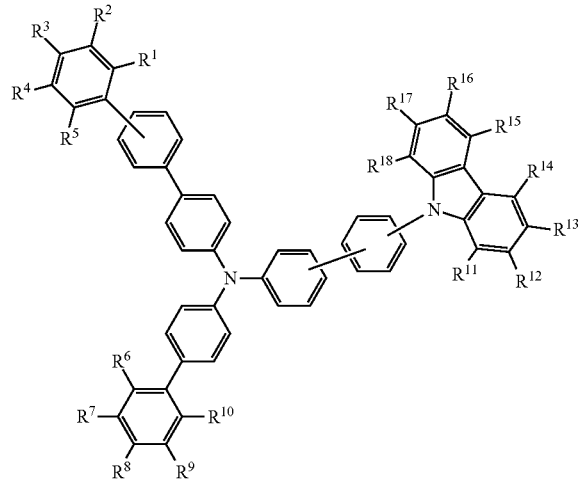

(1)

wherein $R^1$ to $R^5$, $R^6$ to $R^{10}$, and $R^{11}$ to $R^{18}$ are as defined in the description.

16 Claims, 1 Drawing Sheet

(51) Int. Cl.
  *C07D 209/82* (2006.01)
  *H01L 51/00* (2006.01)
  *H01L 51/52* (2006.01)
(52) U.S. Cl.
  CPC .......... *H01L 51/0072* (2013.01); *H01L 51/50* (2013.01); *H01L 51/5016* (2013.01); *H01L 51/5092* (2013.01); *H01L 51/5096* (2013.01); *H01L 51/5206* (2013.01); *H01L 51/5221* (2013.01); *H01L 51/5056* (2013.01); *H01L 51/5072* (2013.01)

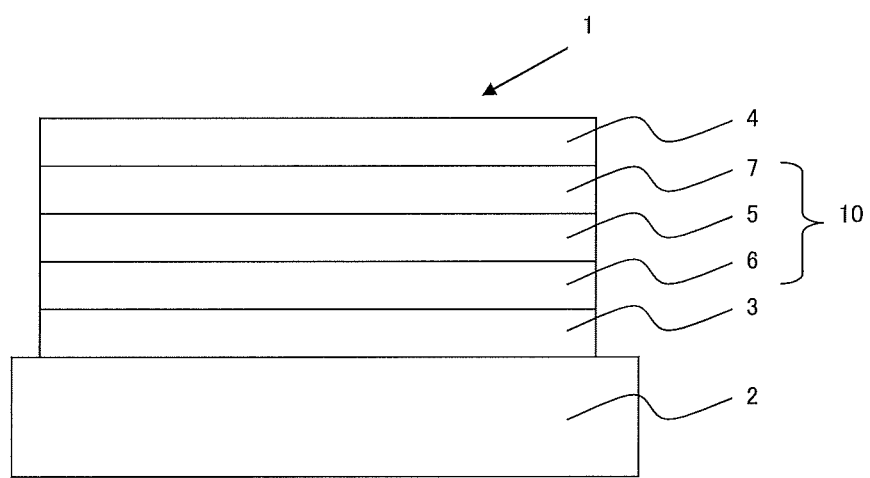

COMPOUND, MATERIAL FOR ORGANIC ELECTROLUMINESCENCE ELEMENTS, ORGANIC ELECTROLUMINESCENCE ELEMENT, AND ELECTRONIC DEVICE

TECHNICAL FIELD

The present invention relates to compounds, materials for organic electroluminescence devices comprising the compounds, organic electroluminescence devices comprising the compounds, and electronic devices comprising the organic electroluminescence devices.

BACKGROUND ART

Organic electroluminescence devices (hereinafter also referred to as "organic EL device") comprising an organic compound are much expected to be useful as inexpensive, large-sized full color display devices of solid state emission type and many developments have been made thereon. An organic EL device is generally constructed from a light emitting layer and a pair of opposite electrodes sandwiching the light emitting layer. When an electric field is applied between the electrodes, electrons are injected from a cathode and holes are injected from an anode into the light emitting layer. The injected electrons recombine with the injected holes in the light emitting layer to form excited states. When the excited state returns to the ground state, the energy is released as light.

Many researches have been made on the applications of organic EL device to display, etc. because of its possibility of a wide selection of emission colors by using various emitting materials in a light emitting layer. Particularly, the research on the materials which emit three primary red, green, and blue colors has been made most actively, and the intensive research has been made to improve their properties.

As such materials for organic electroluminescence devices, Patent Literature 1 discloses a tertiary amine having two p-biphenylyl groups and one p-biphenylyl group having a N-carbazolyl substituent at the p- or m-position of the terminal phenyl group (compounds A-5 and A-20) and a tertiary amine having two p-biphenylyl groups and one m-biphenylyl group having a N-carbazolyl substituent at the p- or m-position of the terminal phenyl group (compounds A-21 and A-22).

Patent Literature 2 discloses a triphenylamine wherein each of three phenyl groups is p-substituted with a phenyl group optionally having a substituent at its o-position, m-position, or both. A specific example thereof is a triphenylamine wherein each of two or three phenyl groups is p-substituted with a m-substituted phenyl group, for example, a tertiary amine (1-21) wherein three phenyl groups of a triphenylamine are p-substituted with a m-phenylphenyl group, a m-(1-naphthyl)phenyl group, and a m-(N-carbazolyl)phenyl group; a tertiary amine (1-22) wherein three phenyl groups of a triphenylamine are p-substituted with an unsubstituted phenyl group, a m-(1-naphthyl)phenyl group, and a m-(N-carbazolyl)phenyl group; and a tertiary amine (1-23) wherein three phenyl groups of a triphenylamine are p-substituted with a m-(3-biphenylyl)phenyl group, a m-(1-naphthyl)phenyl group, a m-(N-carbazolyl)phenyl group.

Patent Literature 3 discloses a tertiary amine which essentially has a terphenylyl group and an aryl group having a N-carbazolyl substituent or a C-carbazolyl substituent. The tertiary amine has preferably two terphenylyl groups (paragraph [0045]). As the specific examples thereof, a tertiary amine having two p-terphenylyl groups and one p-(N-carbazolyl)phenyl group; a tertiary amine having two p-terphenylyl groups and one p-(N-carbazolyl)-3-biphenylyl group; and a tertiary amine having a p-terphenylyl group, a 3-(m-terphenylyl) group, and a p-(N-carbazolyl)-3-biphenylyl group are disclosed (paragraph [0059]).

Patent Literature 4 discloses a tertiary amine which has essentially one or two m-(N-carbazolyl)phenyl groups, for example, the tertiary amine A-4 having a p-terphenylyl group, a p-biphenylyl group, and a m-(N-carbazolyl)phenyl group.

Patent Literature 5 discloses a tertiary amine having a N-carbazolyl group, for example, the compounds 4 and 16, etc.

CITATION LIST

Patent Literature

Patent Literature 1: WO 2007/148660
Patent Literature 2: WO 2011/024922
Patent Literature 3: WO 2010/114021
Patent Literature 4: JP 2010-222261A
Patent Literature 5: US 2016/0079542A1

SUMMARY OF INVENTION

Technical Problem

To further improve the performance of organic EL devices, it has been required to develop a new material useful for use in organic EL devices. Thus, an object of the invention is to provide organic EL devices which are operated at a low driving voltage and have a high efficiency and a long lifetime and provide compounds which realize such organic EL devices.

Solution to Problem

As a result of extensive research in view of achieving the above object, the inventors have found that a compound represented by formula (1) provides organic EL devices which are operated at a low driving voltage and have a high efficiency and a long lifetime In an aspect of the invention, the following (1) to (4) are provided:
(1) a compound represented by formula (1):

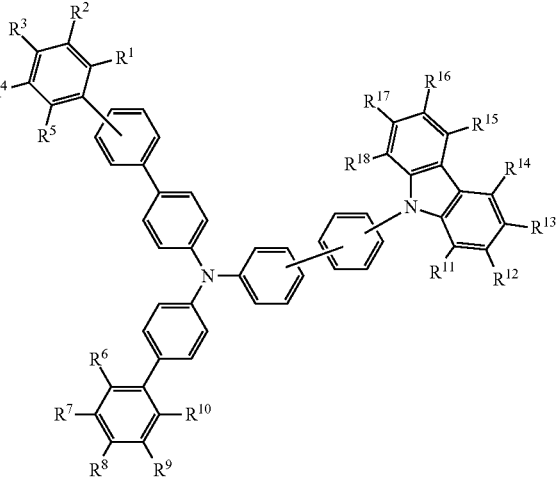

(1)

wherein:

each of $R^1$ to $R^5$ is independently a hydrogen atom, a substituted or unsubstituted alkyl group having 1 to 20 carbon atoms, a substituted or unsubstituted aryl group having 6 to 30 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 30 ring carbon atoms, a halogen atom, or a cyano group, and adjacent two selected from $R^1$ to $R^5$ are not bonded to each other thereby failing to form a ring structure;

each of $R^6$ to $R^{10}$ is independently a hydrogen atom, a substituted or unsubstituted alkyl group having 1 to 20 carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 30 ring carbon atoms, a halogen atom, or a cyano group, or adjacent two selected from $R^6$ to $R^{10}$ form a ring structure by being bonded to each other or do not form a ring structure; and each of $R^{11}$ to $R^{18}$ is independently a hydrogen atom, a substituted or unsubstituted alkyl group having 1 to 20 carbon atoms, a substituted or unsubstituted aryl group having 6 to 30 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 30 ring carbon atoms, a halogen atom, or a cyano group, or adjacent two selected from $R^{11}$ to $R^{18}$ form a ring structure by being bonded to each other or do not form a ring structure;

(2) A material for organic electroluminescence devices which comprises the compound described in (1);

(3) An organic electroluminescence device comprising a cathode, an anode, and an organic thin film layer between the cathode and the anode, wherein the organic thin film layer comprises one or more layers, the organic thin film layer comprises a light emitting layer, and at least one layer of the organic thin film layer comprises the compound described in (1); and (4) An electronic device comprising the organic electroluminescence device described in (3).

Advantageous Effects of Invention

Organic EL devices which are operated at a low driving voltage and have a high efficiency and a long lifetime are obtained by using the compounds of the present invention as a material for organic EL devices.

BRIEF DESCRIPTION OF DRAWINGS

FIG. 1 is a schematic view showing the structure of an organic EL device in an aspect of the invention.

DESCRIPTION OF EMBODIMENTS

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The term of "unsubstituted group ZZ" referred to by "substituted or unsubstituted group ZZ" used herein means that no hydrogen atom in the group ZZ is substituted by a substituent.

The definition of "hydrogen atom" used herein includes isotopes different in the neutron numbers, i.e., light hydrogen (protium), heavy hydrogen (deuterium), and tritium.

The number of "ring carbon atoms" referred to herein means, unless otherwise noted, the number of the carbon atoms included in the atoms which are members forming the ring itself of a compound in which a series of atoms is bonded to form a ring (for example, a monocyclic compound, a fused ring compound, a cross-linked compound, a carbocyclic compound, and a heterocyclic compound). If the ring has a substituent, the carbon atom in the substituent is not included in the ring carbon atom. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means, unless otherwise noted, the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The optional substituent referred to by "substituted or unsubstituted" used herein is, for example, at least one selected from the group consisting of an alkyl group having 1 to 20, preferably 1 to 5, and more preferably 1 to 4 carbon atoms; an aryl group having 6 to 30, preferably 6 to 18, and more preferably 6 to 10 ring carbon atoms; a haloalkyl group having 1 to 20, preferably 1 to 5, and more preferably 1 to 4 carbon atoms; an alkoxy group having 1 to 20, preferably 1 to 5, and more preferably 1 to 4 carbon atoms; a haloalkoxy group having 1 to 20, preferably 1 to 5, and more preferably 1 to 4 carbon atoms; an aryloxy group having 6 to 30, preferably 6 to 18, and more preferably 6 to 10 ring carbon atoms; a halogen atom, and a cyano group. The optional substituent may be a group other than those mentioned above, as long as the advantageous effect of the invention is obtained.

The details of the optional groups mentioned above are described below with respect to $R^1$ to $R^5$.

In the present invention, examples, preferred examples, etc. described with respect to a group may be combined with examples, preferred examples, etc. described with respect to any of other groups. A specific group selected from examples, preferred examples, etc. described with respect to a group may be combined with another specific group selected from examples, preferred examples, etc. described with respect to any of other groups.

The same also applies to the number of atoms, the number of carbon atoms, and other features. In addition, the same also applies to any of the combinations between the groups, the number of atoms, the number of carbon atoms, and other features.

The compound in an aspect of the invention is represented by formula (1) (hereinafter also referred to as "compound (1)"):

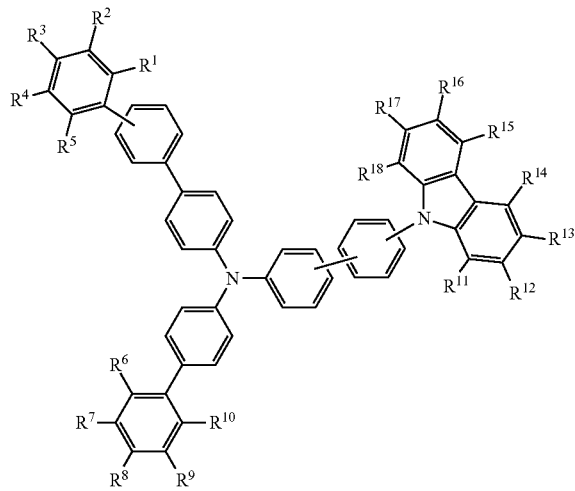

(1)

wherein:

each of $R^1$ to $R^5$ is independently a hydrogen atom, a substituted or unsubstituted alkyl group having 1 to 20 carbon atoms, a substituted or unsubstituted aryl group having 6 to 30 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 30 ring carbon atoms, a halogen atom, or a cyano group, and adjacent two selected from $R^1$ to $R^5$ are not bonded to each other thereby failing to form a ring structure;

each of $R^6$ to $R^{10}$ is independently a hydrogen atom, a substituted or unsubstituted alkyl group having 1 to 20 carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 30 ring carbon atoms, a halogen atom, or a cyano group, or adjacent two selected from $R^6$ to $R^{10}$ form a ring structure by being bonded to each other or do not form a ring structure; and each of $R^{11}$ to $R^{18}$ is independently a hydrogen atom, a substituted or unsubstituted alkyl group having 1 to 20 carbon atoms, a substituted or unsubstituted aryl group having 6 to 30 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 30 ring carbon atoms, a halogen atom, or a cyano group, or adjacent two selected from $R^{11}$ to $R^{18}$ form a ring structure by being bonded to each other or do not form a ring structure.

As seen from formula (1), the compound (1) is a tri(biphenylyl)amine compound, wherein the first biphenylyl group has a terminal benzene ring which optionally has a substituent, the second biphenylyl group has a terminal benzene ring which has a substituted or unsubstituted phenyl group, and the third biphenylyl group has a terminal benzene ring which has a substituted or unsubstituted N-carbazolyl group. With these three groups on the central nitrogen atom, the advantageous effect of the invention is obtained.

The compound (1) is preferably represented by formula (2):

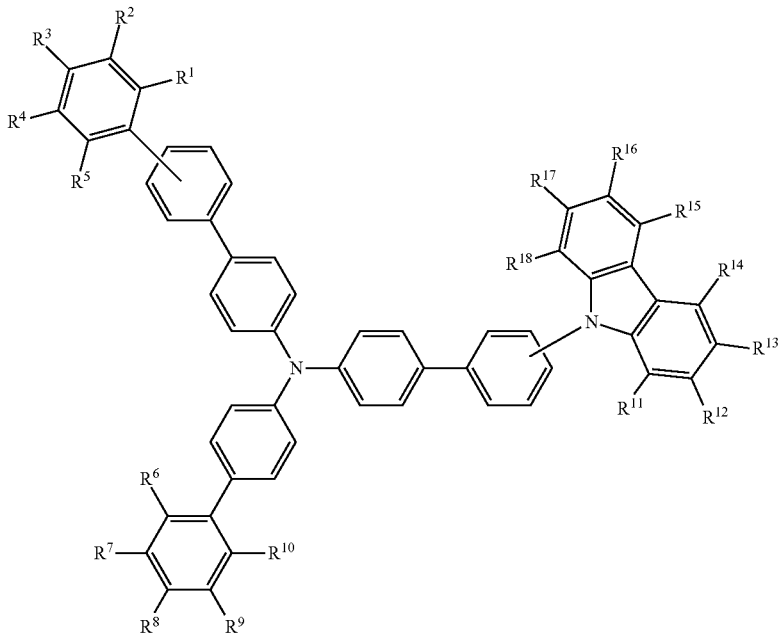

(2)

wherein $R^1$ to $R^5$, $R^6$ to $R^{10}$, and $R^{11}$ to $R^{18}$ are as defined above.
The compound (1) is preferably represented by any of formulae (3) to (5):
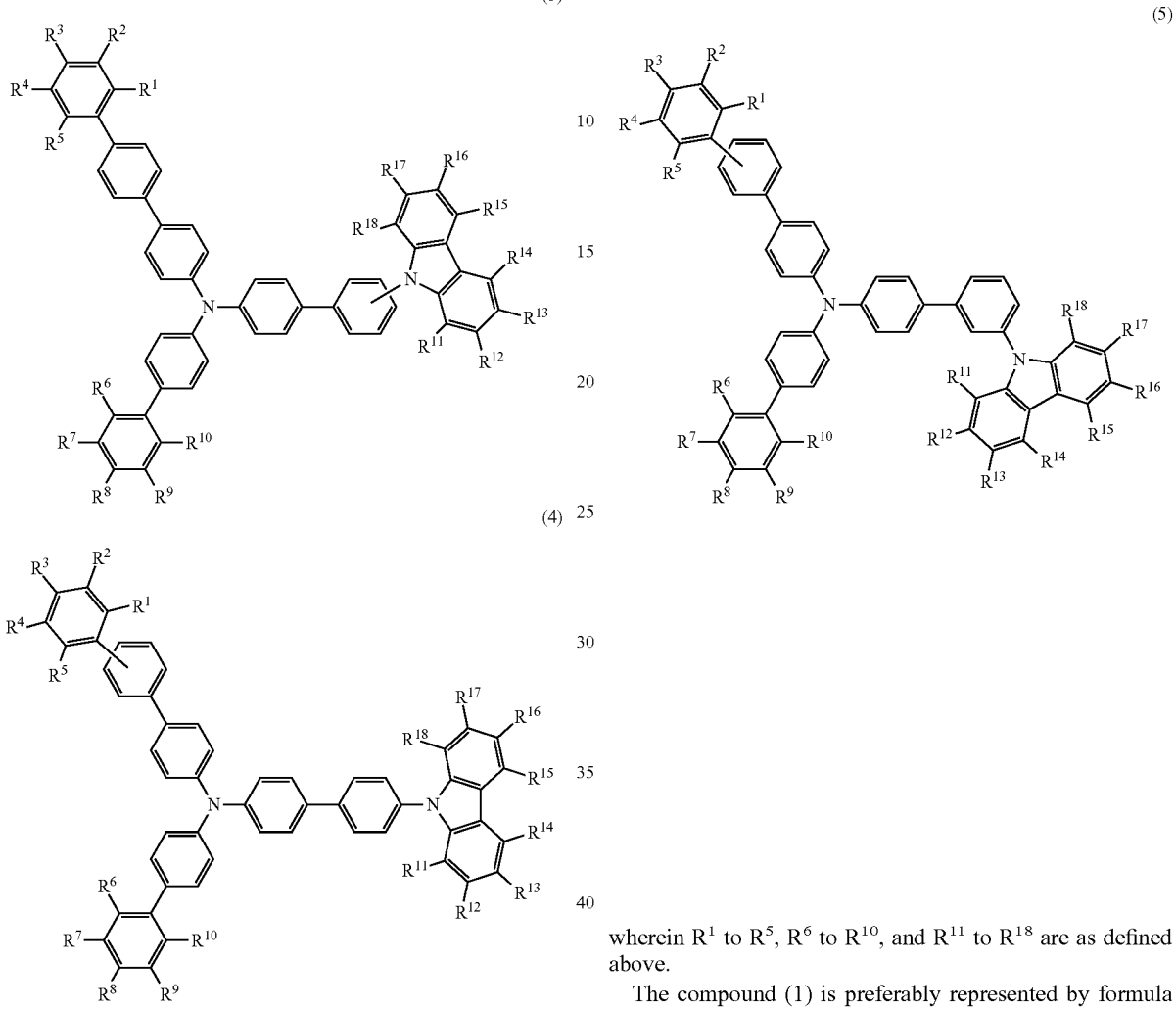
wherein $R^1$ to $R^5$, $R^6$ to $R^{10}$, and $R^{11}$ to $R^{18}$ are as defined above.
The compound (1) is preferably represented by formula (6):
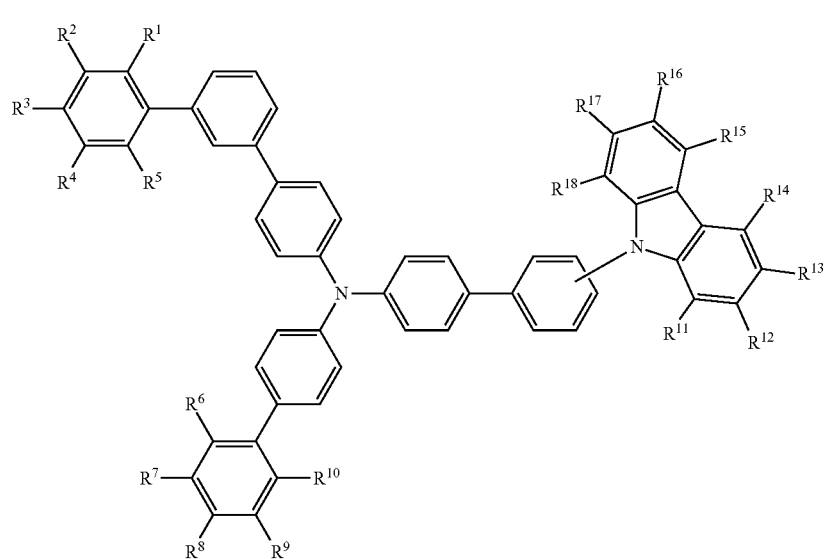

wherein $R^1$ to $R^5$, $R^6$ to $R^{10}$, and $R^{11}$ to $R^{18}$ are as defined above.
The compound (1) is preferably represented by formula (7) or (8):
(7)
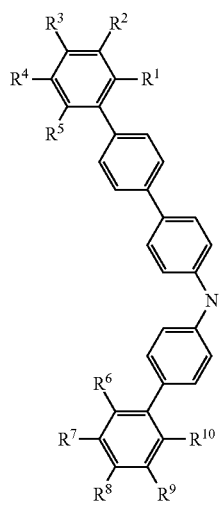
(8)
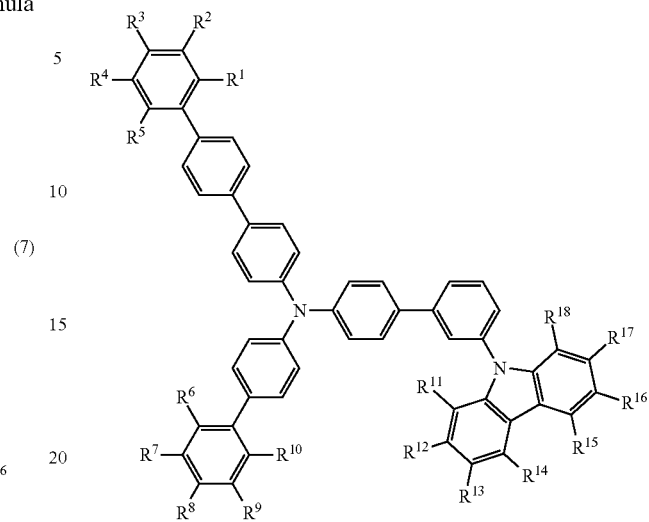
wherein $R^1$ to $R^5$, $R^6$ to $R^{10}$, and $R^{11}$ to $R^{18}$ are as defined above.
The compound (1) is preferably represented by formula (9) or (10):
(9)
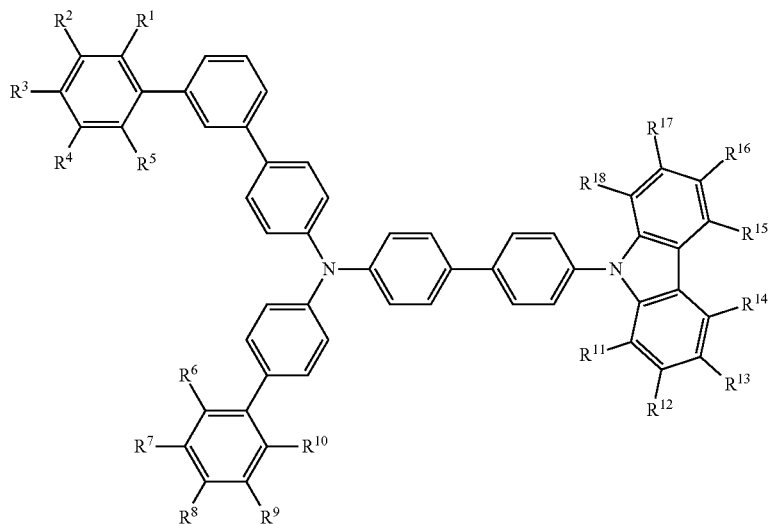

-continued (10)

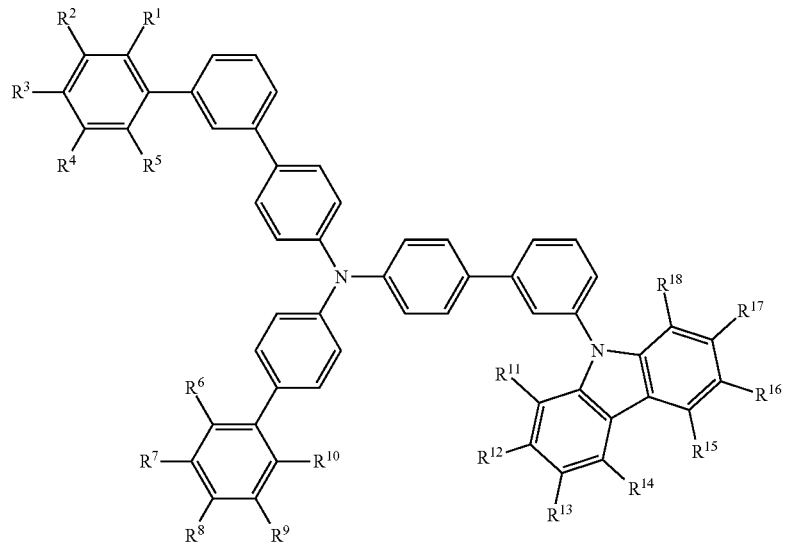

wherein $R^1$ to $R^5$, $R^6$ to $R^{10}$, and $R^{11}$ to $R^{18}$ are as defined above.

$R^1$ to $R^5$, $R^6$ to $R^{10}$, and $R^{11}$ to $R^{18}$ in formulae (1) to (10) will be described below in more detail.

Each of $R^1$ to $R^5$ is independently a hydrogen atom, a substituted or unsubstituted alkyl group having 1 to 20, preferably 1 to 5, and more preferably 1 to 4 carbon atoms, a substituted or unsubstituted aryl group having 6 to 30, preferably 6 to 18, and more preferably 6 to 10 ring carbon atoms, a substituted or unsubstituted haloalkyl group having 1 to 20, preferably 1 to 5, and more preferably 1 to 4 carbon atoms, a substituted or unsubstituted alkoxy group having 1 to 20, preferably 1 to 5, and more preferably 1 to 4 carbon atoms, a substituted or unsubstituted haloalkoxy group having 1 to 20, preferably 1 to 5, and more preferably 1 to 4 carbon atoms, a substituted or unsubstituted aryloxy group having 6 to 30, preferably 6 to 18, and more preferably 6 to 10 ring carbon atoms, a halogen atom, or a cyano group.

Preferably, each of $R^1$ to $R^5$ is independently selected from the group consisting of a hydrogen atom, the alkyl group having 1 to 20 carbon atoms, the aryl group having 6 to 30 ring carbon atoms, the haloalkyl group having 1 to 20 carbon atoms, and a halogen atom. $R^1$ to $R^5$ may be all hydrogen atoms.

Examples of the alkyl group having 1 to 20 carbon atoms of the substituted or unsubstituted alkyl group having 1 to 20 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups). Preferred are a methyl group, an ethyl group, a n-propyl group, an isopropyl group, a n-butyl group, an isobutyl group, a s-butyl group, a t-butyl group, and a pentyl group (inclusive of isomeric groups), with a methyl group, an ethyl group, a n-propyl group, an isopropyl group, a n-butyl group, an isobutyl group, a s-butyl group, and a t-butyl group being more preferred, and a methyl group and a t-butyl group being still more preferred.

Examples of the aryl group having 6 to 30 ring carbon atoms of the substituted or unsubstituted aryl group having 6 to 30 ring carbon atoms include a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a triphenylenyl group, a phenalenyl group, a fluorenyl group, a pyrenyl group, a chrysenyl group, a benzochrysenyl group, a s-indacenyl group, an as-indacenyl group, a fluoranthenyl group, a pentacenyl group, a picenyl group, and a pentaphenyl group. Preferred are a phenyl group, a 1-naphthyl group, a 2-naphthyl group, a biphenylyl group, such as a 2-, 3- or 4-biphenylyl group, and a terphenylyl group, such as a 2-p-terphenylyl group, a 4-p-terphenylyl group, a 2'-m-terphenylyl group, or a 5'-m-terphenylyl group, with a phenyl group, a 1-naphthyl group, and a 2-naphthyl group being more preferred, and a phenyl group being still more preferred.

Examples of the substituted aryl group having 6 to 30 ring carbon atoms include a dimethylfluorenyl group and a 9,9-diphenylfluorenyl group.

The haloalkyl group having 1 to 20 carbon atoms of the substituted or unsubstituted haloalkyl group having 1 to 20 carbon atoms is derived from the alkyl group having 1 to 20 carbon atoms mentioned above, for example, by by replacing at least one hydrogen atom, preferably 1 to 7 hydrogen atoms, or all the hydrogen atoms with a halogen atom selected from the group consisting of a fluorine atom, a chlorine atom, a bromine atom, and an iodine atom, preferably a fluorine atom. Preferred is a fluoroalkyl group having 1 to 20 carbon atoms, with a heptafluoropropyl group (inclusive of isomeric groups), a pentafluoroethyl group, a 2,2,2-trifluoroethyl group, and a trifluoromethyl group being more preferred, a pentafluoroethyl group, a 2,2,2-trifluoroethyl group, and a trifluoromethyl group being still more preferred, and a trifluoromethyl group being particularly preferred.

The substituted or unsubstituted alkoxy group having 1 to 20 carbon atoms is represented by —OR$^a$, wherein R$^a$ is the substituted or unsubstituted alkyl group having 1 to 20 carbon atoms mentioned above. The alkoxy group having 1 to 20 carbon atoms is preferably a t-butoxy group, a propoxy group (inclusive of isomeric groups), an ethoxy group, or a methoxy group, more preferably an ethoxy group or a methoxy group, and still more preferably a methoxy group.

The substituted or unsubstituted haloalkoxy group having 1 to 20 carbon atoms is represented by —OR$^b$, wherein R$^b$ is the substituted or unsubstituted haloalkyl group having 1 to 20 carbon atoms and preferably a substituted or unsubstituted fluoroalkyl group having 1 to 20 carbon atoms. The haloalkoxy group having 1 to 20 carbon atoms is preferably a fluoroalkoxy group, more preferably a heptafluoropropoxy group (inclusive of isomeric groups), a pentafluoroethoxy group, a 2,2,2-trifluoroethoxy group, or a trifluoromethoxy group, still more preferably a pentafluoroethoxy group, a 2,2,2-trifluoroethoxy group, or a trifluoromethoxy group, and particularly preferably a trifluoromethoxy group.

The substituted or unsubstituted aryloxy group having 6 to 30 ring carbon atoms is represented by —OR$^c$, wherein R$^c$ is the substituted or unsubstituted aryl group having 6 to 30 ring carbon atoms mentioned above. Examples of the aryl group having 6 to 30 ring carbon atoms include a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a triphenylenyl group, a phenalenyl group, a fluorenyl group, a pyrenyl group, a chrysenyl group, a benzochrysenyl group, a s-indacenyl group, an as-indacenyl group, a fluoranthenyl group, a pentacenyl group, a picenyl group, and a pentaphenyl group. Preferred are a phenyl group, a 1-naphthyl group, a 2-naphthyl group, a biphenylyl group, such as a 2-, 3- or 4-biphenylyl group, and a terphenylyl group, such as a 2-p-terphenylyl group, a 4-p-terphenylyl group, a 2'-m-terphenylyl group, and a 5'-m-terphenylyl group, with a phenyl group, a 1-naphthyl group, and a 2-naphthyl group being more preferred, and a phenyl group being still more preferred.

The halogen atom includes a fluorine atom, a chlorine atom, a bromine atom, and an iodine atom, with a fluorine atom being preferred.

Each of R$^6$ to R$^{10}$ is independently, a hydrogen atom, a substituted or unsubstituted alkyl group having 1 to 20, preferably 1 to 5, and more preferably 1 to 4 carbon atoms, a substituted or unsubstituted haloalkyl group having 1 to 20, preferably 1 to 5, and more preferably 1 to 4 carbon atoms, a substituted or unsubstituted alkoxy group having 1 to 20, preferably 1 to 5, and more preferably 1 to 4 carbon atoms, a substituted or unsubstituted haloalkoxy group having 1 to 20, preferably 1 to 5, and more preferably 1 to 4 carbon atoms, a substituted or unsubstituted aryloxy group having 6 to 30, preferably 6 to 18, and more preferably 6 to 10 ring carbon atoms, a halogen atom, or a cyano group.

The details of the above groups are the same as those of the corresponding groups mentioned above with respect to R$^1$ to R$^5$.

Preferably, each of R$^6$ to R$^{10}$ is independently selected from the group consisting of a hydrogen atom, the alkyl group having 1 to 20 carbon atoms, the haloalkyl group having 1 to 20 carbon atoms, and a halogen atom. R$^6$ to R$^{10}$ may be all hydrogen atoms.

Each of R$^{11}$ to R$^{18}$ is independently, a hydrogen atom, a substituted or unsubstituted alkyl group having 1 to 20, preferably 1 to 5, and more preferably 1 to 4 carbon atoms, a substituted or unsubstituted aryl group having 6 to 30, preferably 6 to 18, and more preferably 6 to 10 ring carbon atoms, a substituted or unsubstituted haloalkyl group having 1 to 20, preferably 1 to 5, and more preferably 1 to 4 carbon atoms, a substituted or unsubstituted alkoxy group having 1 to 20, preferably 1 to 5, and more preferably 1 to 4 carbon atoms, a substituted or unsubstituted haloalkoxy group having 1 to 20, preferably 1 to 5, and more preferably 1 to 4 carbon atoms, a substituted or unsubstituted aryloxy group having 6 to 30, preferably 6 to 18, and more preferably 6 to 10 ring carbon atoms, a halogen atom, or a cyano group.

The details of the above groups are the same as those of the corresponding groups mentioned above with respect to R$^1$ to R$^5$.

Preferably, each of R$^{11}$ to R$^{18}$ is independently selected from the group consisting of a hydrogen atom, the alkyl group having 1 to 20 carbon atoms, the aryl group having 6 to 30 ring carbon atoms, the haloalkyl group having 1 to 20 carbon atoms, and a halogen atom. R$^{11}$ to R$^{18}$ may be all hydrogen atoms.

Adjacent two selected from R$^1$ to R$^5$ are not bonded to each other thereby failing to form a ring structure.

Adjacent two selected from R$^6$ to R$^{10}$ and adjacent two selected from R$^{11}$ to R$^{18}$ form a substituted or unsubstituted ring by bonding to each other or do not form a ring. In a preferred embodiment of the invention, none of adjacent two selected from R$^1$ to R$^5$, R$^6$ to R$^{10}$, and R$^{11}$ to R$^{18}$ form a ring.

Examples of the substituted or unsubstituted ring which is formed by the adjacent two and two ring carbon atoms to which the adjacent two are bonded include a substituted or unsubstituted hydrocarbon ring, with a substituted or unsubstituted aromatic hydrocarbon ring being preferred, a substituted or unsubstituted benzene ring being more preferred, and an unsubstituted benzene ring being still more preferred.

One of ordinary skill in the art can easily produce the compound (1) by selecting starting compounds corresponding to an aimed compound and reacting the selected starting compounds with reference to the synthesis examples described below.

Examples of the compound (1) of the invention are shown below, although not limited thereto.

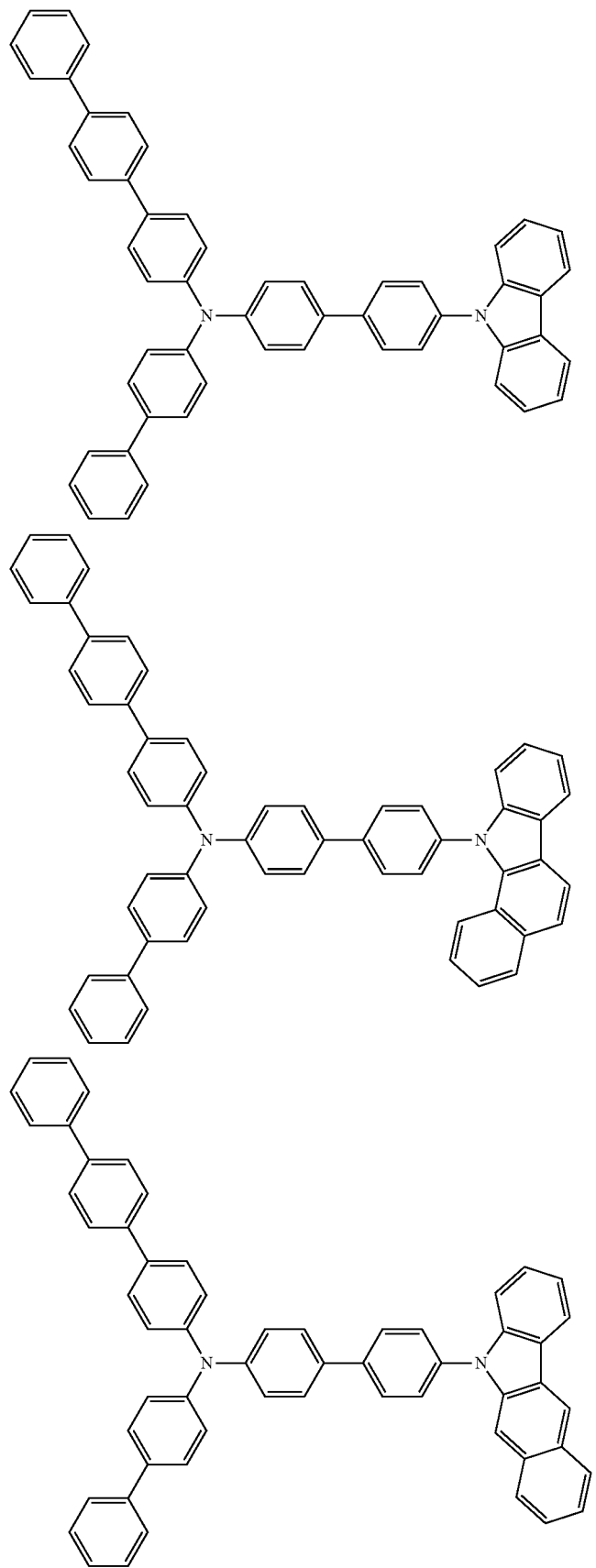

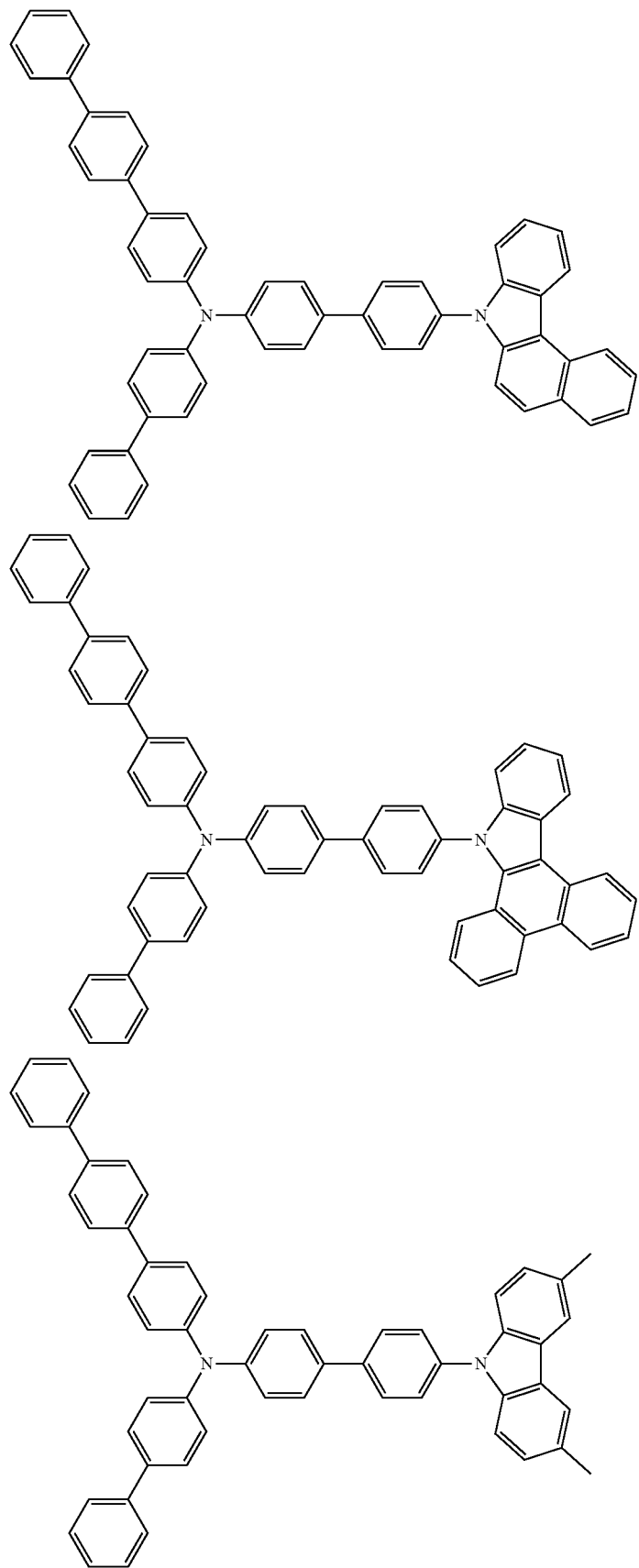

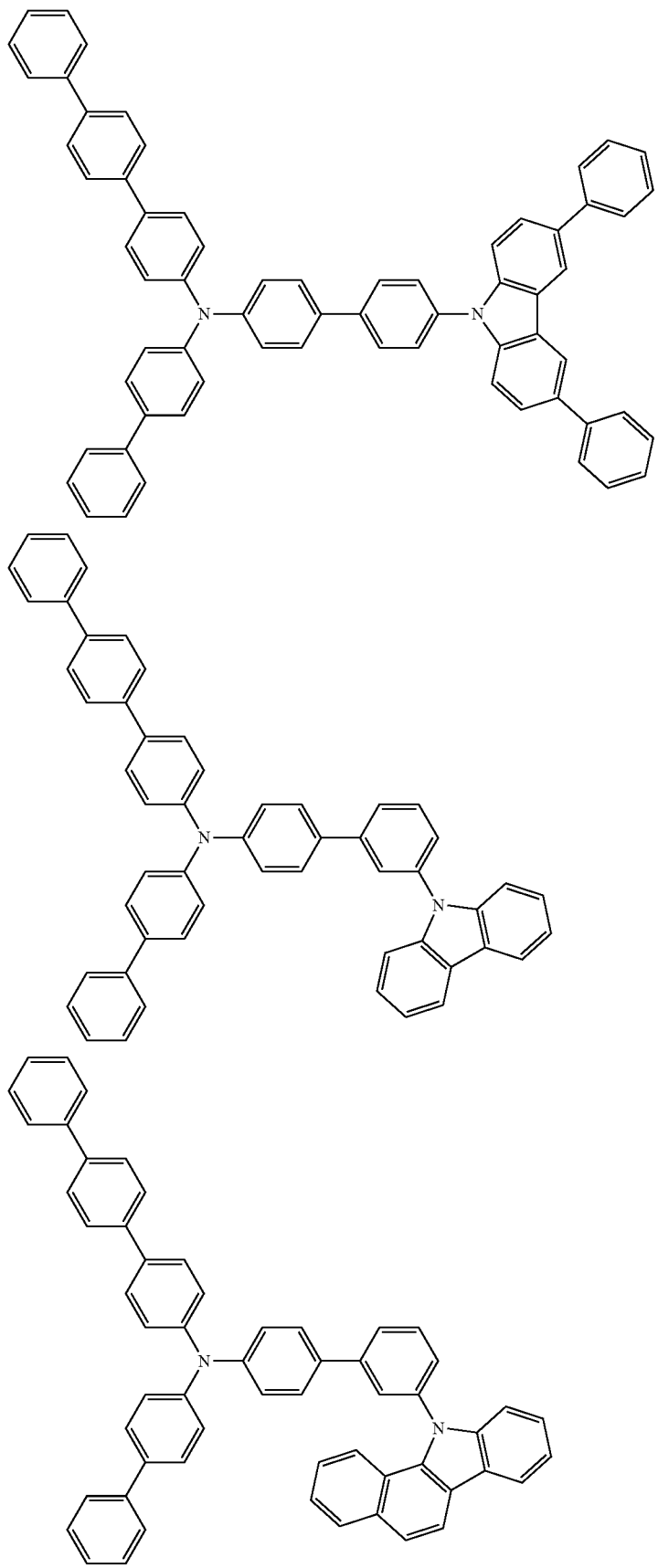

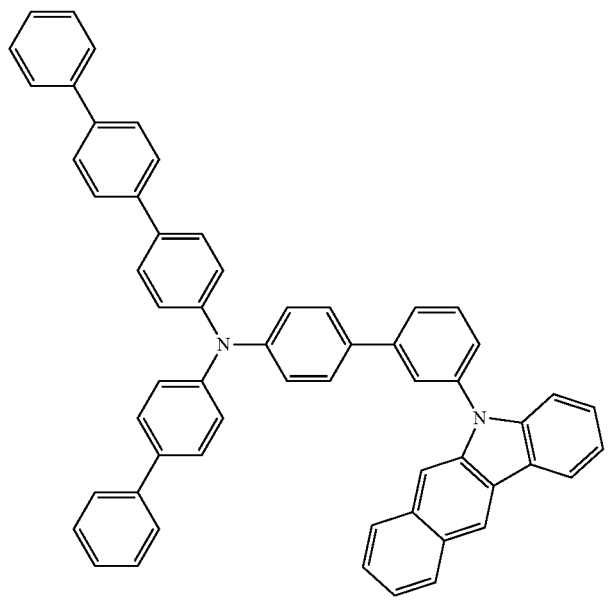
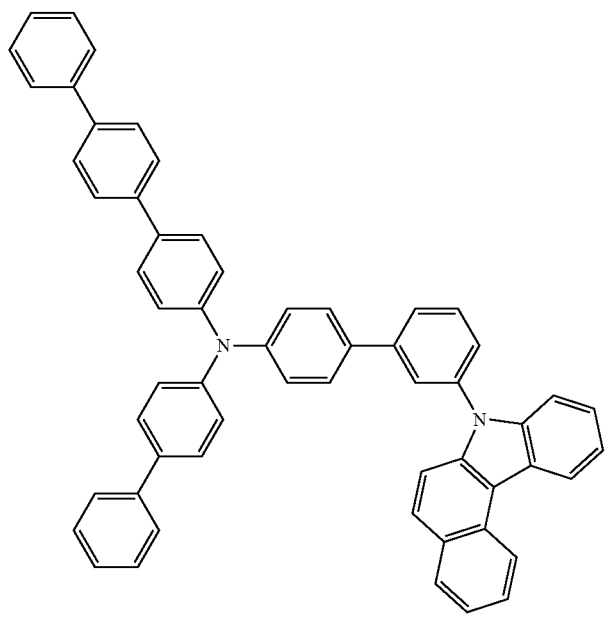

-continued
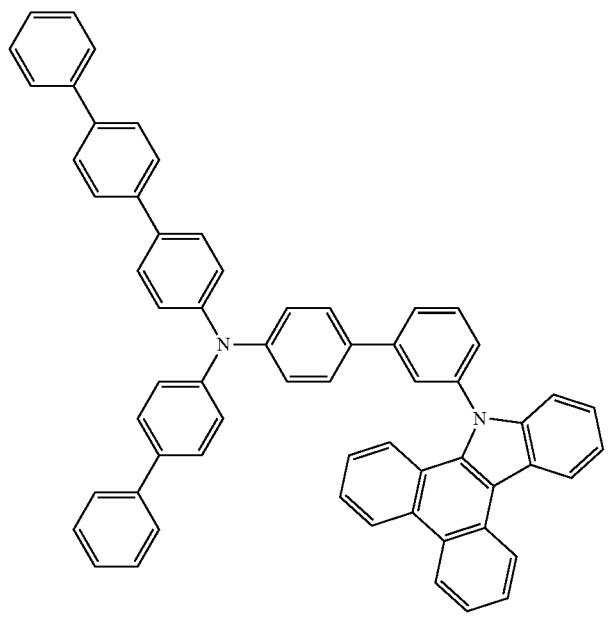
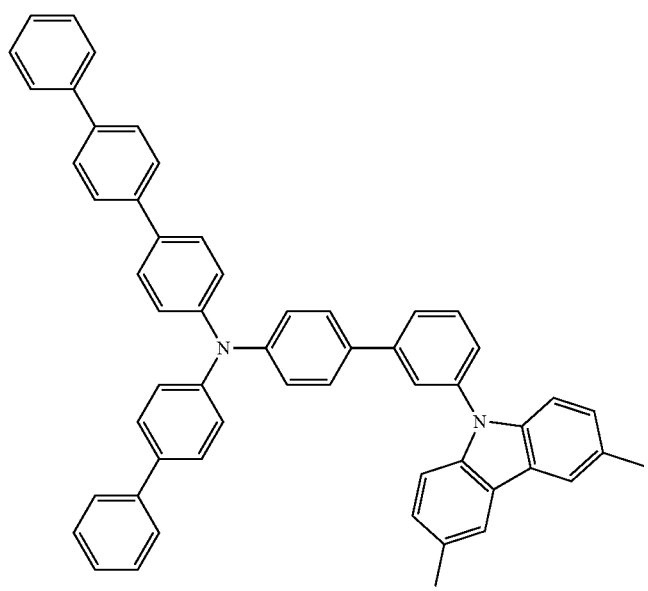

-continued
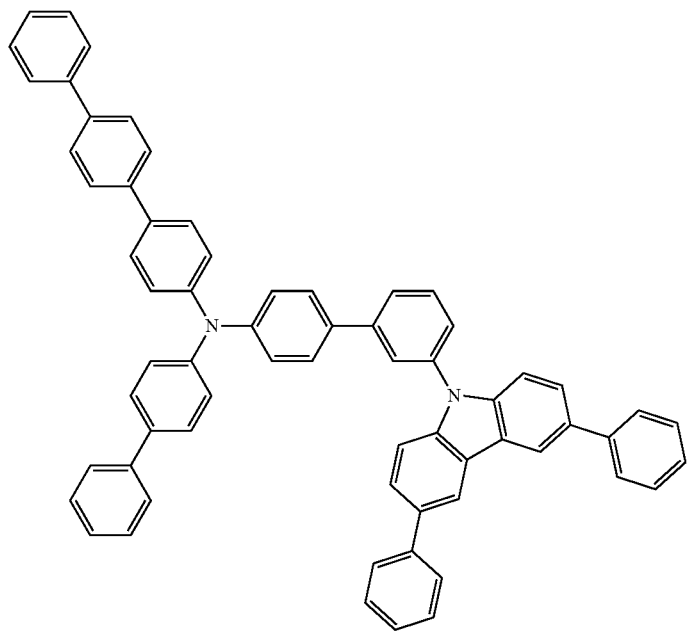
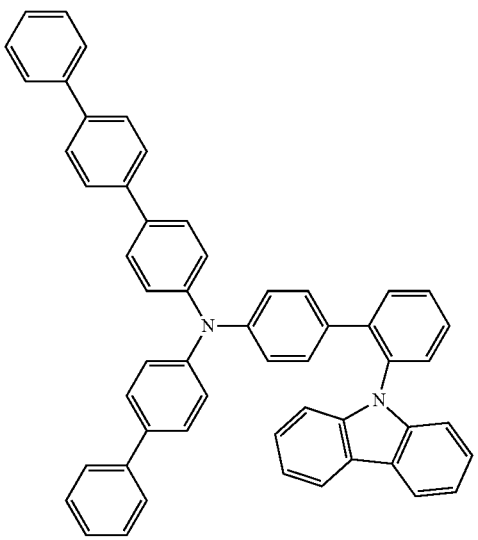
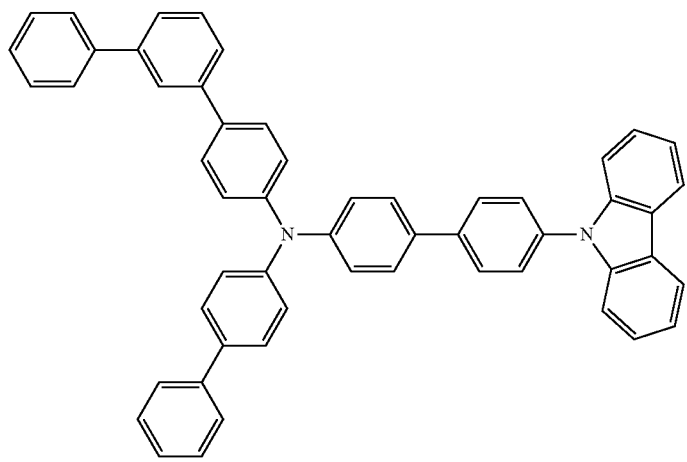
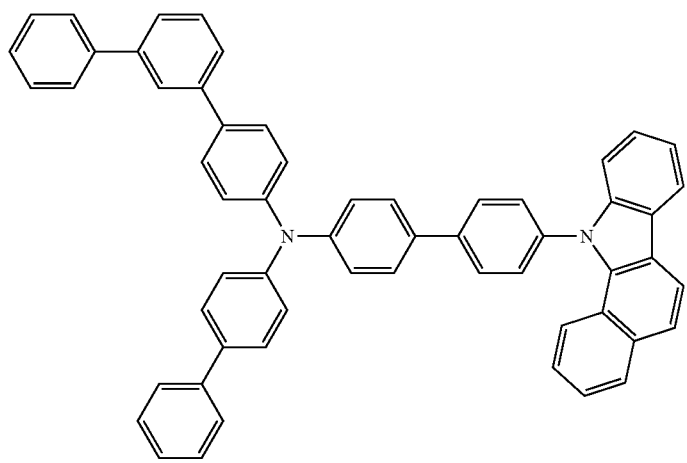

-continued
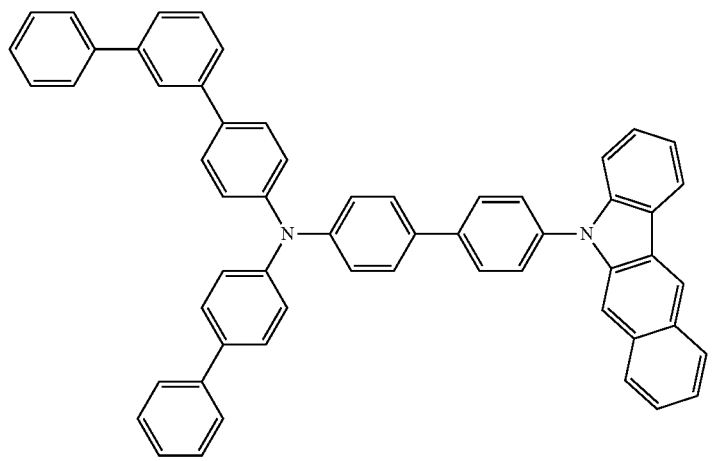
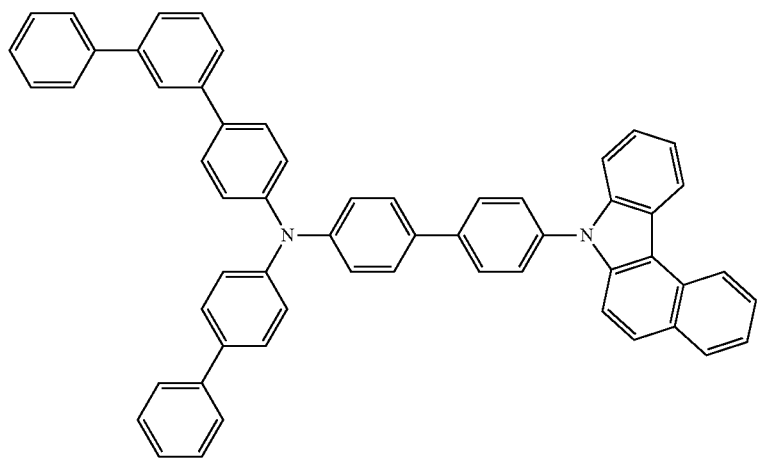
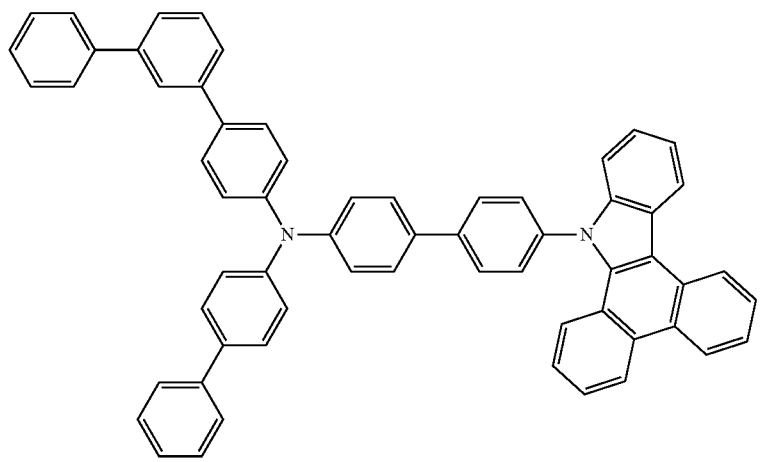

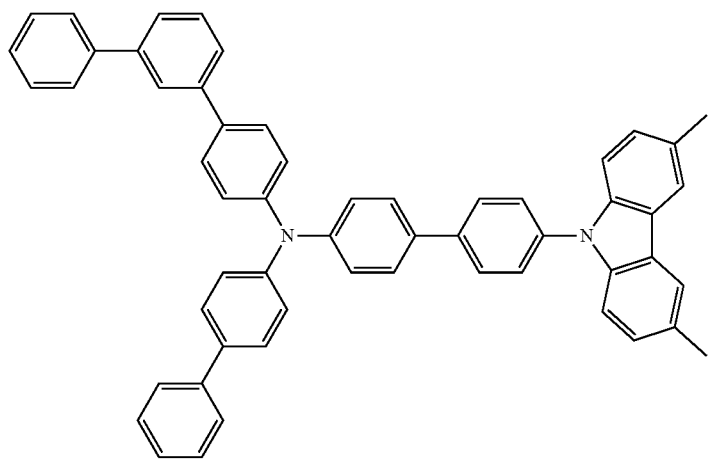
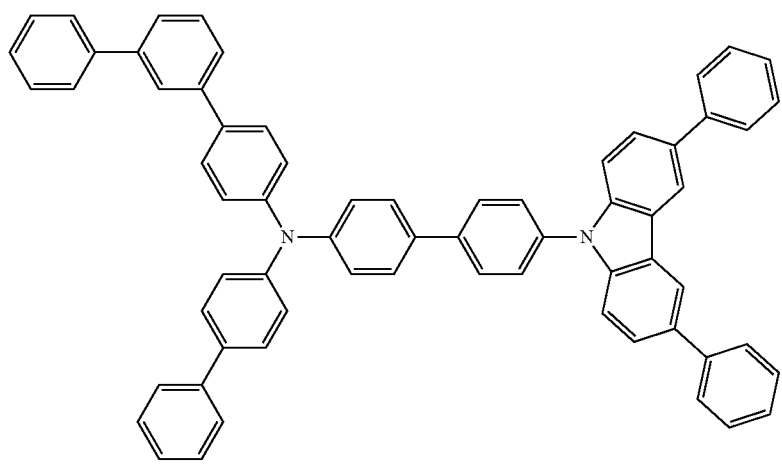
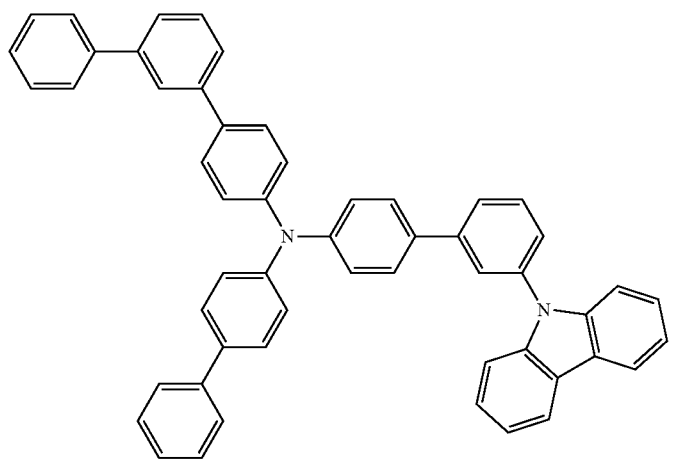

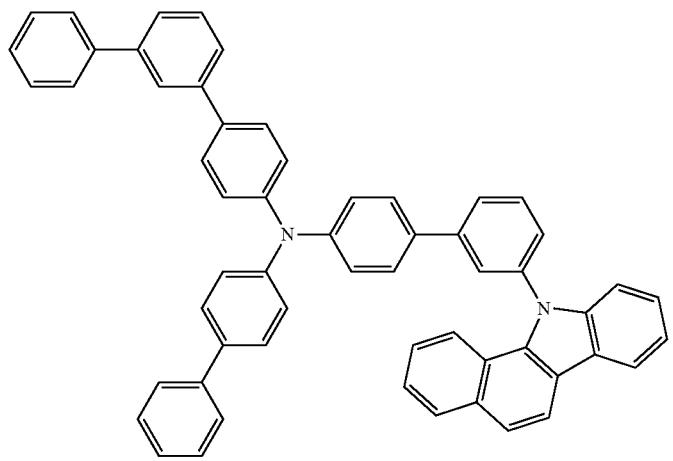
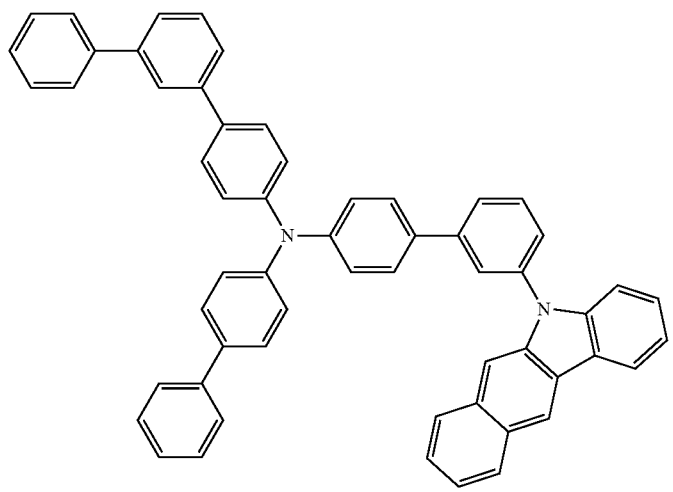
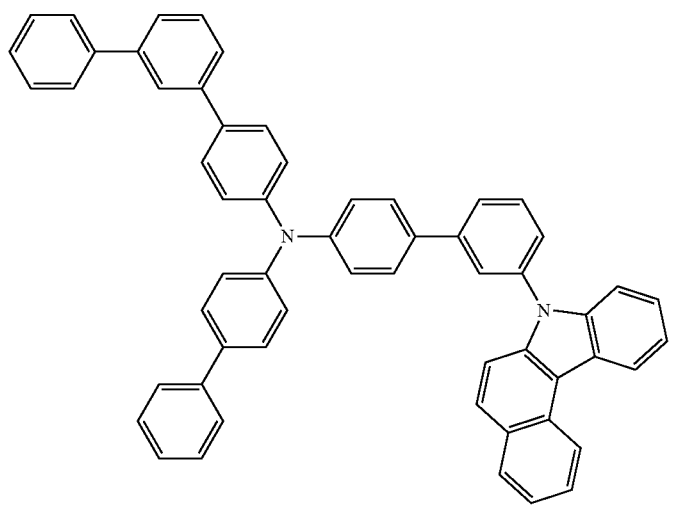

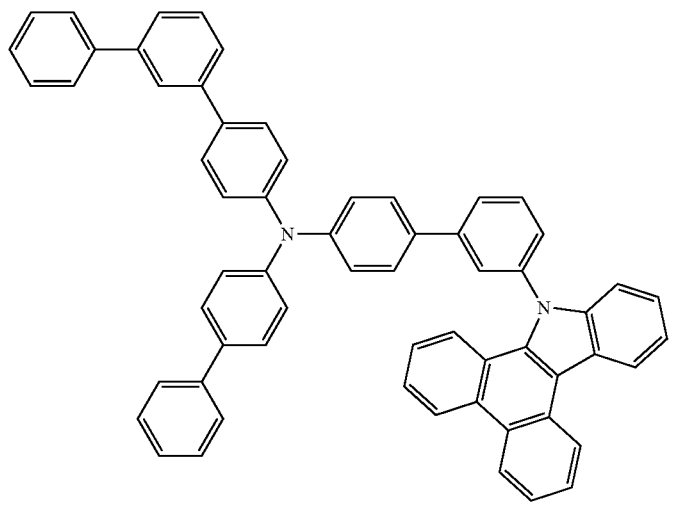
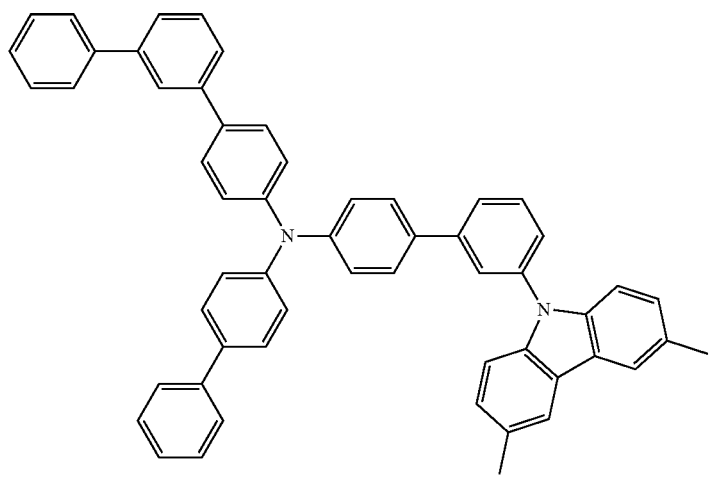
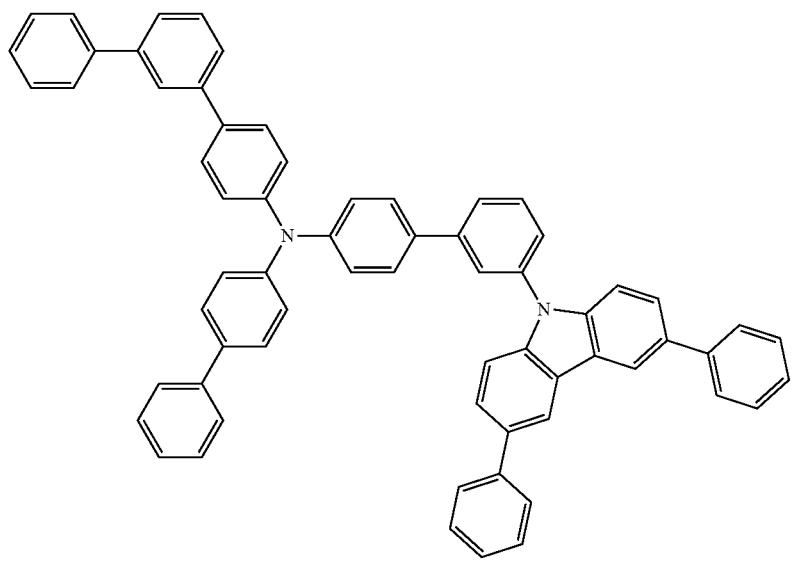

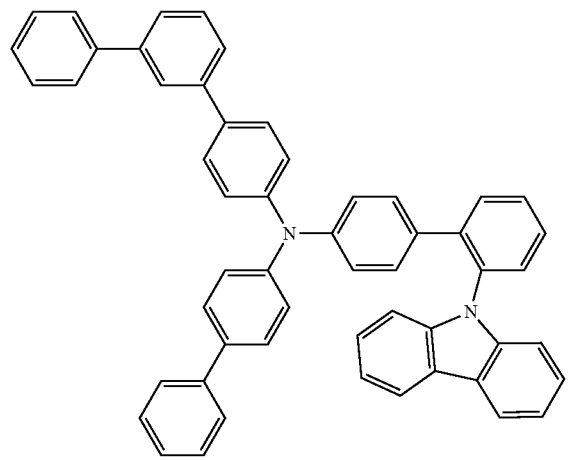
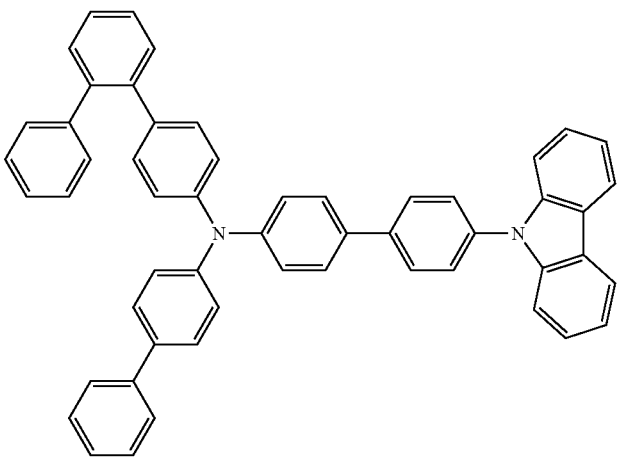
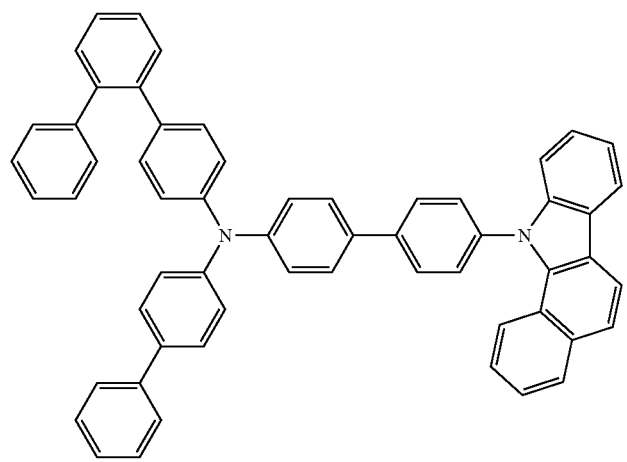
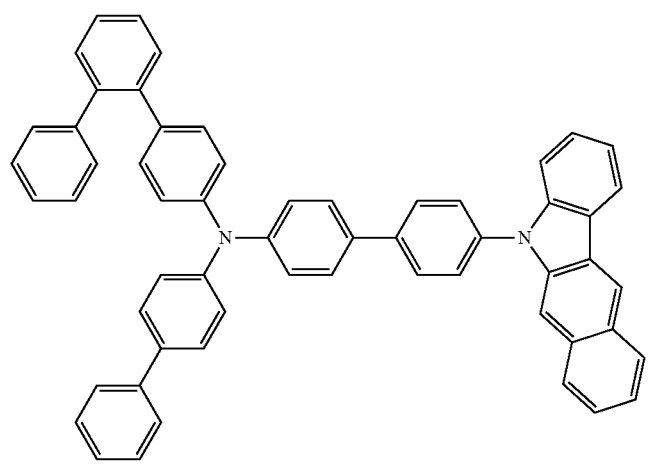

-continued
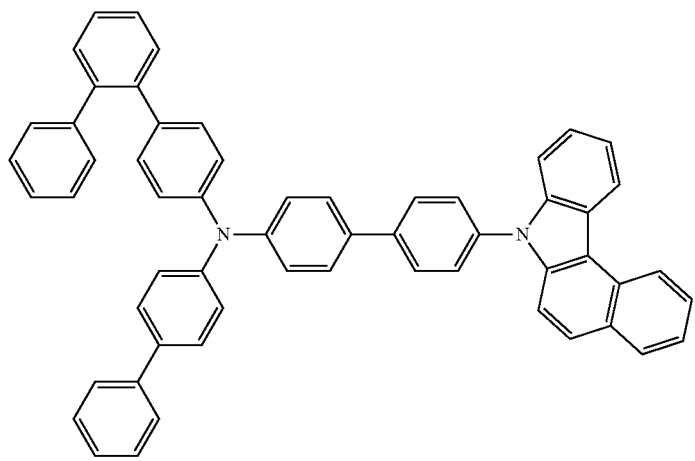
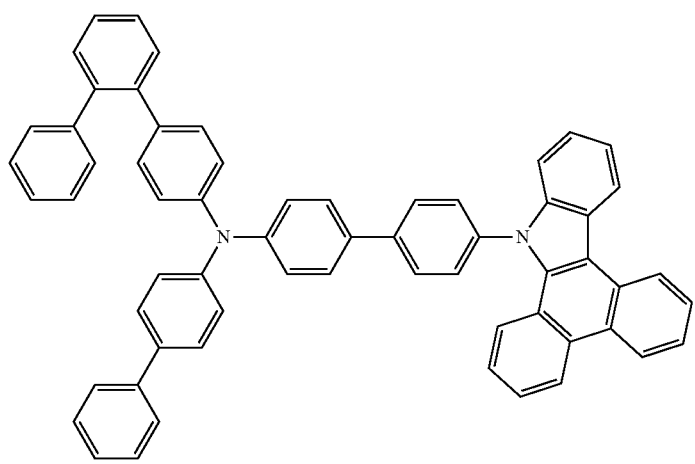
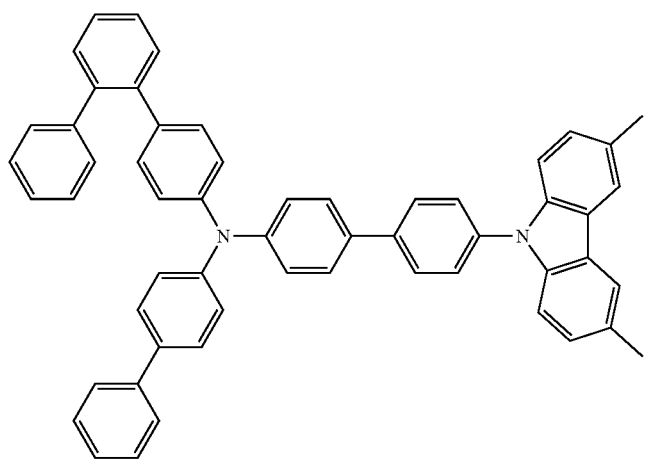

-continued
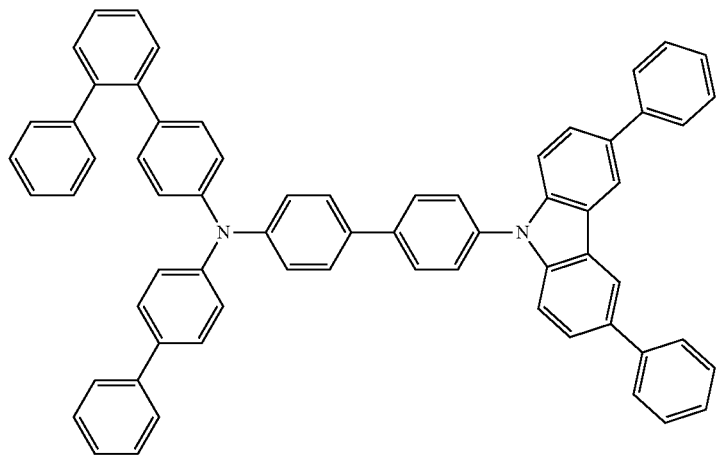
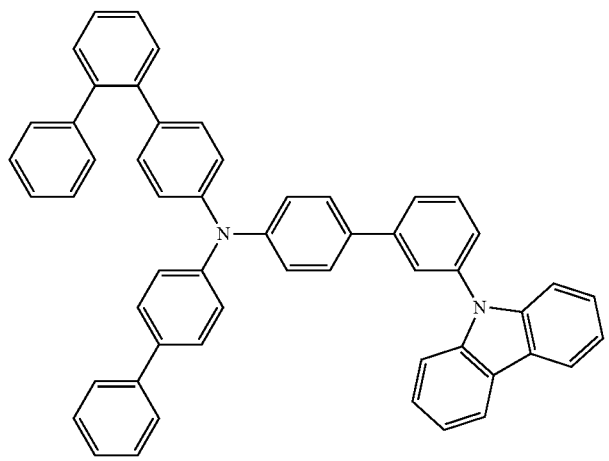
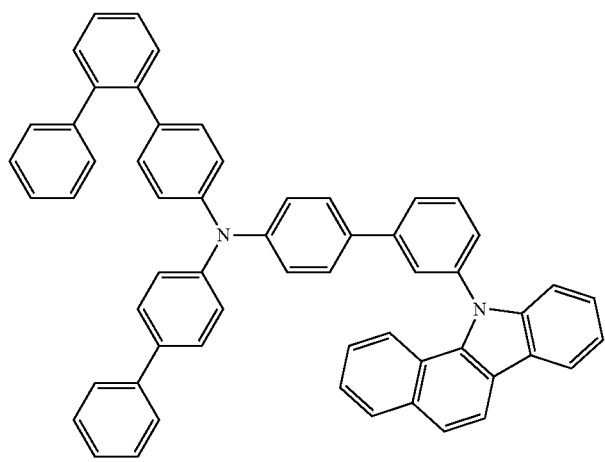

-continued
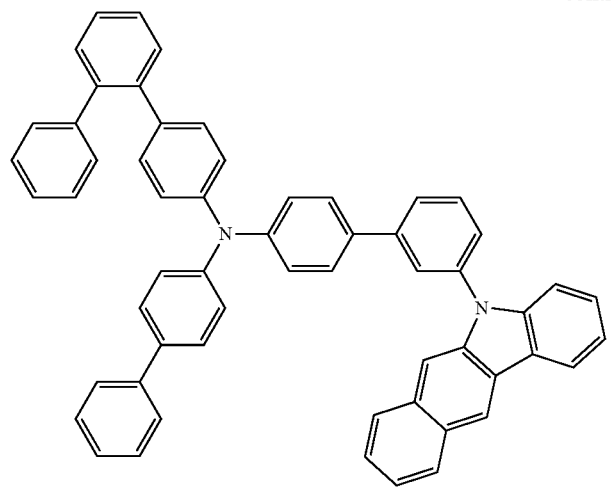
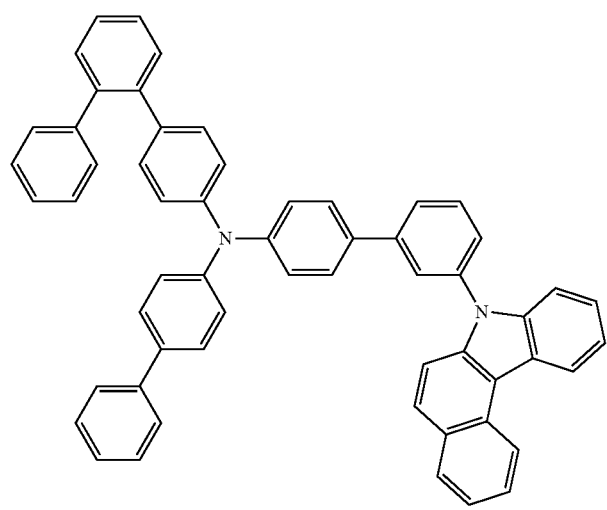
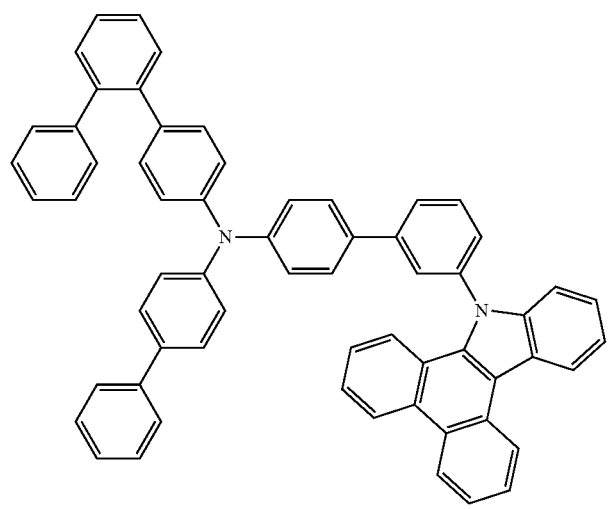

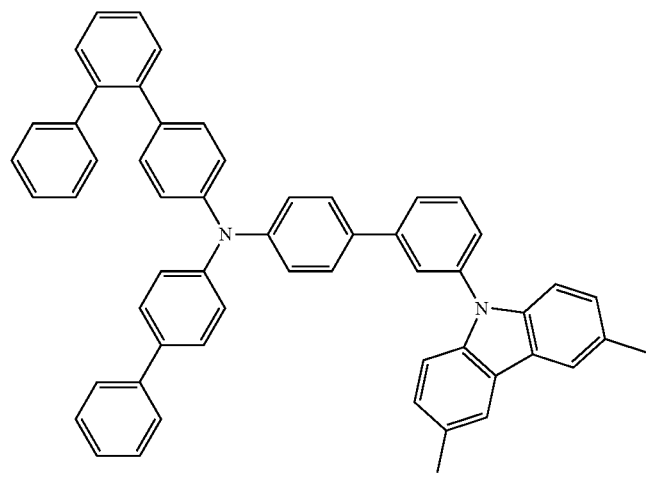 [SMILES: Cc1ccc2c(c1)c1cc(C)ccc1n2-c1cccc(-c2ccc(N(c3ccc(-c4ccccc4)cc3)c3ccc(-c4ccccc4-c4ccccc4)cc3)cc2)c1]
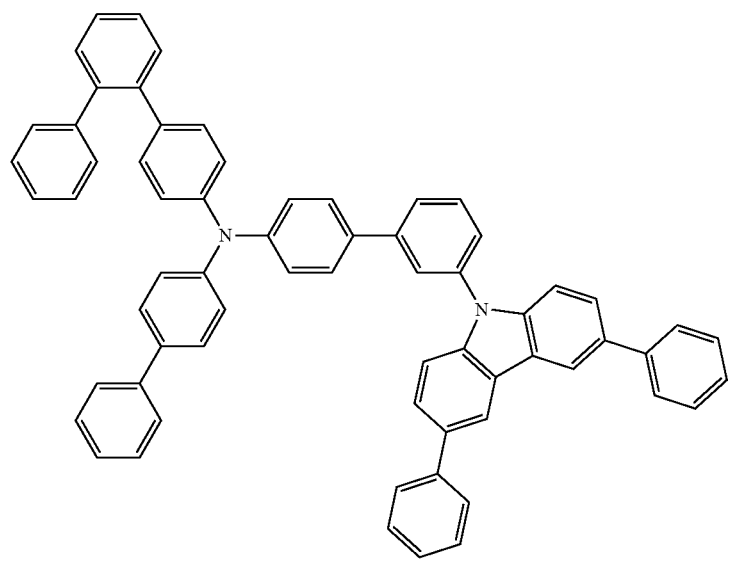
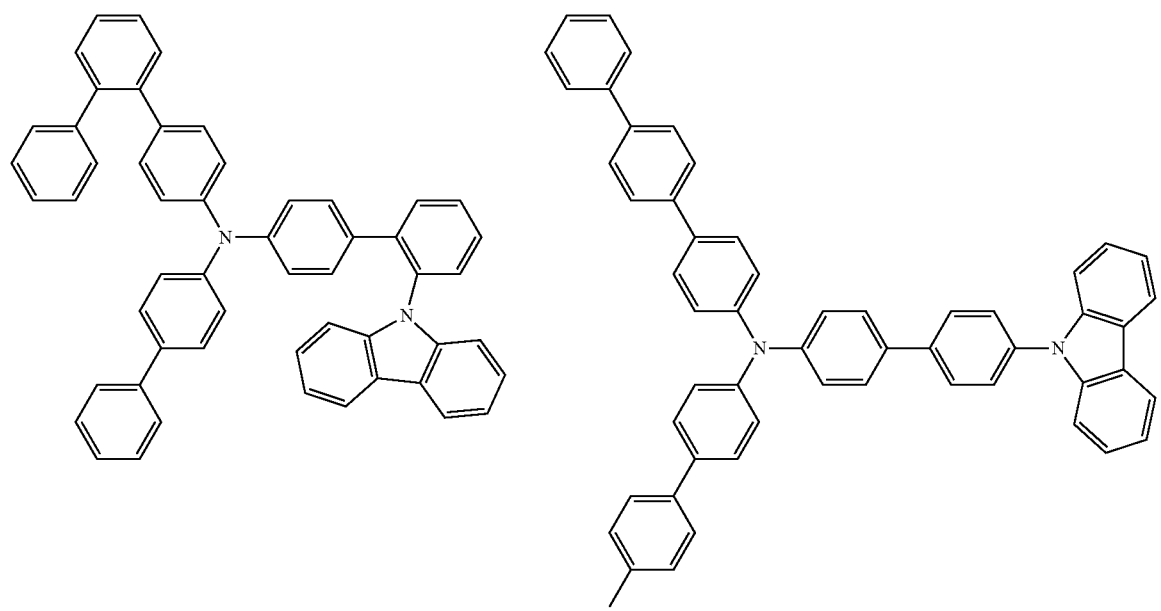

-continued
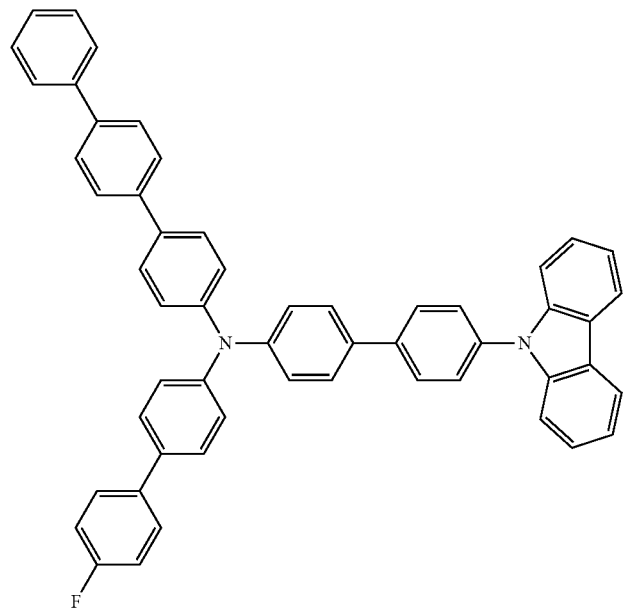
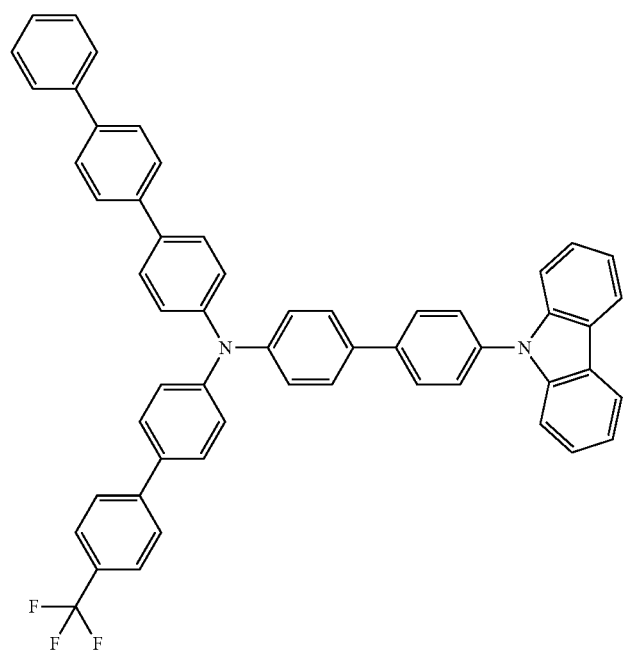

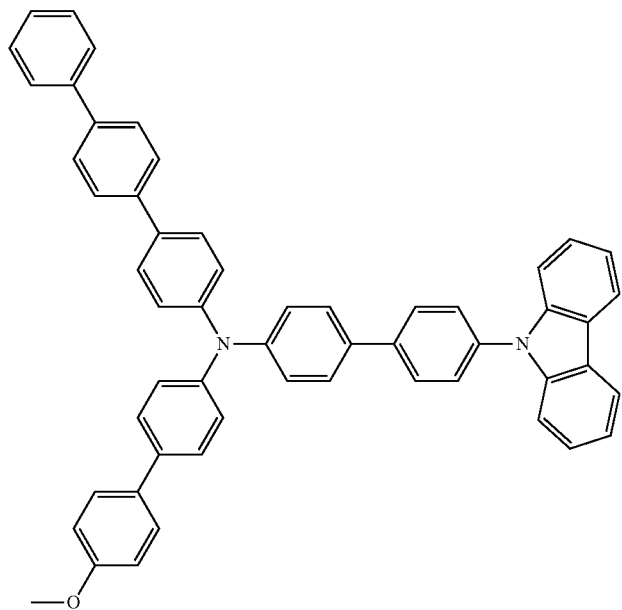
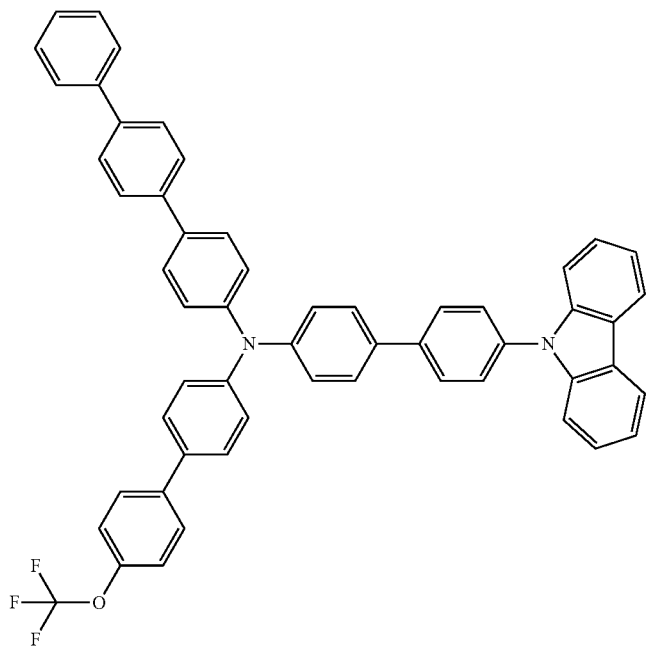

-continued
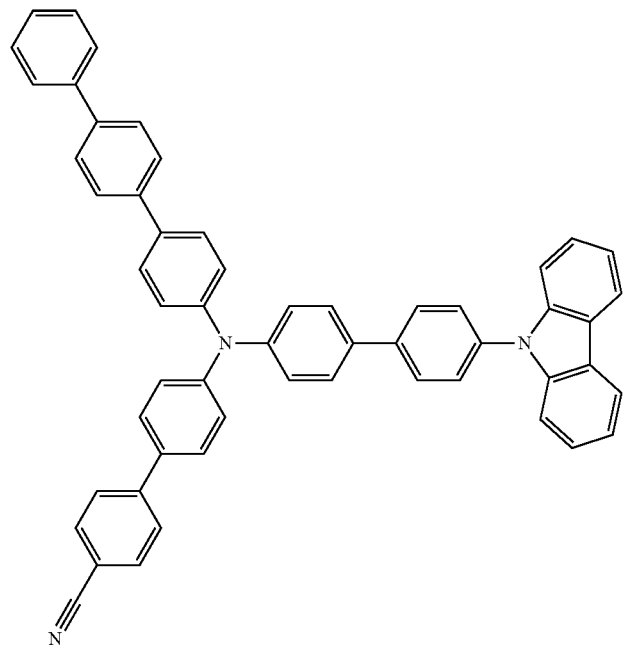
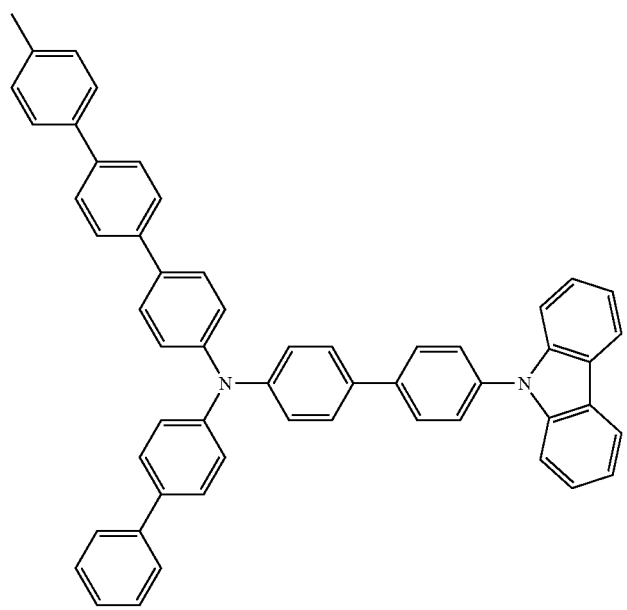

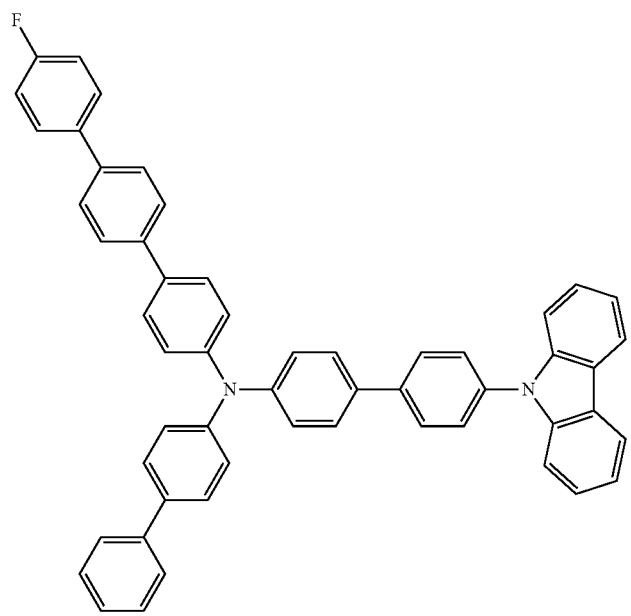
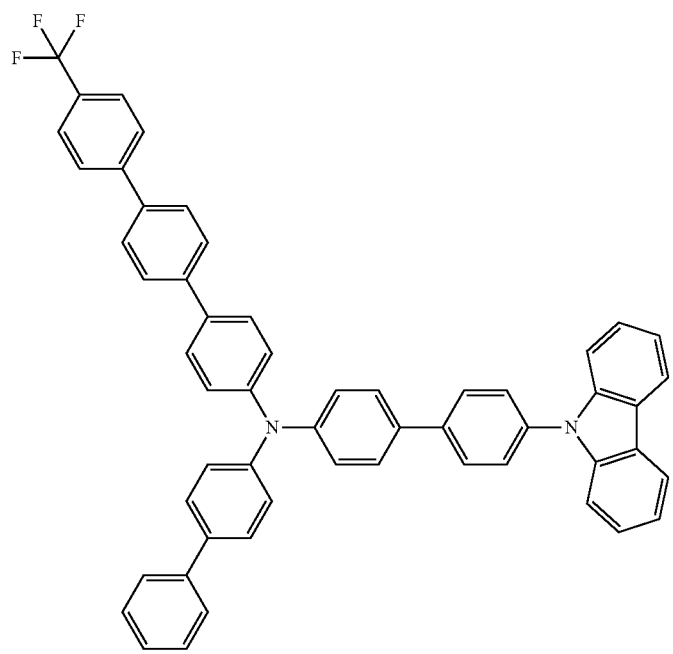

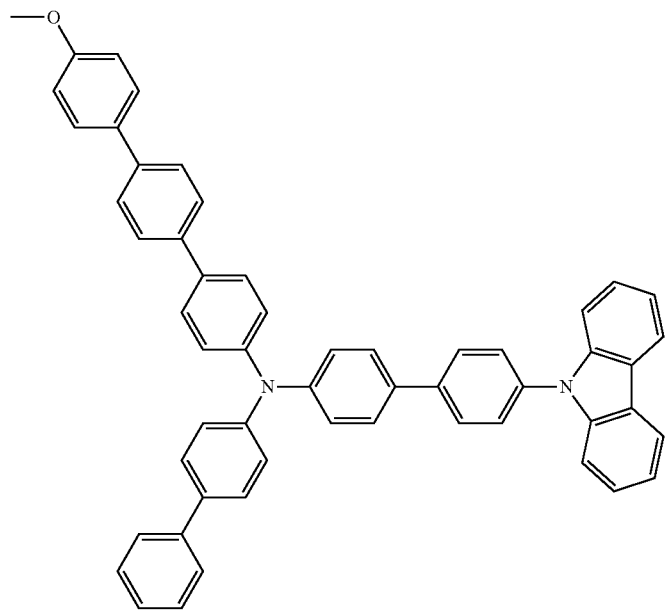
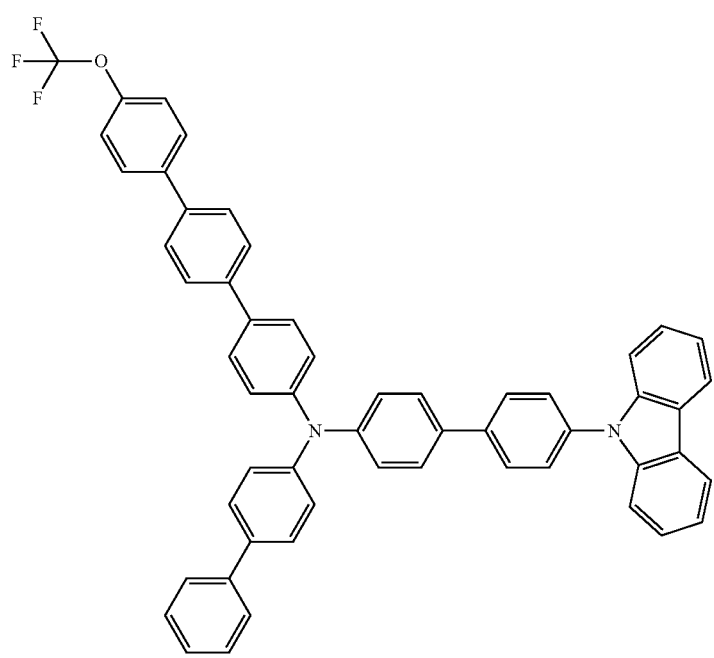

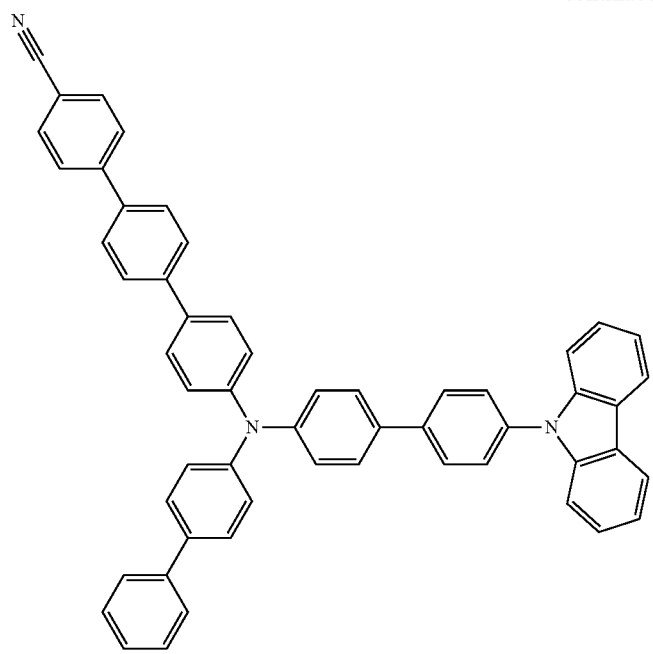
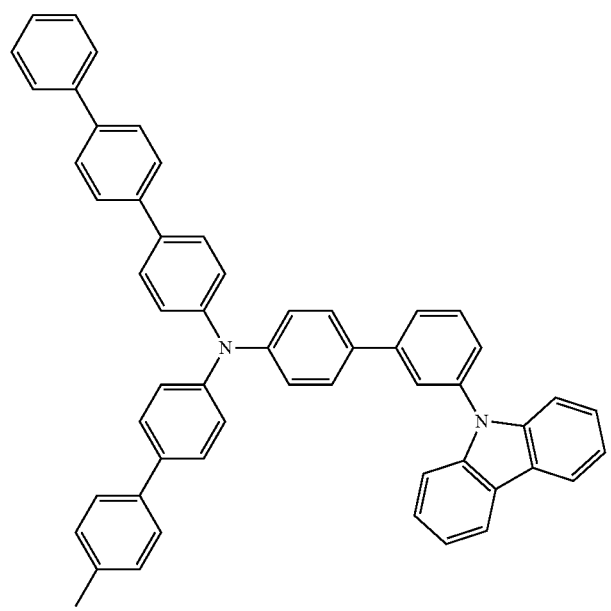

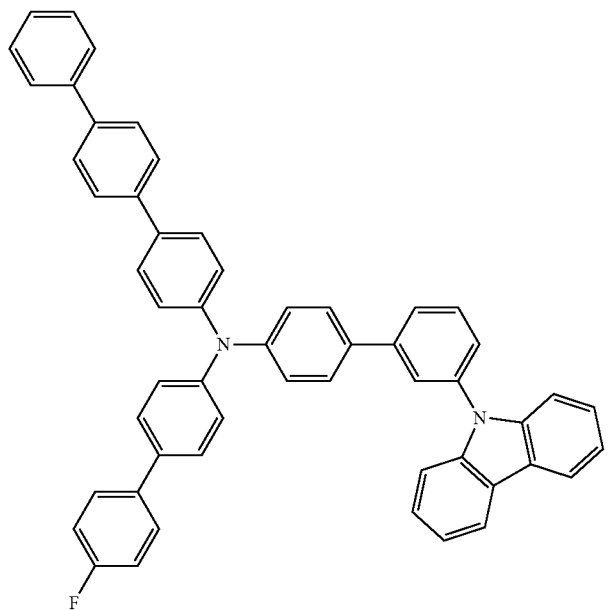
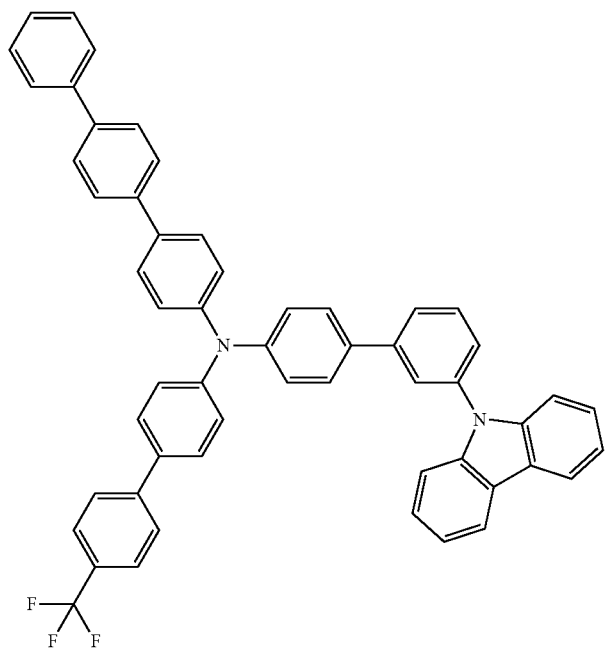

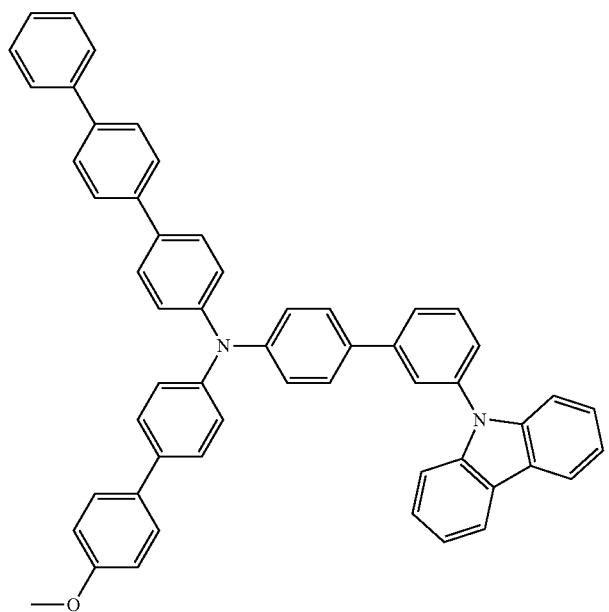
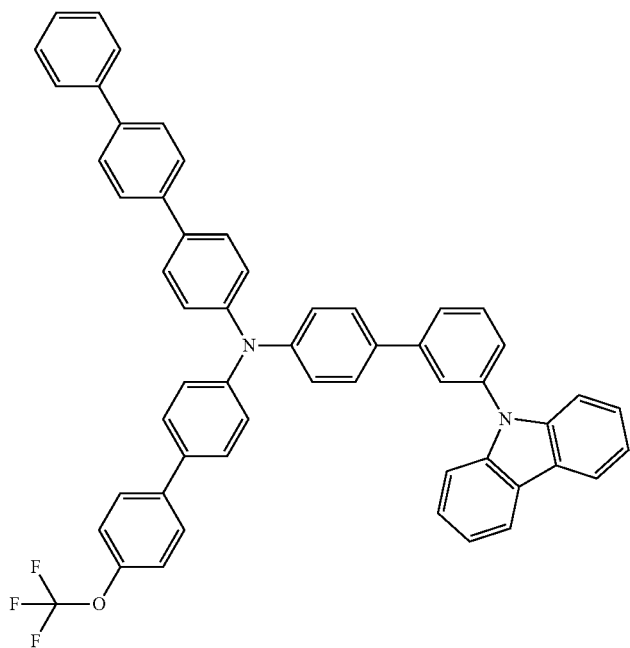

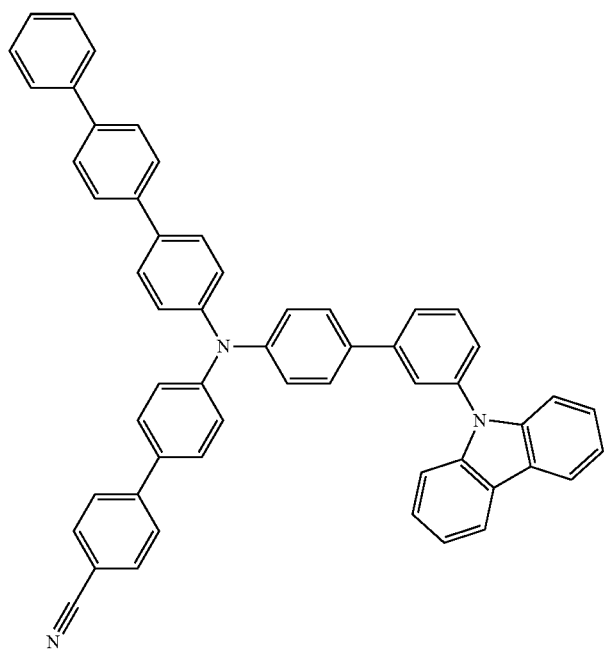
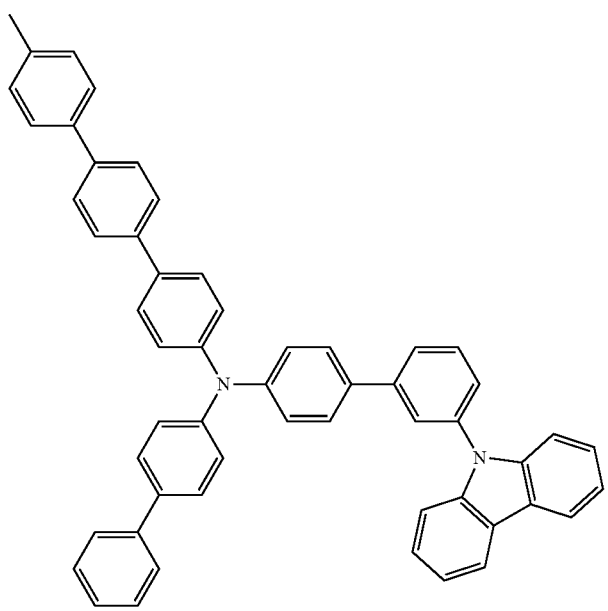

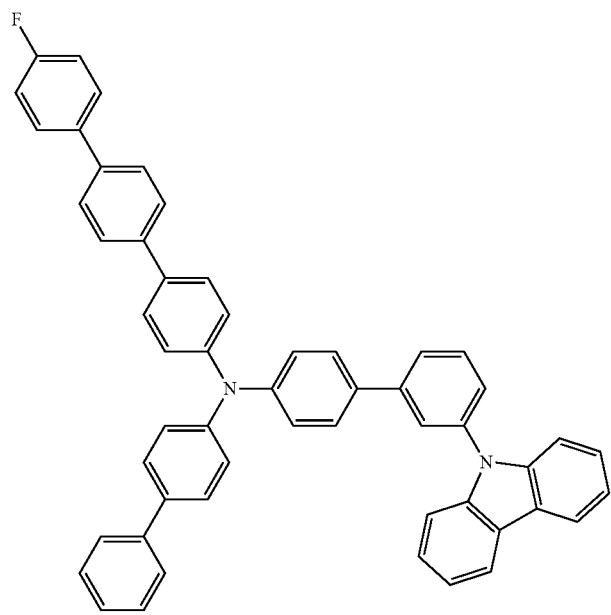
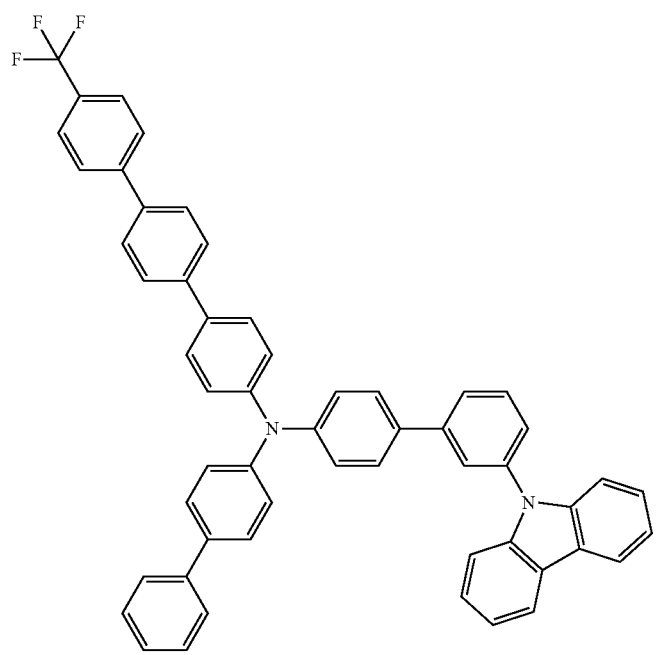

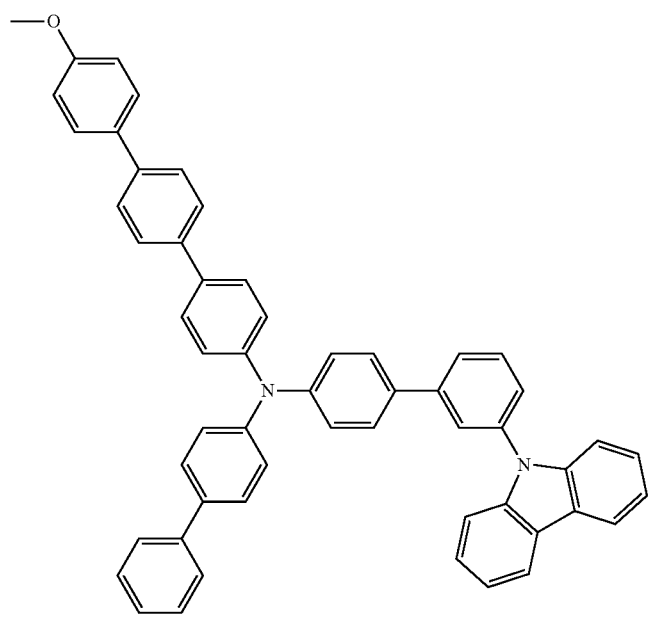
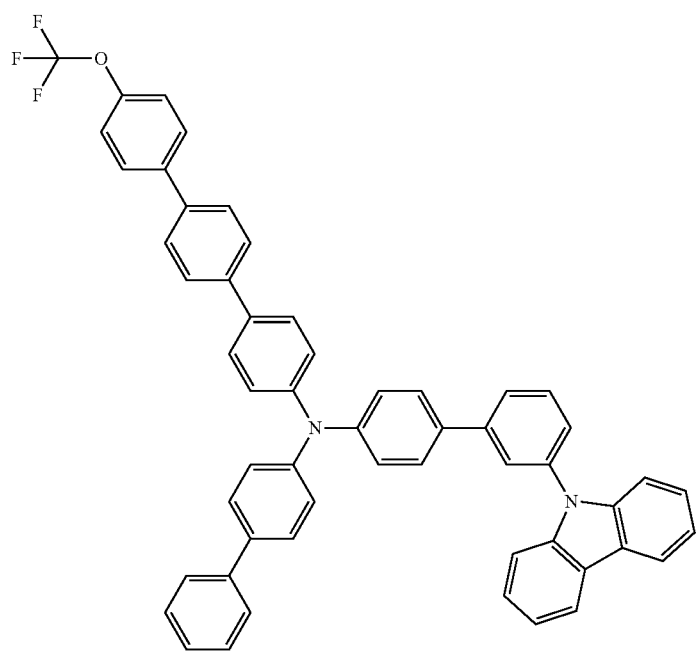

-continued
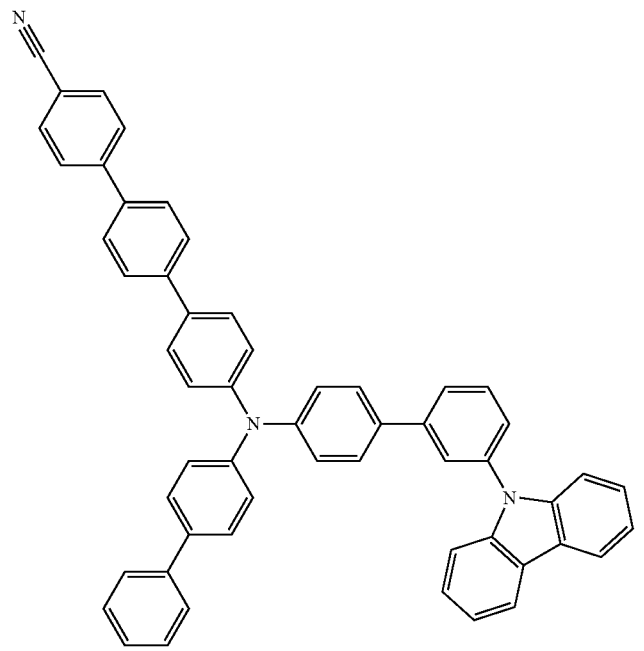
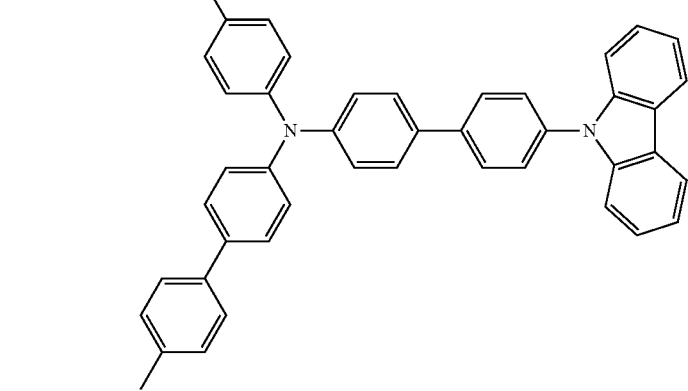
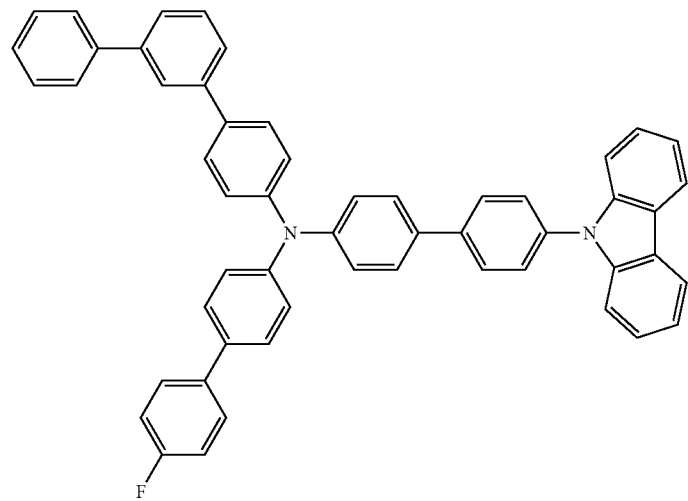

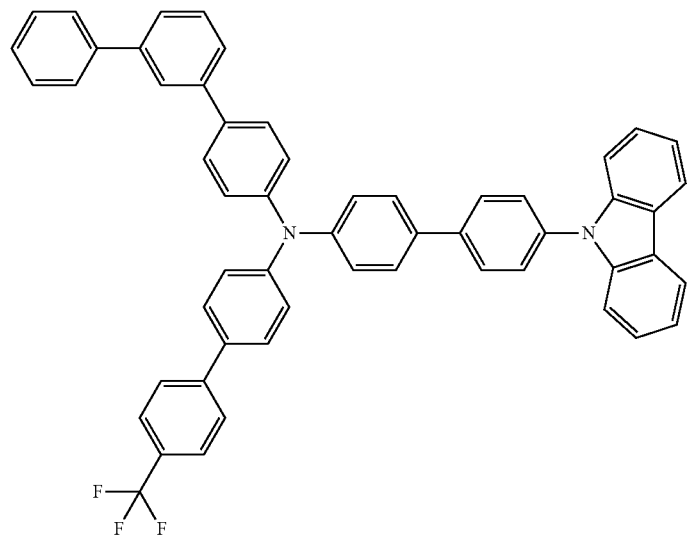
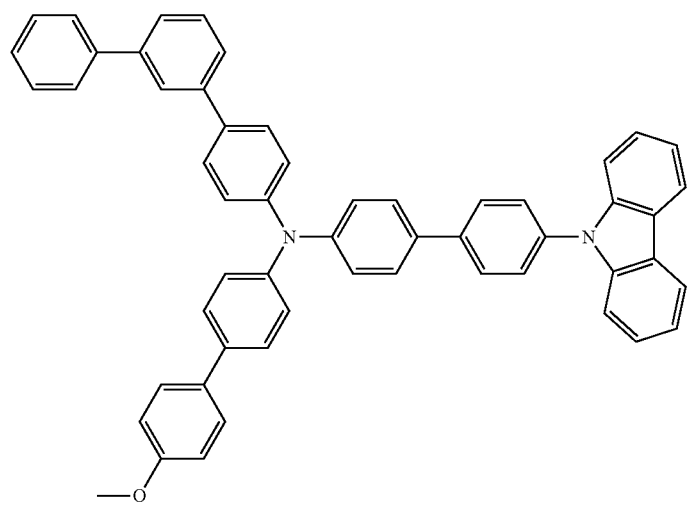
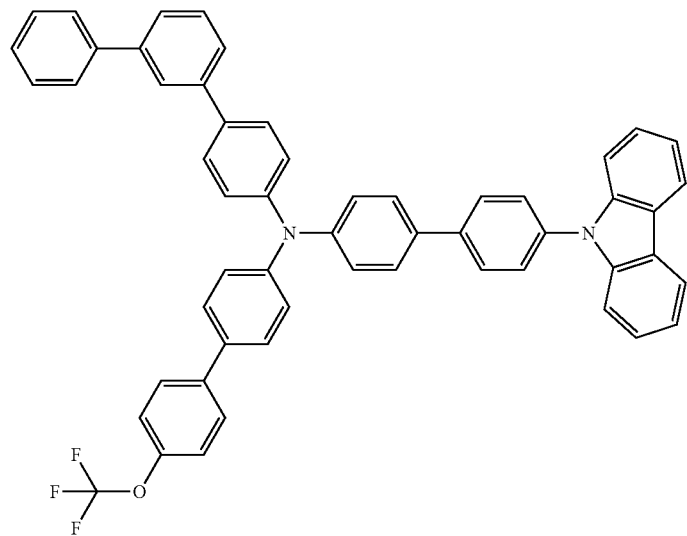

-continued
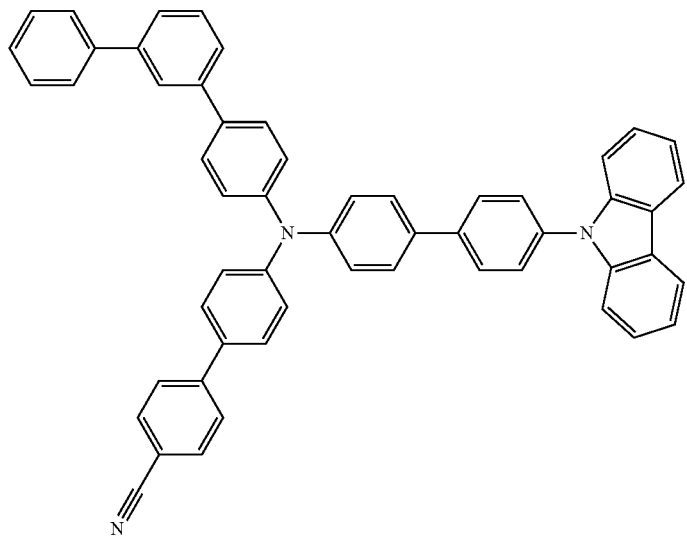
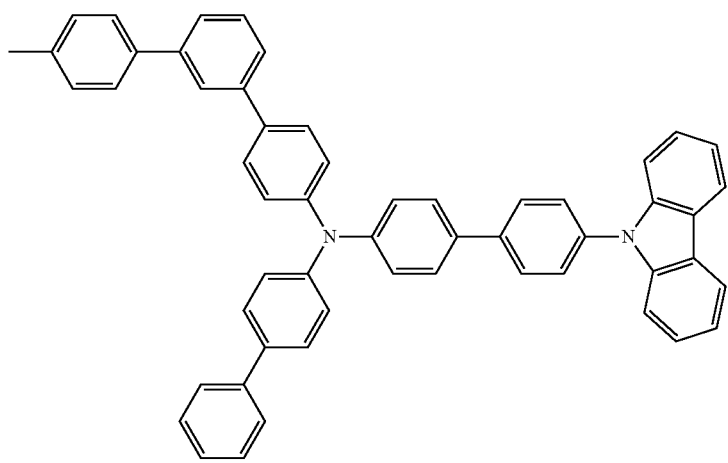
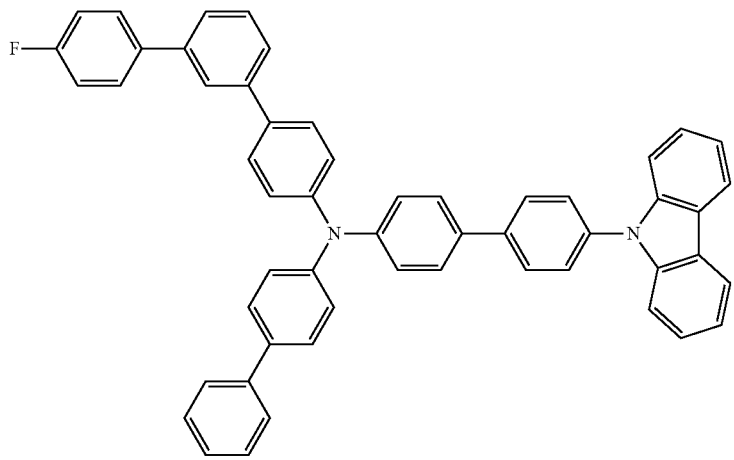

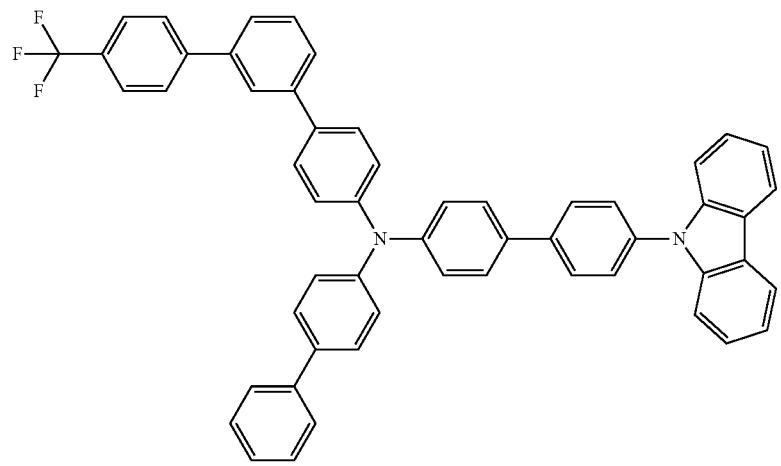
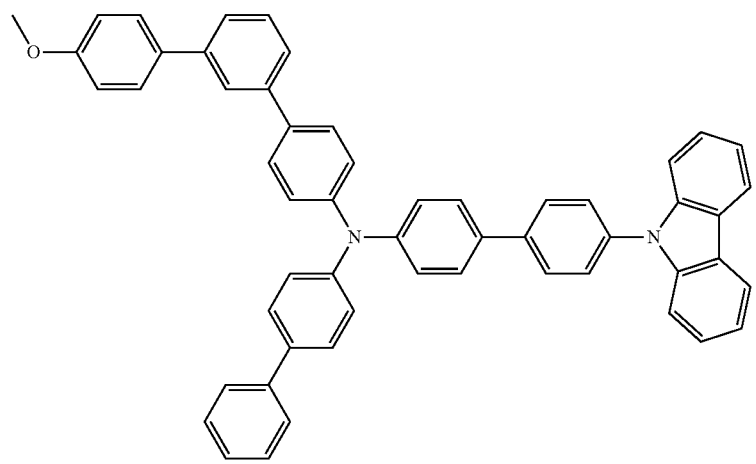
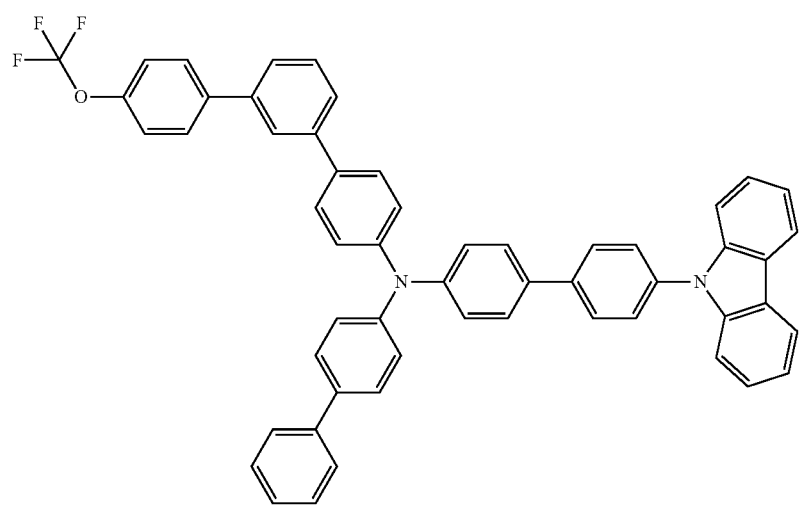

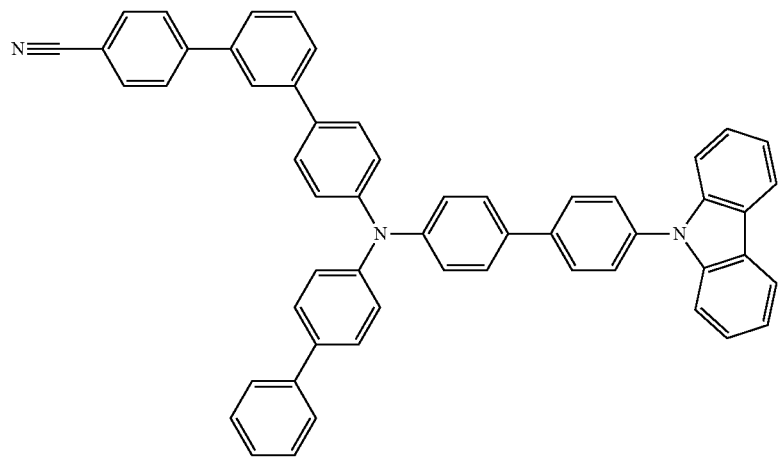
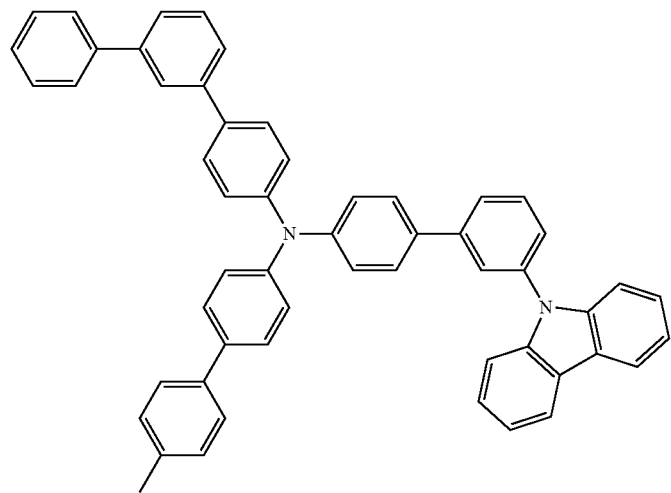
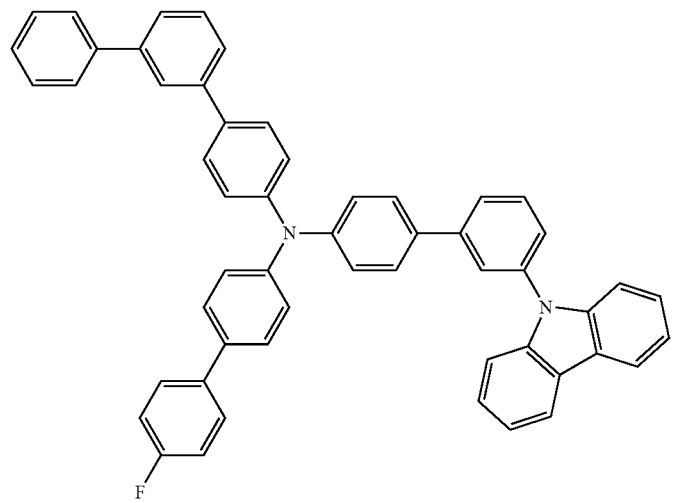

-continued
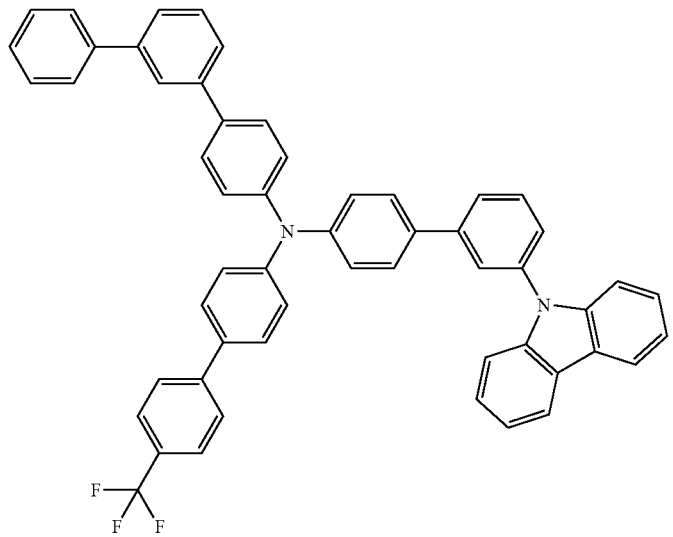
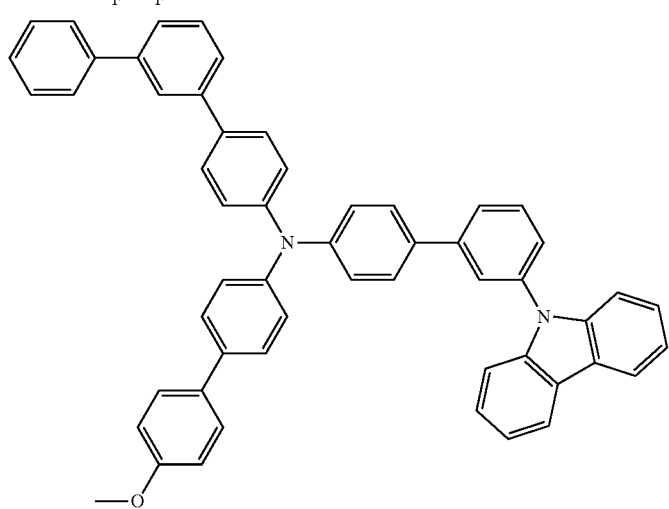
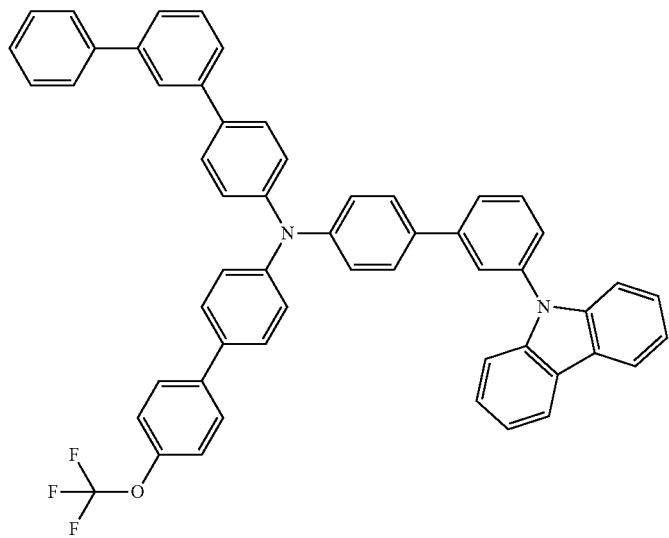

-continued
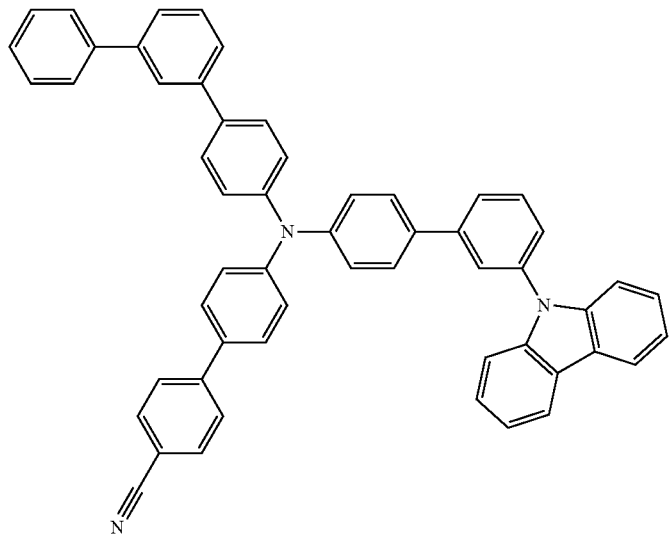
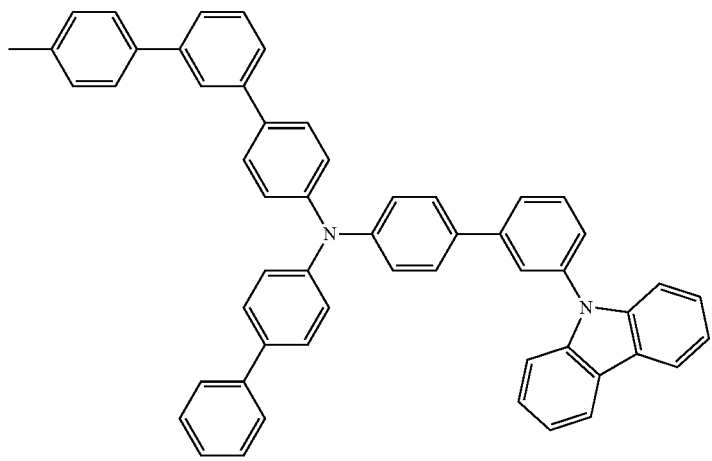
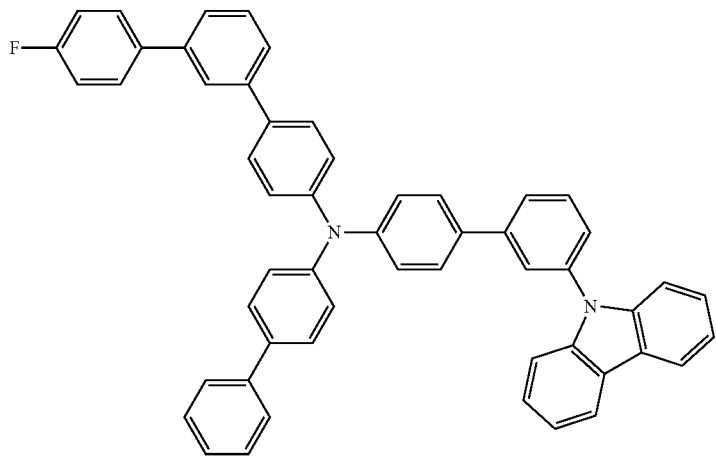

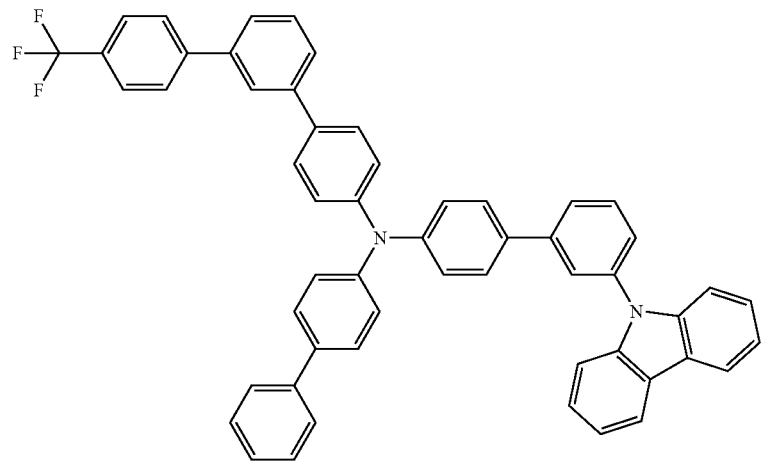
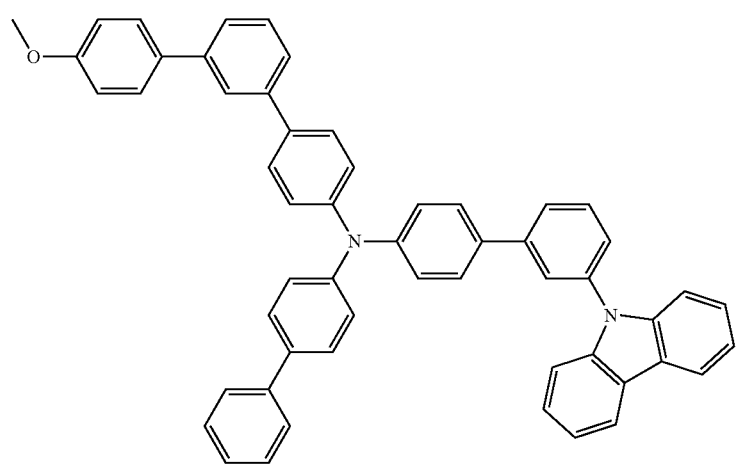
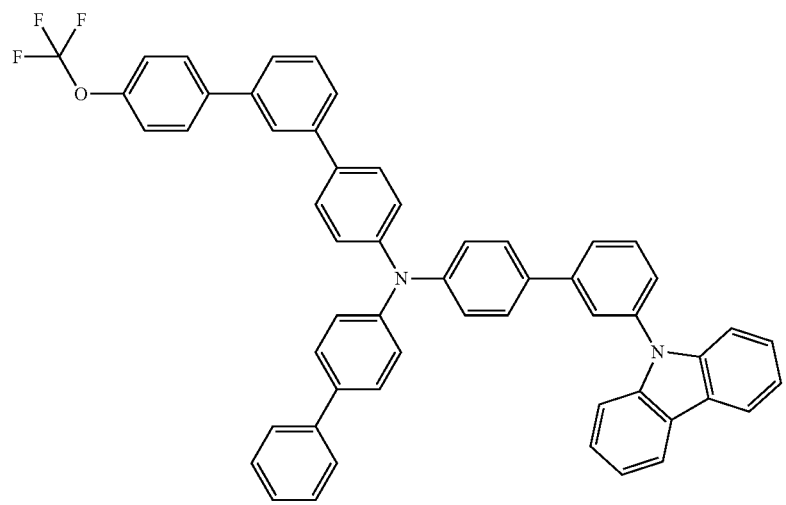

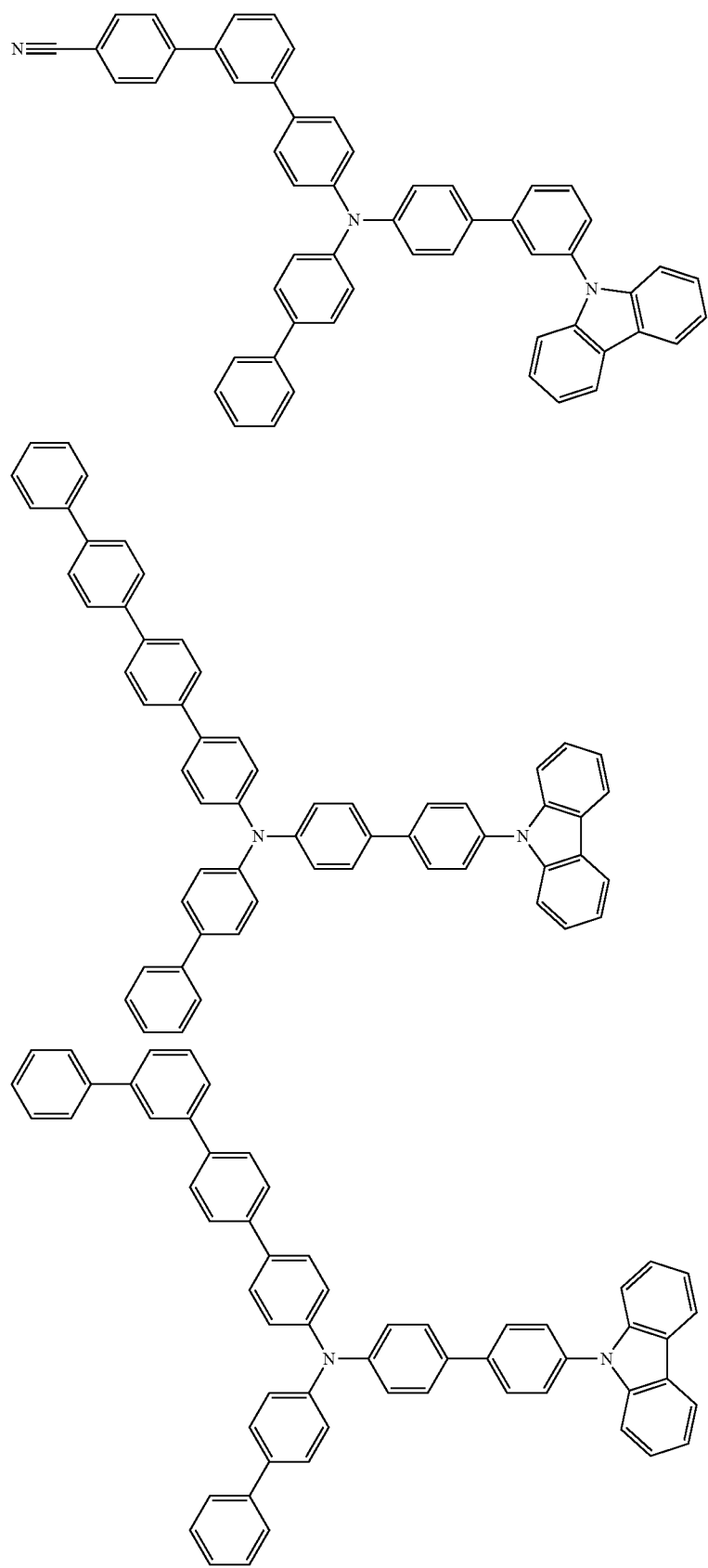

-continued
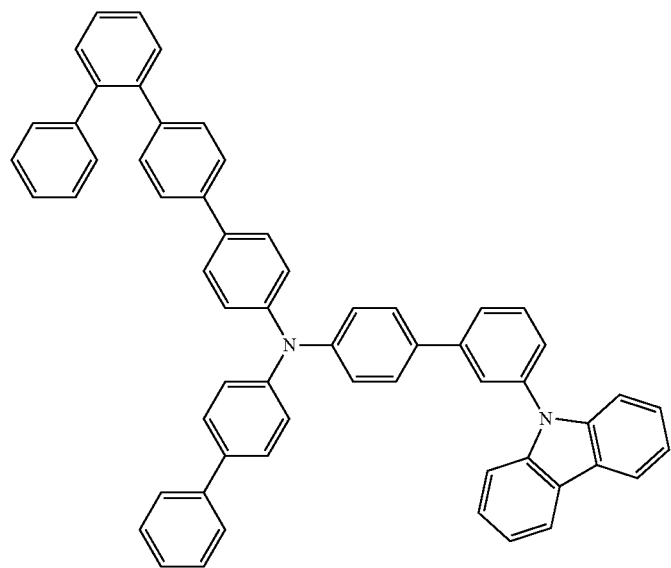
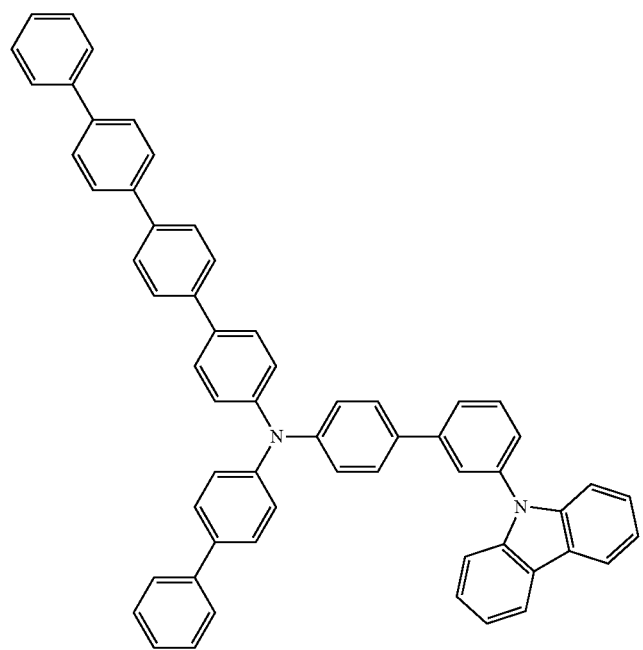

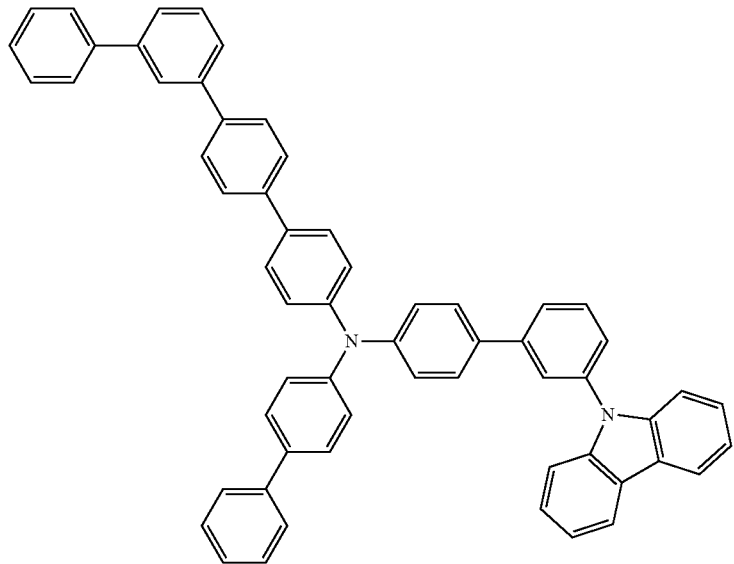
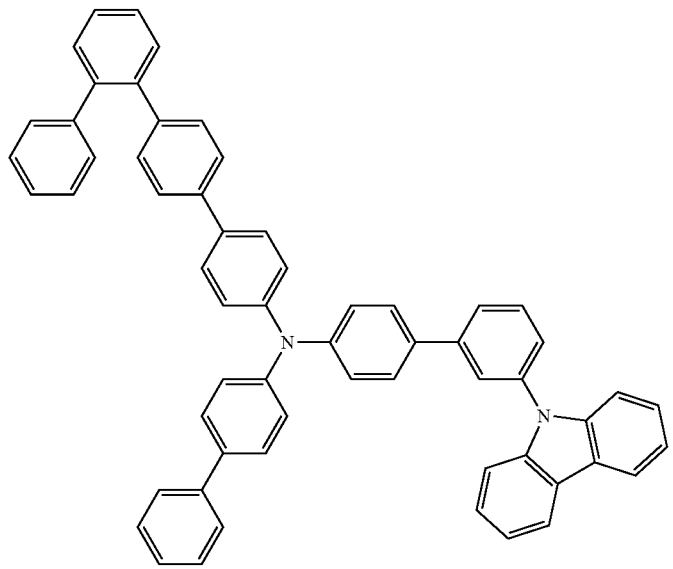
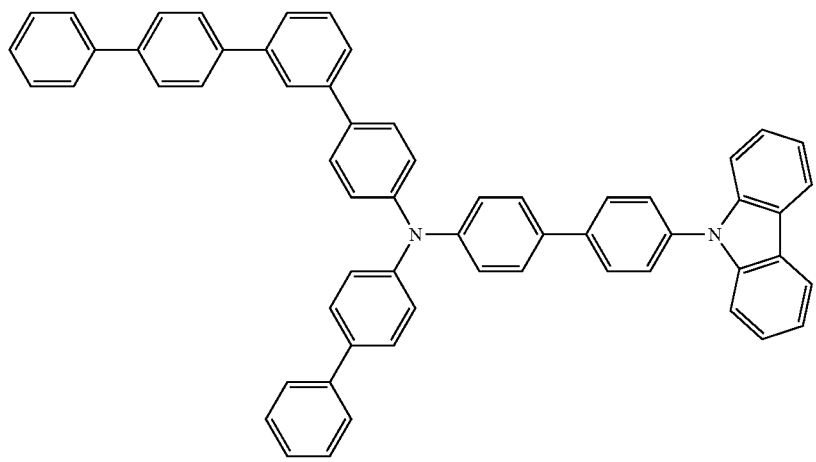

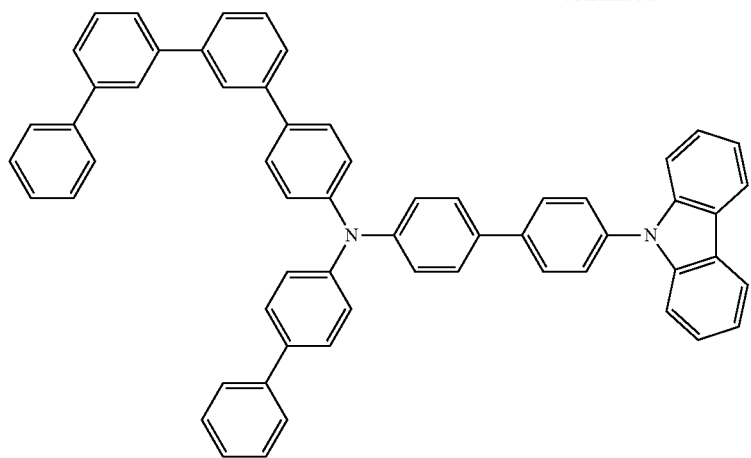
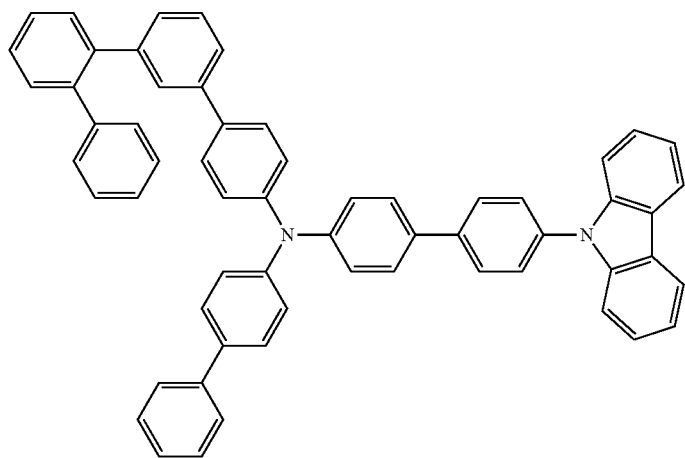
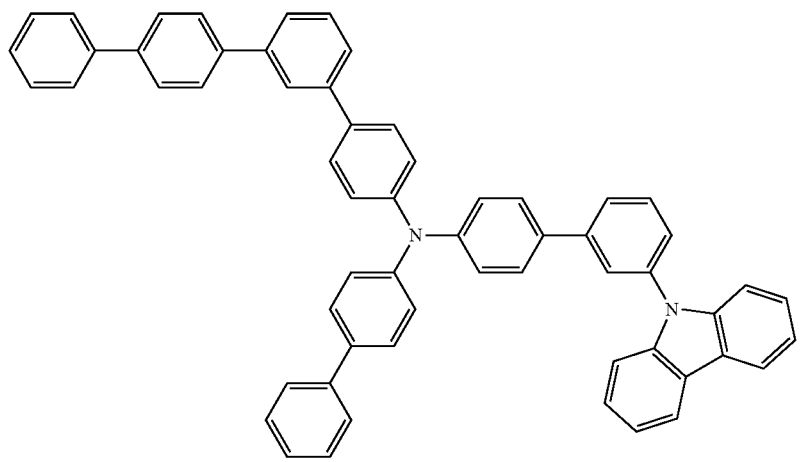

-continued
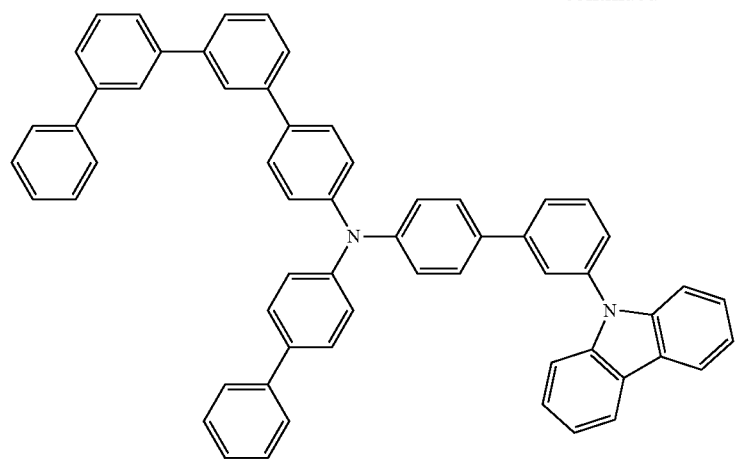
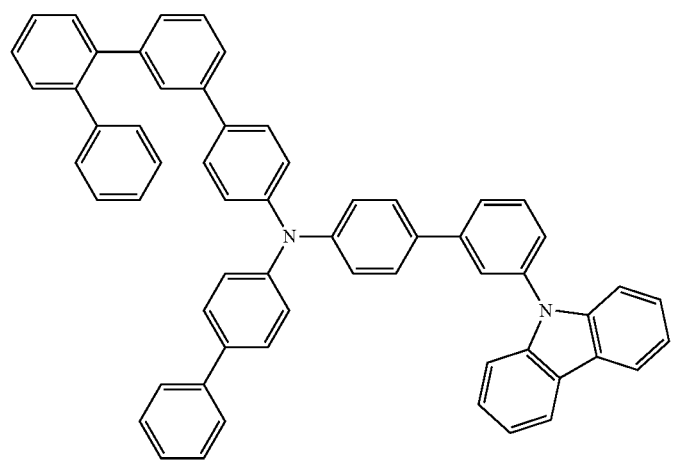
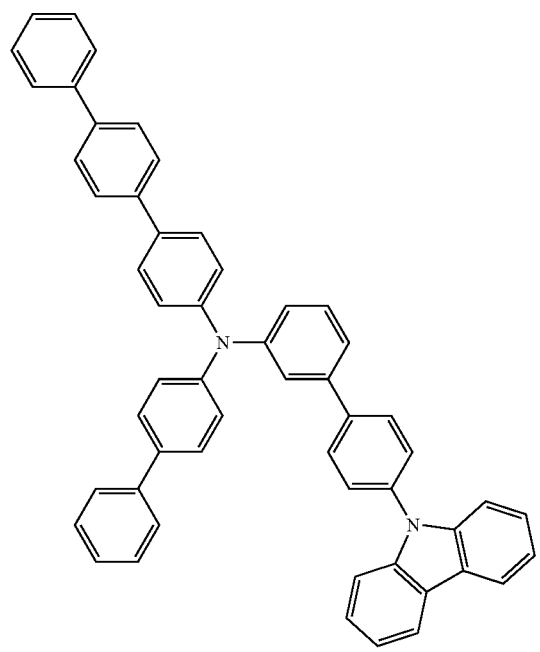
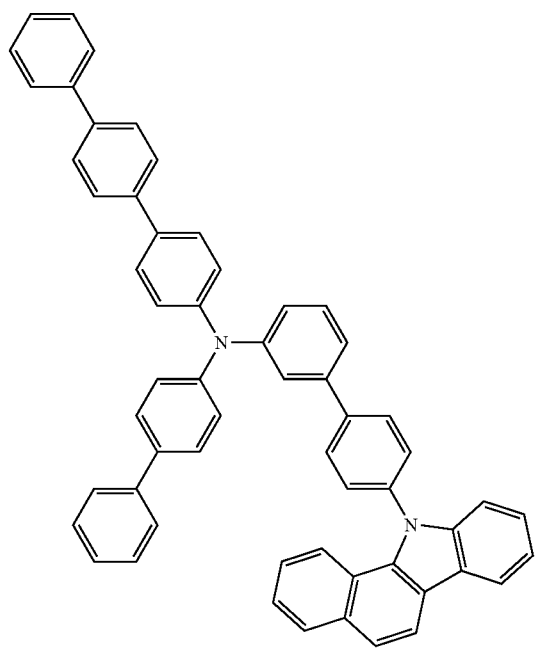

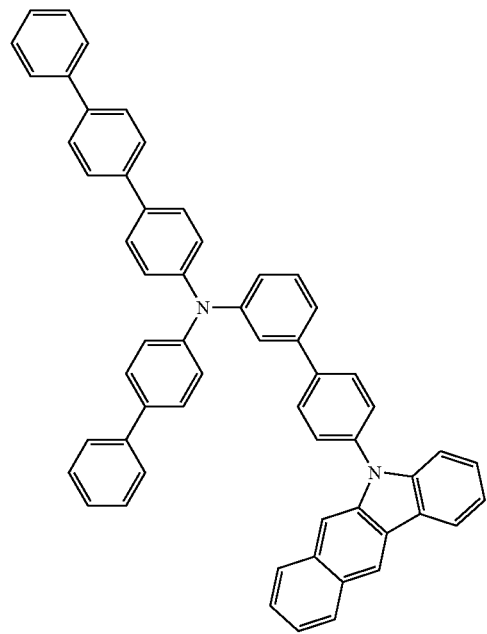
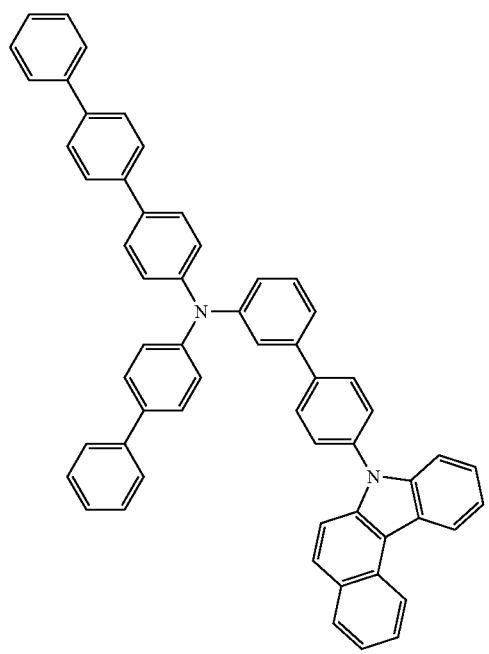
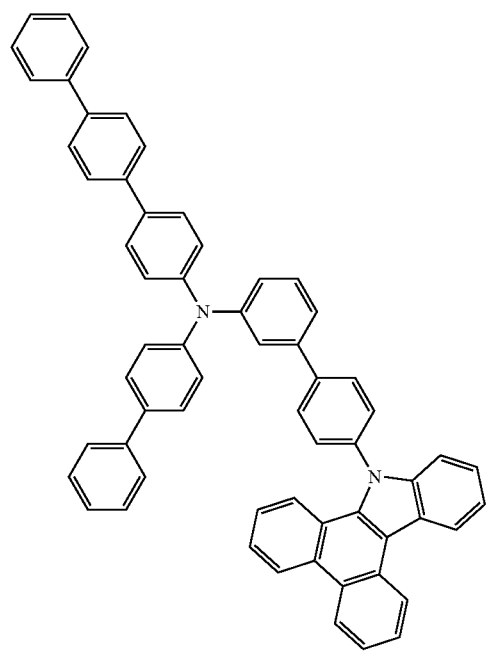
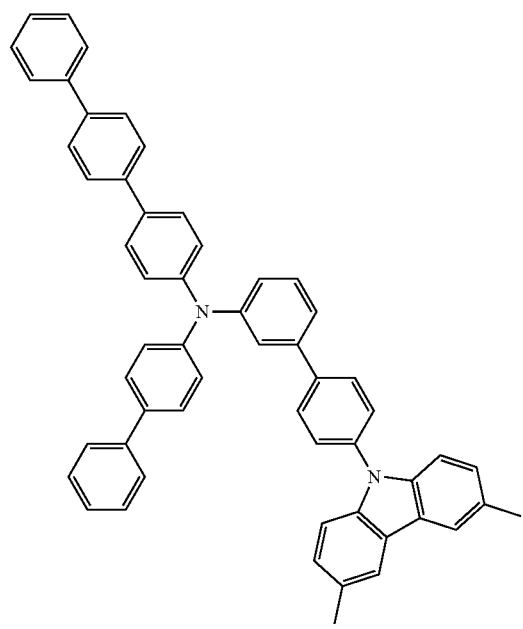

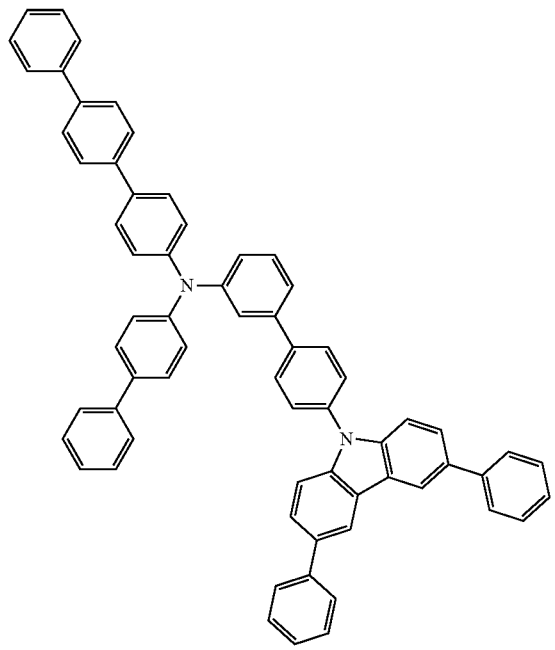
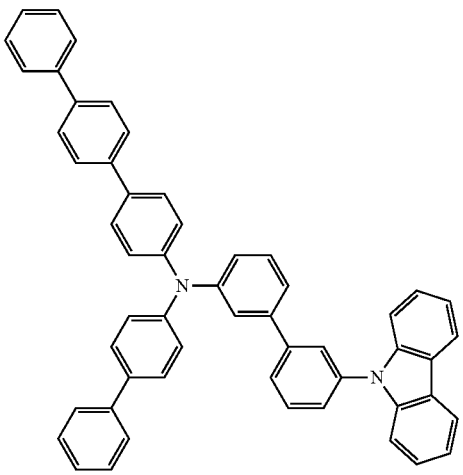
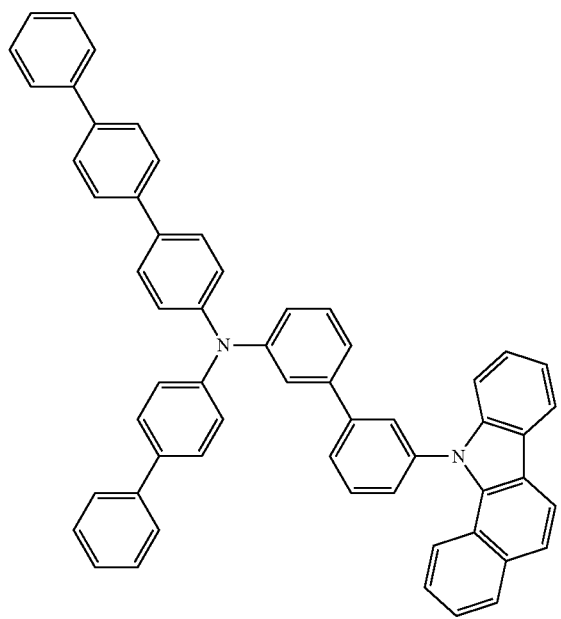
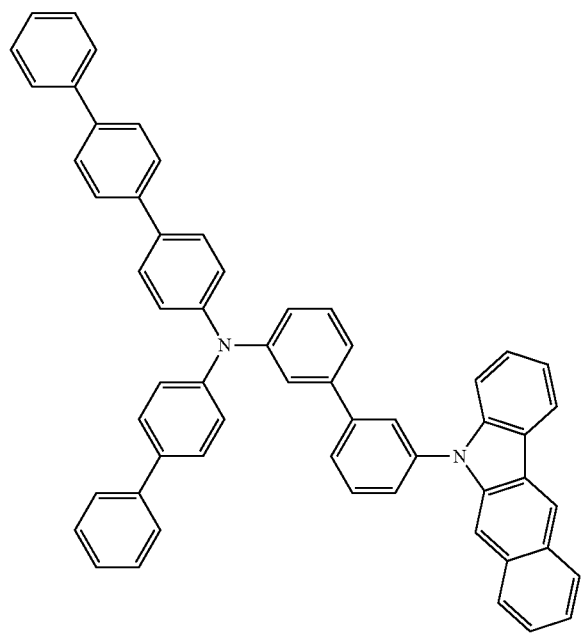

-continued
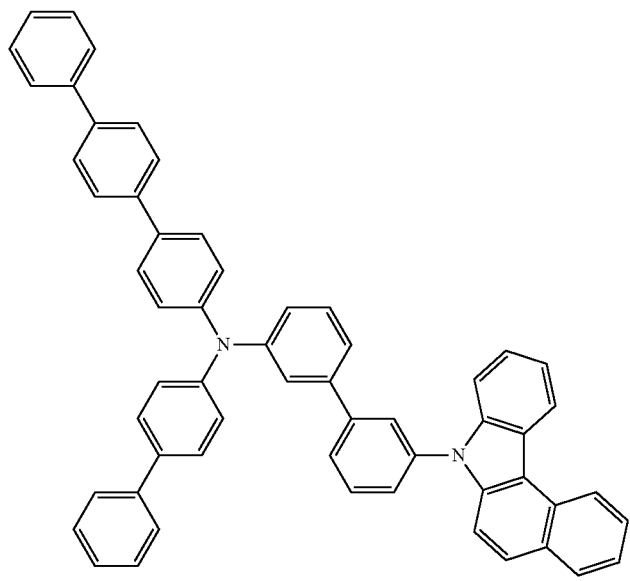
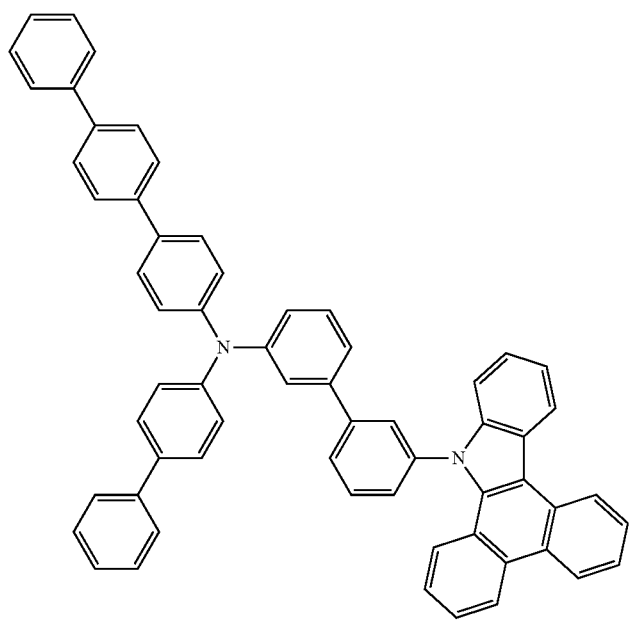

-continued
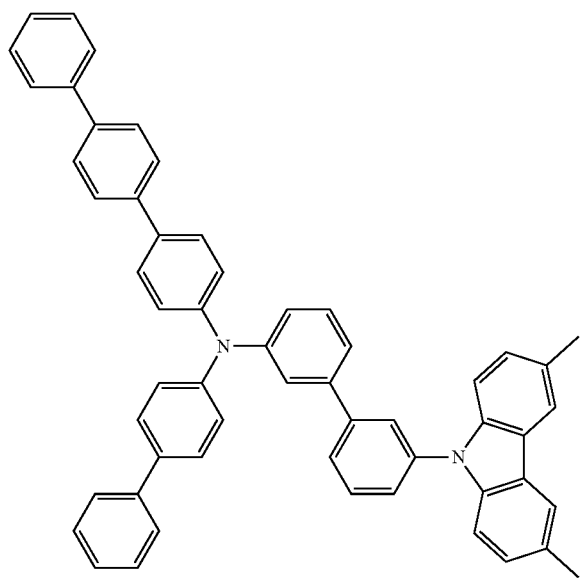
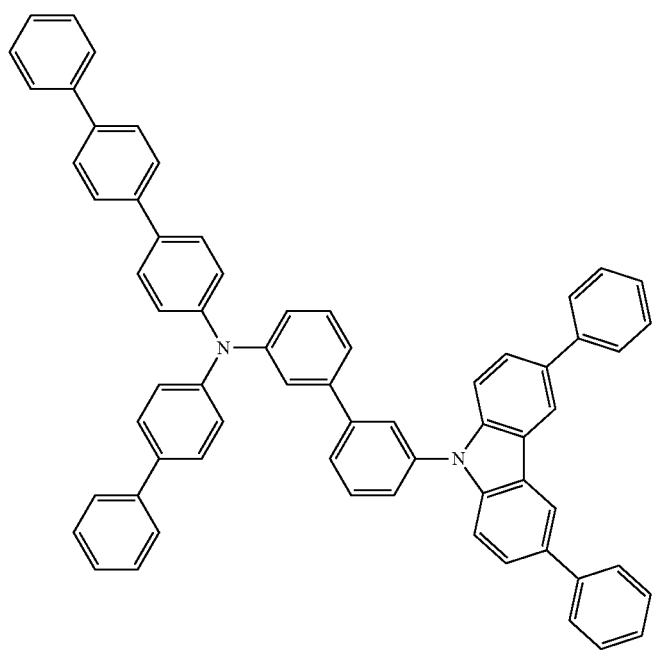

101
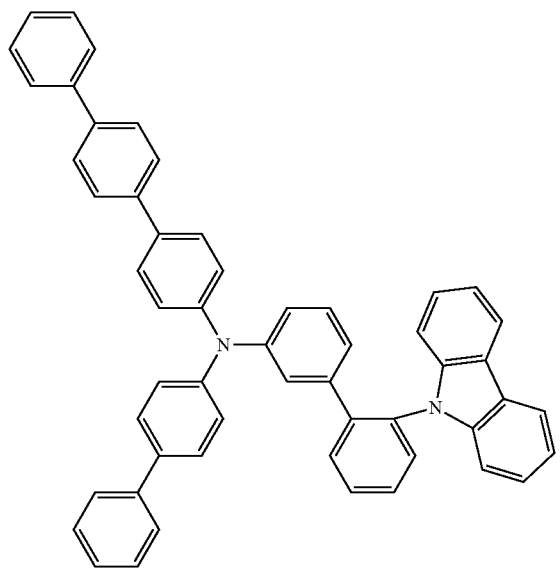
102
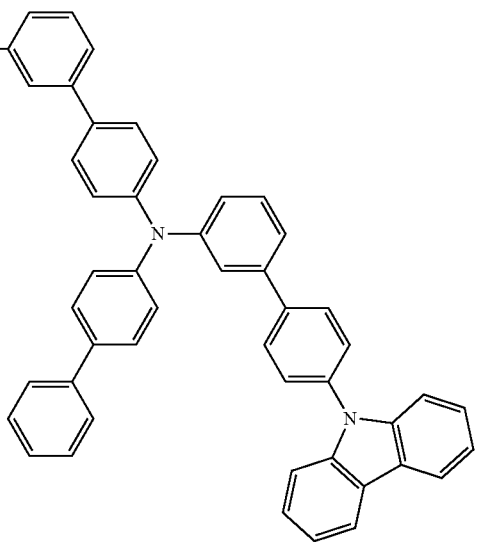
-continued
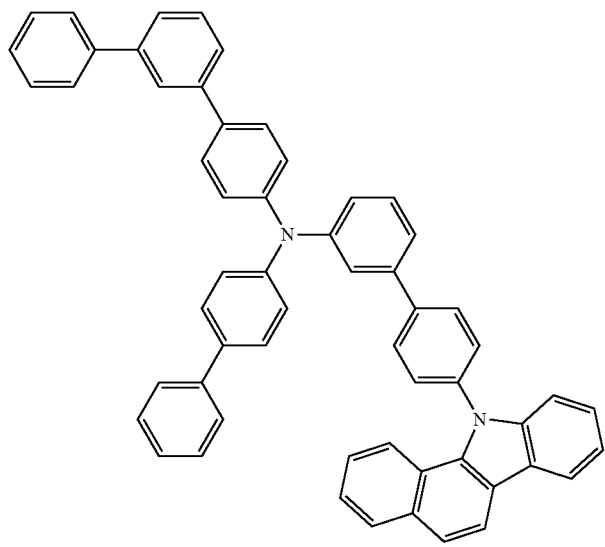
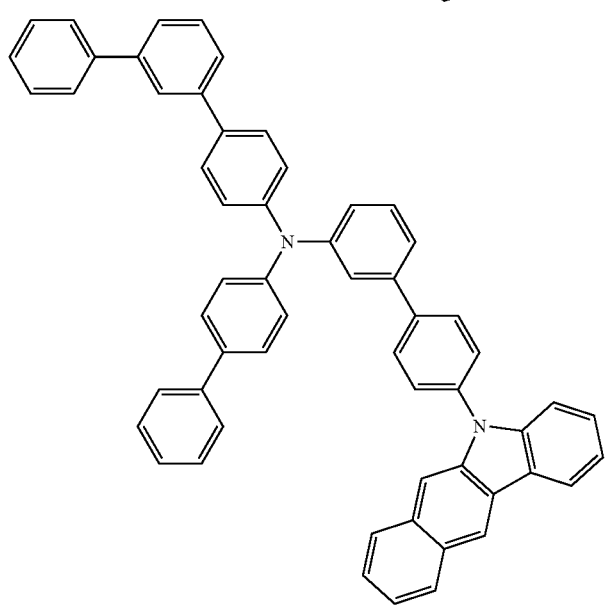

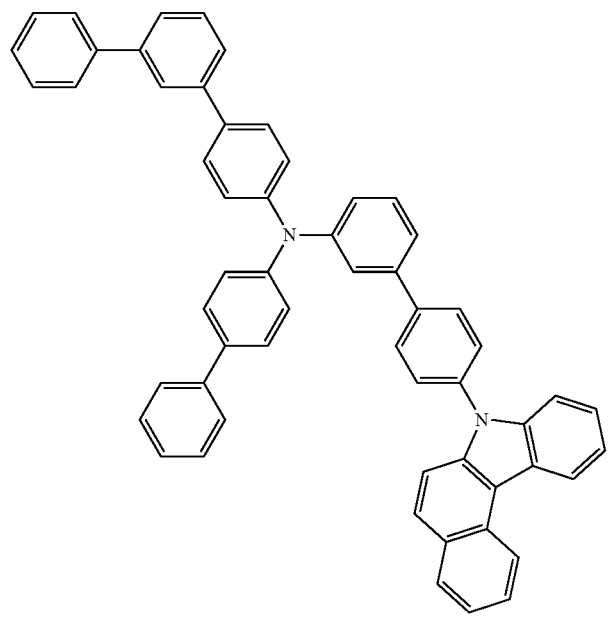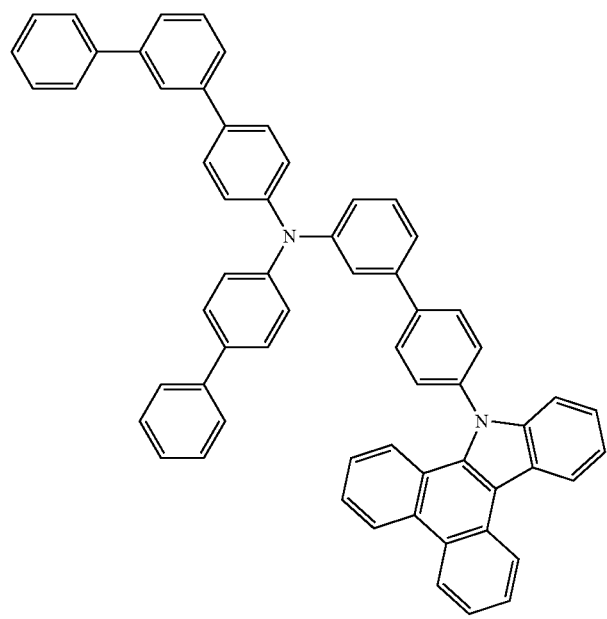

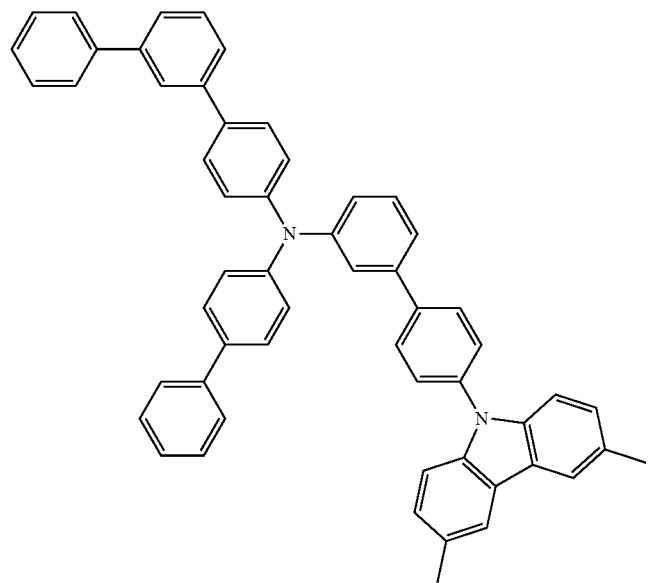
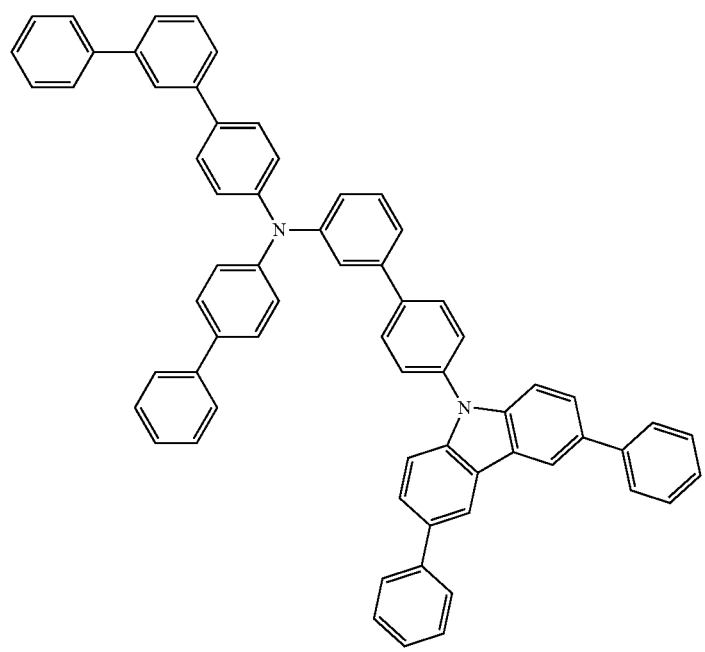
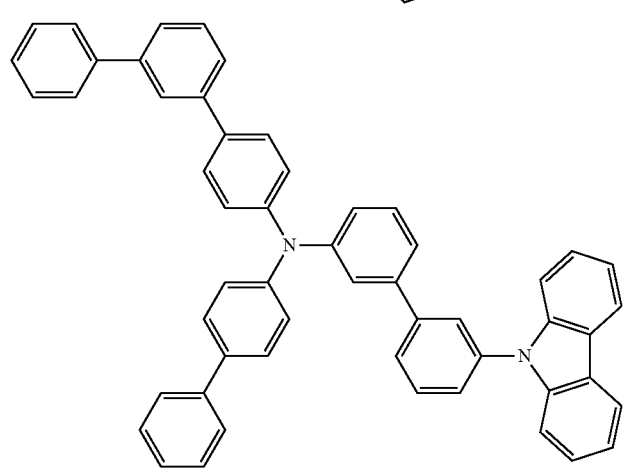

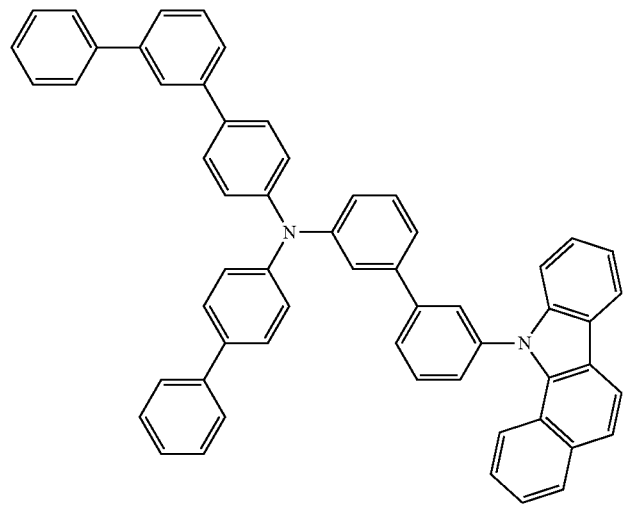
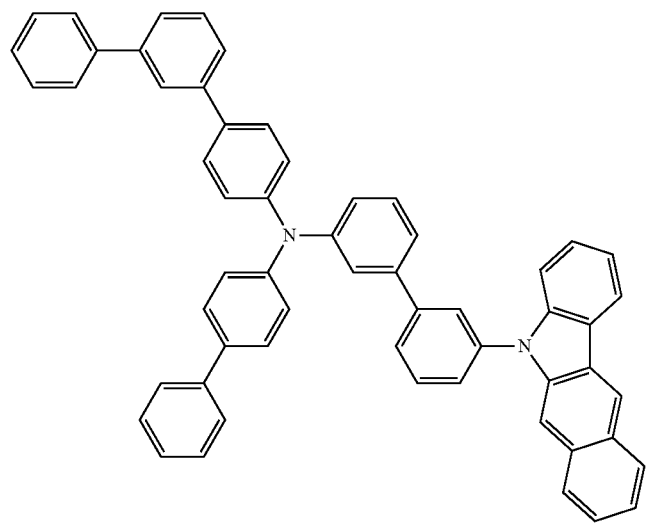
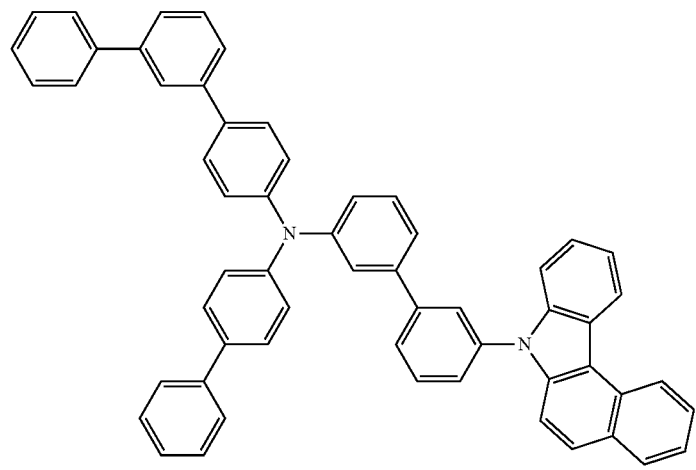

-continued
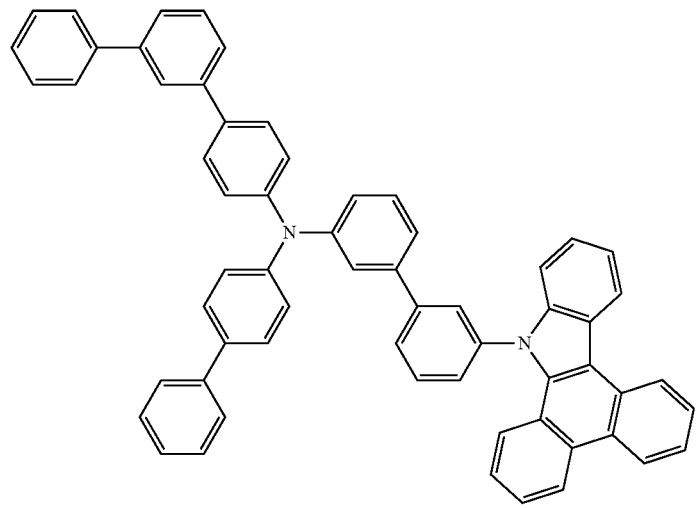
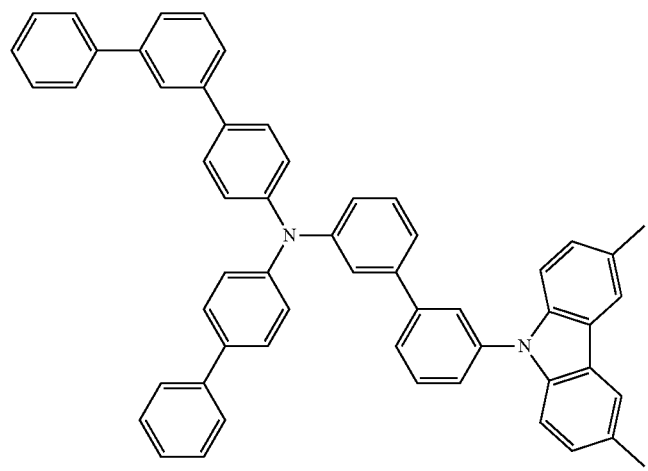
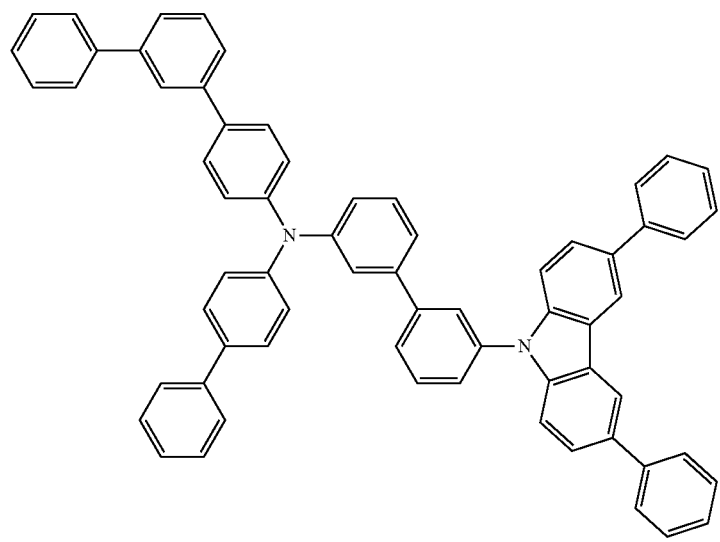

-continued
| 111 | 112 |
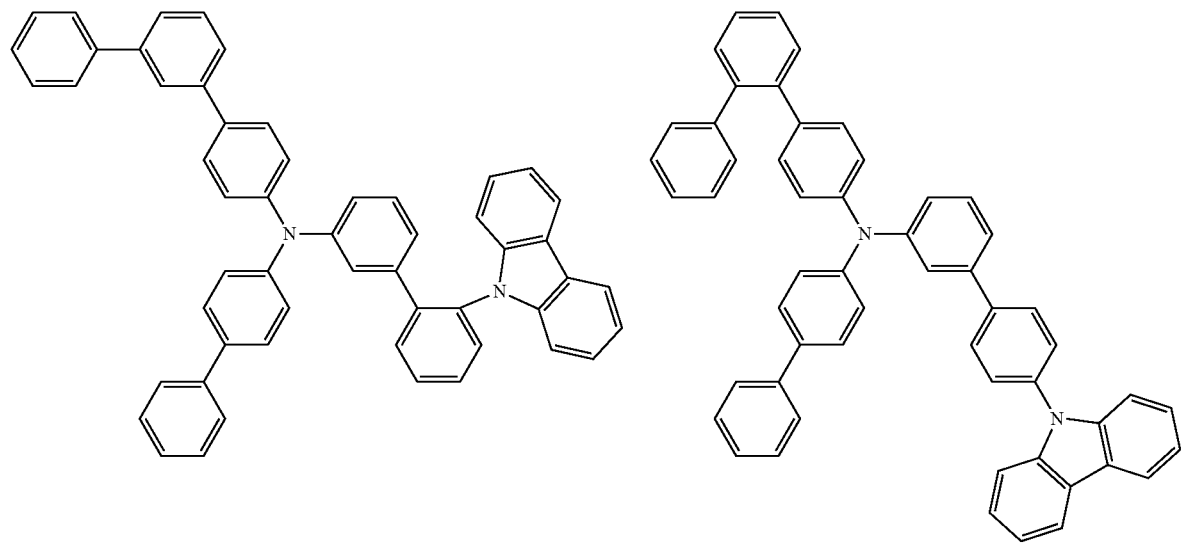
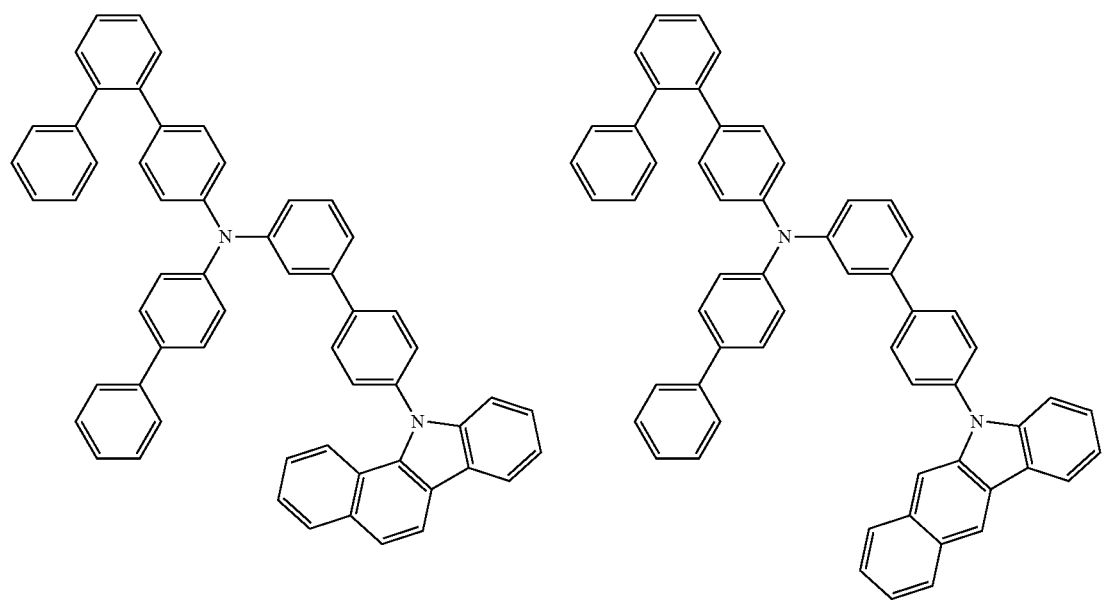

113
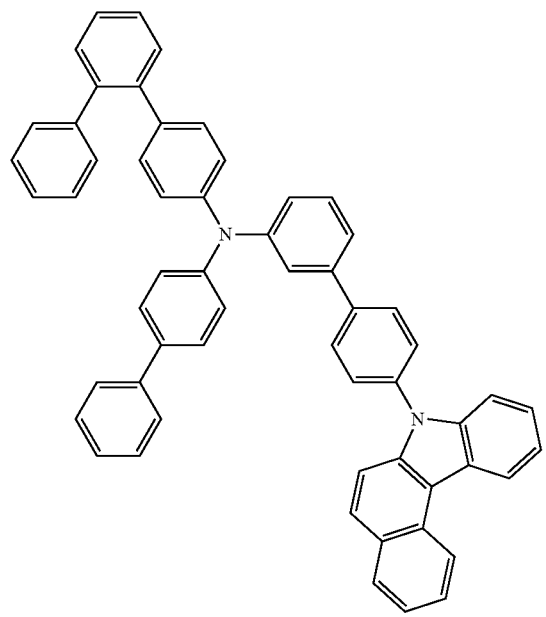
114
-continued
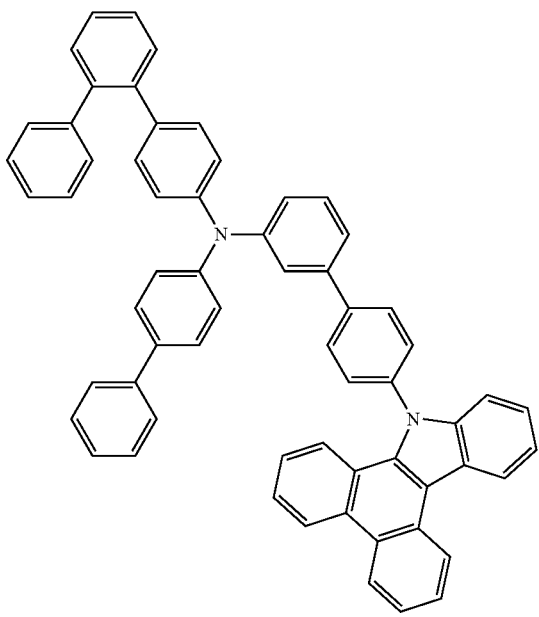
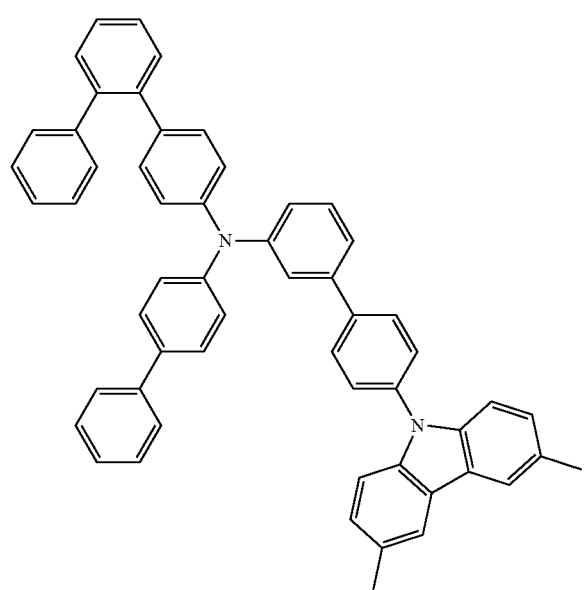

-continued
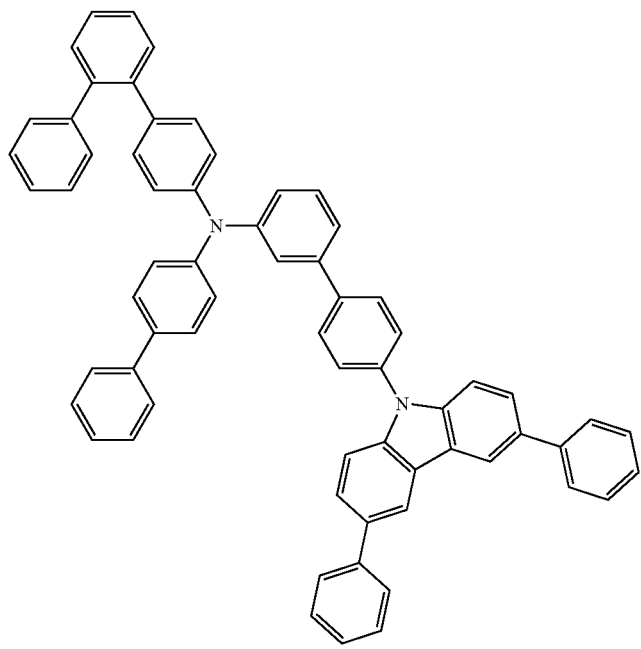
115
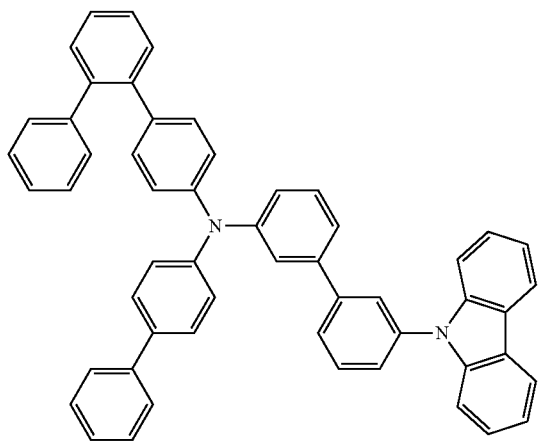
116
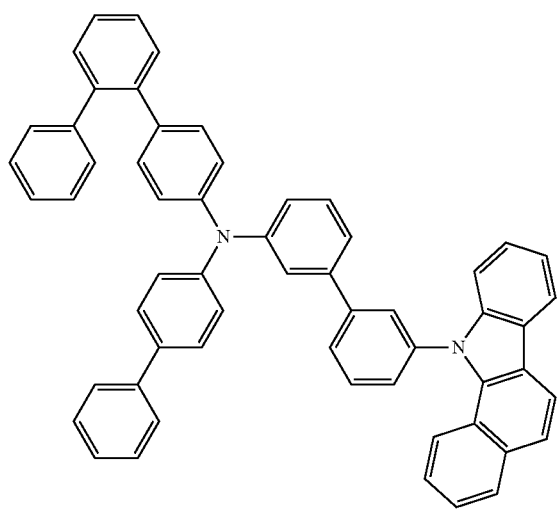
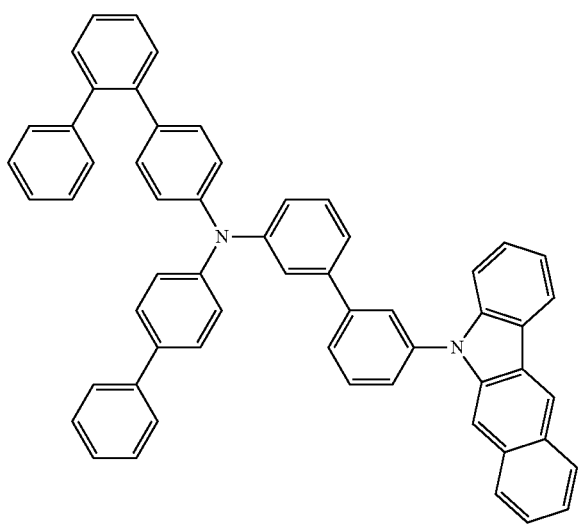
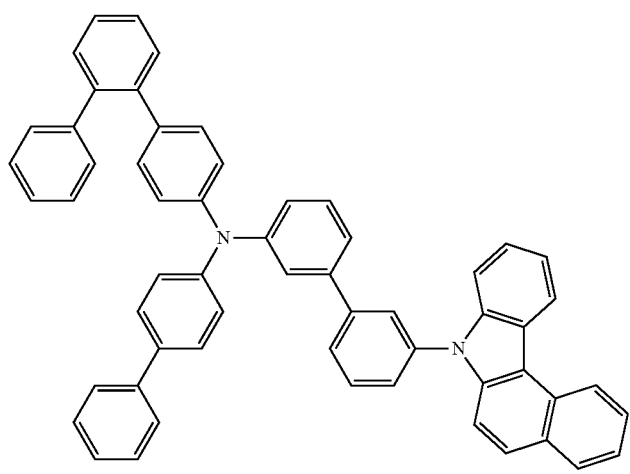

-continued
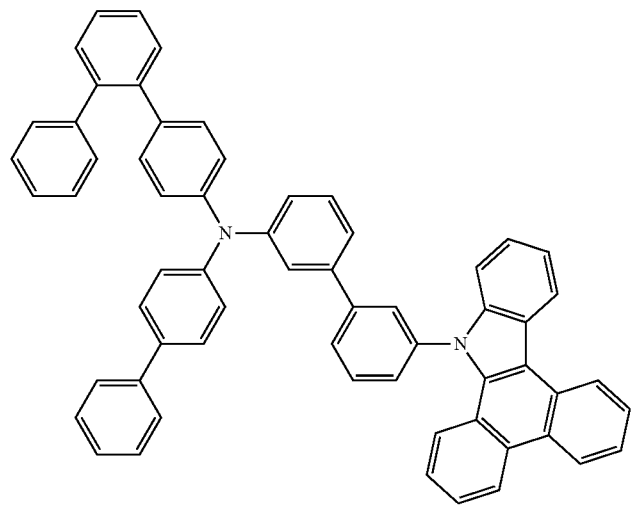
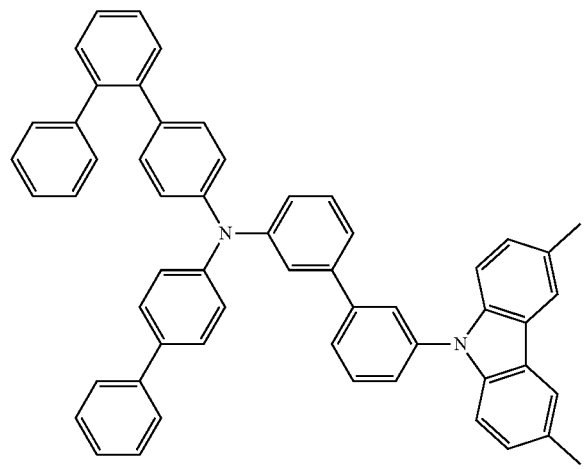
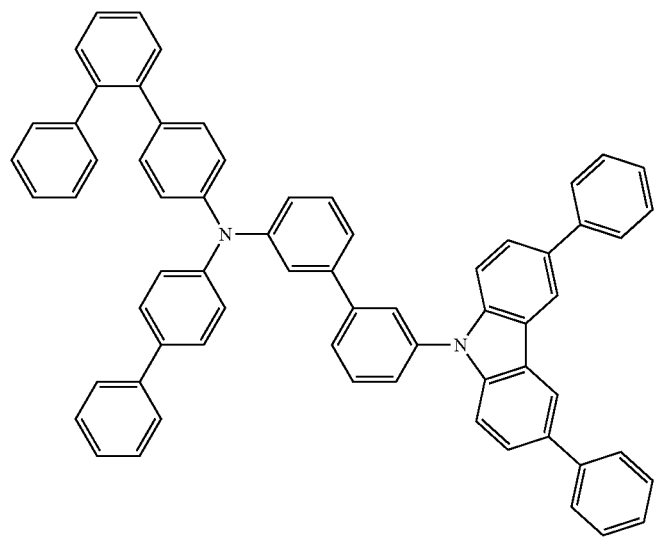

119
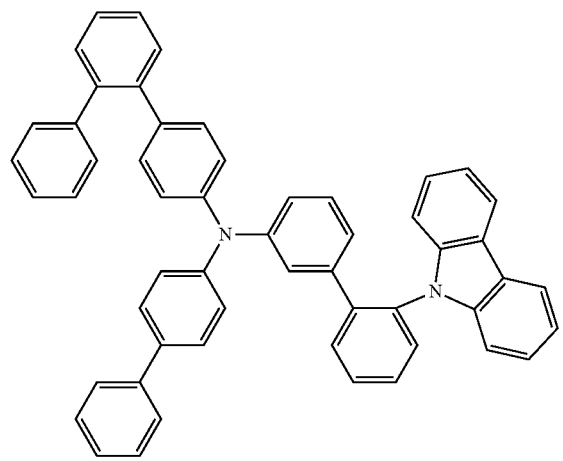
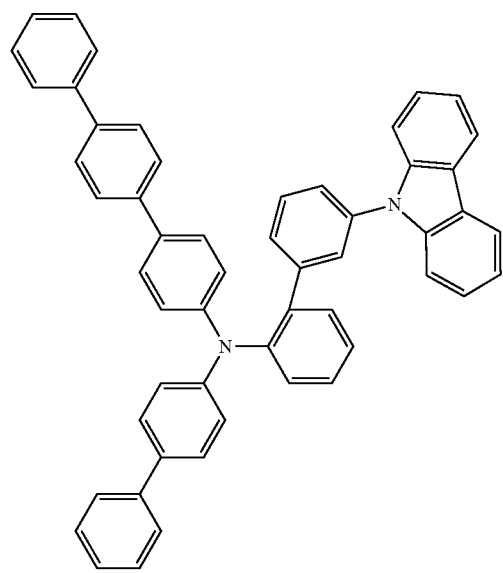
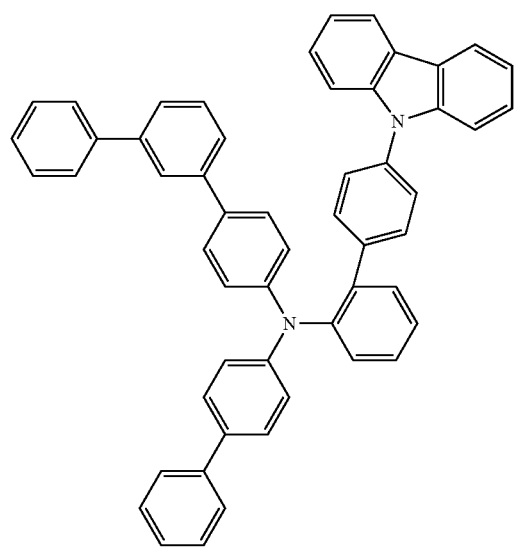
120
-continued
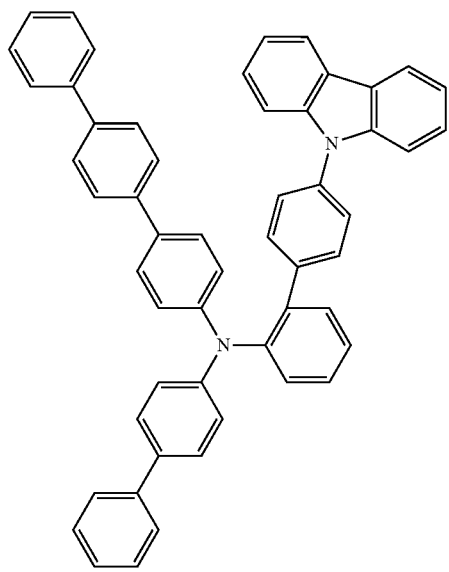
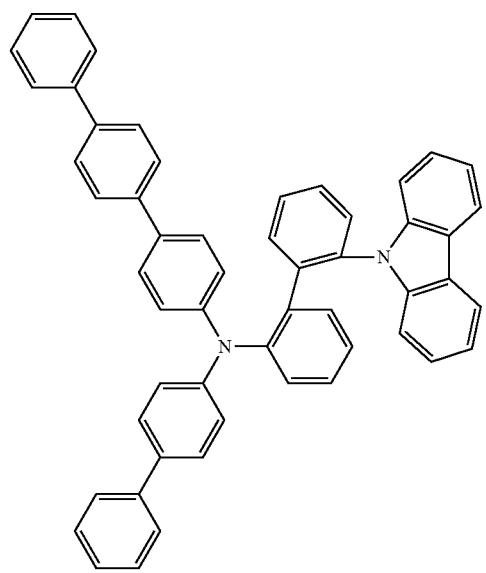
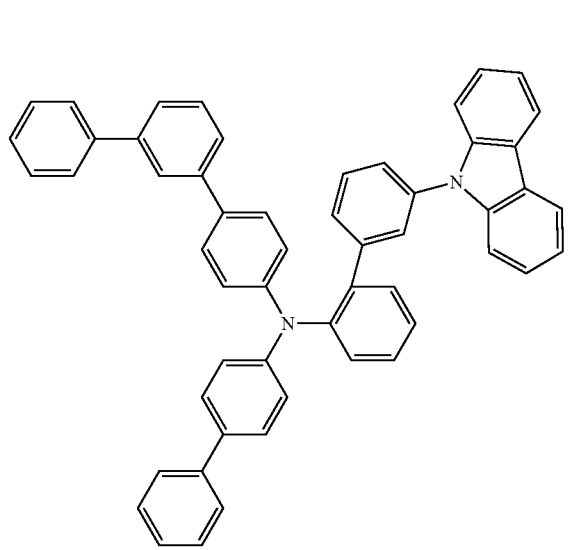

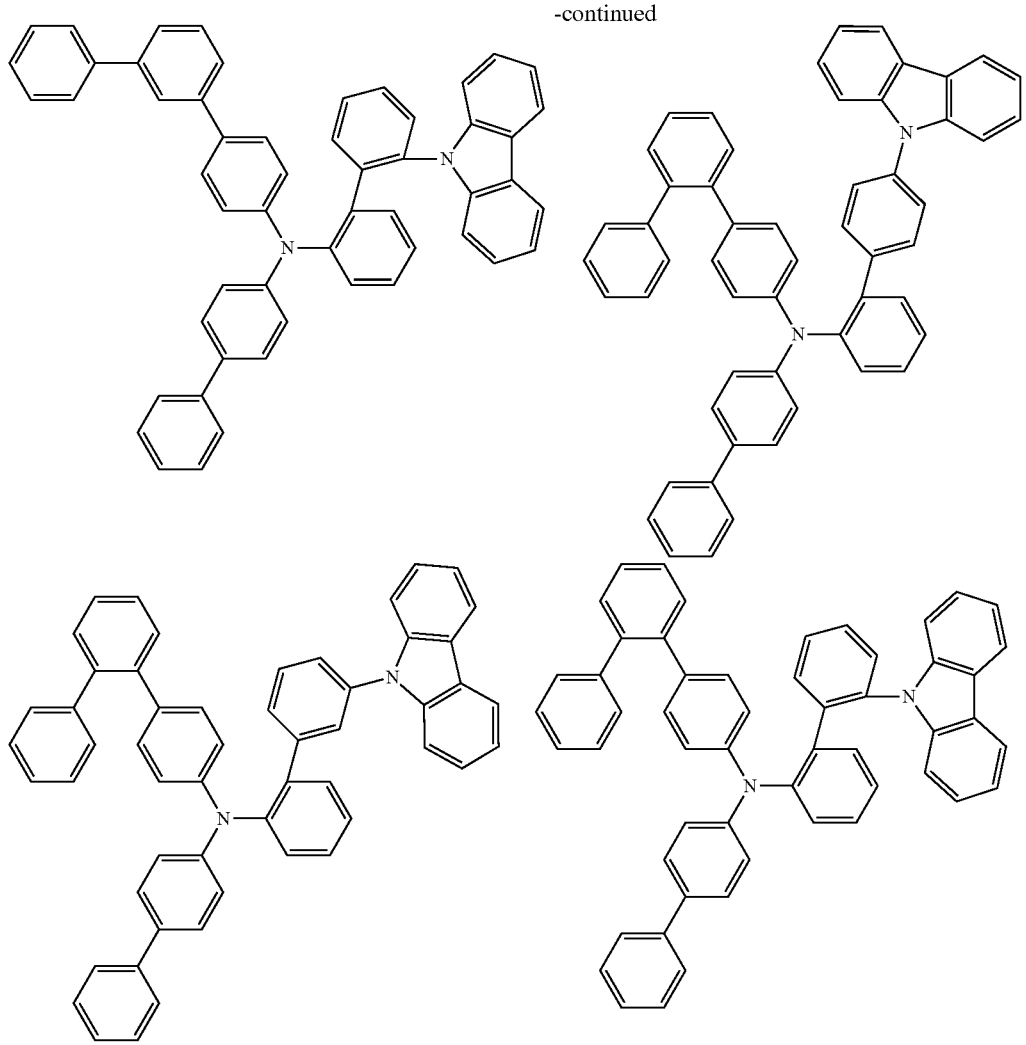

Material for Organic Electroluminescence Devices

The material for organic electroluminescence devices in an aspect of the invention comprises the compound represented by formula (1) (compound (1)). The content of the compound (1) in the material for organic electroluminescence devices is, but not particularly limited, 1% by mass or more (inclusive of 100%), preferably 10% by mass or more (inclusive of 100%), more preferably 50% by mass or more (inclusive of 100%), still more preferably 80% by mass or more (inclusive of 100%), and particularly preferably 90% by mass or more (inclusive of 100%).

The material for organic EL devices is useful as a material for producing an organic EL device and may be used, for example, in a light emitting layer of a fluorescent emission unit as a host material or a dopant material or in a light emitting layer of a phosphorescent emission unit as a host material. In addition, in either a fluorescent emission unit or a phosphorescent emission unit, the material for organic EL device of the invention is also useful as a material for an anode-side organic thin film layer, for example, a hole transporting layer, a hole injecting layer, and an electron blocking layer, which is formed between an anode and a light emitting layer. The anode-side organic thin film layer may be a multilayer comprising two or more layers which may be hole transporting layers. The material for organic EL devices of the invention may be used in any of the two or more hole transporting layers. Thus, the material for organic EL devices of the invention may be used in any of a hole transporting layer closest to a light emitting layer, a hole transporting layer closest to an anode, and a hole transporting layer between them.

Organic Electroluminescence Device

The organic EL device in an aspect of the invention will be described below.

The organic EL device comprises an organic thin film layer between a cathode and an anode. The organic thin film layer comprises one or more layers and a light emitting layer, and at least one layer of the organic thin film layer comprises the compound (1).

Examples of the organic thin film layer which comprises the compound (1) include an anode-side organic thin film layer formed between an anode and a light emitting layer (hole transporting layer, hole injecting layer, electron blocking layer, exciton blocking layer, etc.), a light emitting layer, a space layer, and a blocking layer, although not limited thereto. The compound (1) is usable in a fluorescent emission unit, for example, as a host material or a dopant material in a light emitting layer, a hole injecting layer material, and a hole transporting layer material. The compound (1) is also usable in a phosphorescent emission unit as a host material in a light emitting layer, a hole injecting layer material and a hole transporting layer material. When the anode-side organic thin film layer comprises two or more hole transporting layers, the compound (1) may be included in any of the hole transporting layers. Namely, the compound (1) may be included in any of the hole transporting layer closest to the light emitting layer, the hole transporting layer closest to the anode, and a hole transporting layer between them.

The organic EL device in an aspect of the invention may be any of a fluorescent or phosphorescent single color emitting device, a white-emitting device of fluorescent-phosphorescent hybrid type, a simple-type emitting device having a single emission unit, and a tandem emitting device having two or more emission units, with a fluorescent device being preferred. The "emission unit" referred to herein is the smallest unit for emitting light by the recombination of injected holes and injected electrons, which comprises an organic thin film layer comprising one or more layers, wherein at least one layer is a light emitting layer.

Representative device structures of the simple-type organic EL device are shown below:
(1) Anode/Emission Unit/Cathode The emission unit may be a laminated unit comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the simple-type emission unit are shown below, wherein the layers in parentheses are optional:
(a) (Hole injecting layer/) Hole transporting layer/Fluorescent emitting layer (/Electron transporting layer);
(b) (Hole injecting layer/) Hole transporting layer/First phosphorescent (fluorescent) emitting layer/Second phosphorescent (fluorescent) emitting layer (/Electron transporting layer);
(c) (Hole injecting layer/) Hole transporting layer/Phosphorescent emitting layer/Space layer/Fluorescent emitting layer (/Electron transporting layer);
(d) (Hole injecting layer/) Hole transporting layer/First phosphorescent emitting layer/Second phosphorescent emitting layer/Space layer/Fluorescent emitting layer (/Electron transporting layer);
(e) (Hole injecting layer/) Hole transporting layer/First phosphorescent emitting layer/Space layer/Second phosphorescent emitting layer/Space layer/Fluorescent emitting layer (/Electron transporting layer);
(f) (Hole injecting layer/) Hole transporting layer/Phosphorescent emitting layer/Space layer/First fluorescent emitting layer/Second fluorescent emitting layer (/Electron transporting layer);
(g) (Hole injecting layer/) Hole transporting layer/Electron blocking layer/Fluorescent emitting layer (/Electron transporting layer);
(h) (Hole injecting layer/) Hole transporting layer/Electron blocking layer/Phosphorescent emitting layer (/Electron transporting layer);
(i) (Hole injecting layer/) Hole transporting layer/Exciton blocking layer/Fluorescent emitting layer (/Electron transporting layer);
(j) (Hole injecting layer/) Hole transporting layer/Exciton blocking layer/Phosphorescent emitting layer (/Electron transporting layer);
(k) (Hole injecting layer/) First hole transporting layer/Second hole transporting layer/Fluorescent emitting layer (/Electron transporting layer);
(l) (Hole injecting layer/) First hole transporting layer/Second hole transporting layer/Phosphorescent emitting layer (/Electron transporting layer);
(m) (Hole injecting layer/) Hole transporting layer/Fluorescent emitting layer/Hole blocking layer (/Electron transporting layer); and
(n) (Hole injecting layer/) Hole transporting layer/Fluorescent emitting layer/Triplet blocking layer (/Electron transporting layer).

The emission color of the fluorescent emitting layer and that of the phosphorescent emitting layer may be different. For example, the layered structure of the laminated emission unit (d) may be (Hole injecting layer/) Hole transporting layer/First phosphorescent emitting layer (red emission)/Second phosphorescent emitting layer (green emission)/Space layer/Fluorescent emitting layer (blue emission)/Electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such an electron blocking layer or a hole blocking layer, electrons and holes are confined in the light emitting layer to increase the charge recombination in the light emitting layer, thereby improving the emission efficiency.

Representative device structure of the tandem-type organic EL device is shown below:
(2) Anode/First Emission Unit/Intermediate Layer/Second Emission Unit/Cathode.

The layerd structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials which can supply electrons to the first emission unit and holes to the second emission unit.

A schematic structure of an example of the organic EL device is shown in FIG. 1, wherein the organic EL device 1 comprises a substrate 2, an anode 3, a cathode 4, and an emission unit 10 disposed between the anode 3 and the cathode 4. The emission unit 10 comprises a light emitting layer 5. A hole injecting layer or a hole transporting layer 6 (anode-side organic thin film layer) may be disposed between the light emitting layer 5 and the anode 3, and an electron injecting layer or a electron transporting layer 7 (cathode-side organic thin film layer) may be disposed between the light emitting layer 5 and the cathode 4. An electron blocking layer (not shown) may be disposed on the side of anode 3 of the light emitting layer 5, and a hole blocking layer (not shown) may be disposed on the side of cathode 4 of the light emitting layer 5. With these blocking layers, electrons and holes are confined in the light emitting layer 5 to increase the exciton generation in the light emitting layer 5.

In the present specification, a host is referred to as a fluorescent host when combinedly used with a fluorescent dopant (fluorescent emitting material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be utilized as a material for a fluorescent emitting layer. The same applies to the fluorescent host.

Substrate

The substrate is a support for the emitting device and made of, for example, glass, quartz, and plastics. The substrate may be a flexible substrate, for example, a plastic substrate made of polycarbonate, polyarylate, polyether sulfone, polypropylene, polyester, polyvinyl fluoride, or polyvinyl chloride. An inorganic deposition film is also usable.

Anode

The anode is formed on the substrate preferably from a metal, an alloy, an electrically conductive compound, and a mixture thereof, each having a large work function, for example, 4.0 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo), iron (Fe), cobalt (Co), copper (Cu), palladium (Pd), titanium (Ti), and a nitride of the above metal (for example, titanium nitride) are also usable.

These materials are made into a film generally by a sputtering method. For example, a film of indium oxide-zinc oxide is formed by sputtering an indium oxide target doped with 1 to 10 wt % of zinc oxide, and a film of indium oxide doped with tungsten oxide and zinc oxide is formed by sputtering an indium oxide target doped with 0.5 to 5 wt % of tungsten oxide and 0.1 to 1 wt % of zinc oxide. In addition, a vacuum vapor deposition method, a coating method, an inkjet method, and a spin coating method are usable.

A hole injecting layer to be optionally formed in contact with the anode is formed from a material which is capable of easily injecting holes independently of the work function of the anode. Therefore, the anode can be formed by a material generally known as an electrode material, for example, a metal, an alloy, an electroconductive compound, a mixture thereof, and a group 1 element and a group 2 element of the periodic table.

A material having a small work function, for example, the group 1 element and the group 2 element of the periodic table, i.e., an alkali metal, such as lithium (Li) and cesium (Cs), an alkaline earth metal, such as magnesium (Mg), calcium (Ca), and strontium (Sr), and an alloy thereof, such as MgAg and AlLi, are also usable. In addition, a rare earth metal, such as europium (Eu) and ytterbium (Yb), and an alloy thereof are also usable. The alkali metal, the alkaline earth metal, and the alloy thereof can be made into the anode by a vacuum vapor deposition or a sputtering method. When a silver paste, etc. is used, a coating method and an inkjet method are usable.

Hole Injecting Layer

The hole injecting layer comprises a highly hole injecting material (hole injecting material). The compound (1) is usable in the hole injecting layer alone or in combination of the material mentioned below.

Examples of the hole injecting material include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable as the hole injecting material: 4,4',4"-tris(N,N-diphenylamino)triphenylamine (TDATA), 4,4',4"-tris[N-(3-methylphenyl)-N-phenylamino]triphenylamine (MTDATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino) biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis[N-(9-phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1).

A macromolecular compound, such as an oligomer, a dendrimer, a polymer, is also usable. Examples thereof include poly(N-vinylcarbazole) (PVK), poly(4-vinyltriphenylamine) (PVTPA), poly[N-(4-{N'-[4-(4-diphenylamino) phenyl]phenyl-N'-phenylamino}phenyl)methacrylamide] (PTPDMA), and poly[N,N'-bis(4-butylphenyl)-N,N'-bis (phenyl)benzidine] (Poly-TPD). An acid-added macromolecular compound, such as poly(3,4-ethylenedioxythiophene)/poly(styrenesulfonic acid) (PEDOT/PSS) and polyaniline/poly(styrenesulfonic acid) (PAni/PSS), is also usable.

In addition, an acceptor material, such as a hexaazatriphenylene (HAT) compound represented by formula (K), is preferably used in combination with the compound (1):

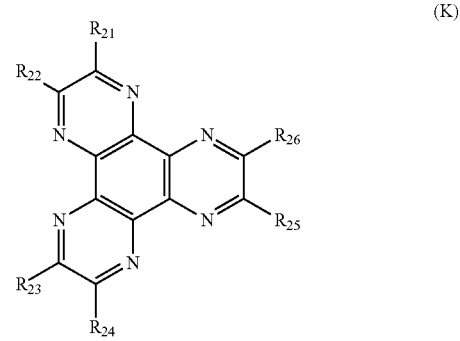

(K)

wherein $R_{21}$ to $R_{26}$ may be the same or different and each of $R_{21}$ to $R_{26}$ is independently a cyano group, —$CONH_2$, a carboxyl group, or —$COOR_{27}$ wherein $R_{27}$ is an alkyl group having 1 to 20 carbon atoms or a cycloalkyl group having 3 to 20 carbon atoms, or adjacent two, i.e., $R_{21}$ and $R_{22}$, $R_{23}$ and $R_{24}$, and $R_{25}$ and $R_{26}$ may be bonded to each other to form a group represented by —CO—O—CO—.

Examples of $R_{27}$ include a methyl group, an ethyl group, a n-propyl group, an isopropyl group, a n-butyl group, an isobutyl group, a t-butyl group, a cyclopentyl group, and a cyclohexyl group.

Hole Transporting Layer

The hole transporting layer comprises a highly hole transporting material (hole transporting material). The compound (1) is preferably used in the hole transporting layer alone or in combination with the compound mentioned below.

Examples of the hole transporting material include an aromatic amine compound, a carbazole derivative, and an anthracene derivative. Examples of the aromatic amine compound are 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluorene-9-yl)triphenylamine (BAFLP), 4,4'-bis[N-(9,9- dimethylfluorene-2-yl)-N-phenylamino]biphenyl (DFLDPBi), 4,4',4''-tris(N,N-diphenylamino)triphenylamine (TDATA), 4,4',4''-tris[N-(3-methylphenyl)-N-phenylamino]triphenylamine (MTDATA), and 4,4'-bis[N-(spiro-9,9'-bifluorene-2-yl)-N-phenylamino]biphenyl (BSPB). The above compounds have a hole mobility of $10^{-6}$ cm$^2$/Vs or more.

The hole transporting layer may comprise a carbazole derivative, such as 4,4'-di(9-carbazolyl)biphenyl (CBP), 9-[4-(9-carbazolyl)phenyl]-10-phenylanthracene (CzPA), and 9-phenyl-3-[4-(10-phenyl-9-anthryl)phenyl]-9H-carbazole (PCzPA); an anthracene derivative, such as 2-t-butyl-9,10-di(2-naphthyl)anthracene (t-BuDNA), 9,10-di(2-naphthyl)anthracene (DNA), and 9,10-diphenylanthracene (DPAnth); and a macromolecular compound, such as poly(N-vinylcarbazole) (PVK) and poly(4-vinyltriphenylamine) (PVTPA).

Compounds other than those mentioned above are also usable if their hole transporting ability is higher than their electron transporting ability. The layer comprising a highly hole-transporting material may be a single layer or a laminate of two or more layers each comprising the compound mentioned above. For example, the hole transporting layer may be a two-layered structure of a first hole transporting layer (anode side) and a second hole transporting layer (cathode side). In this case, the compound (1) may be used in either of the first hole transporting layer and the second hole transporting layer. In an embodiment of the invention, the compound (1) is preferably used in the first hole transporting layer. In another embodiment of the invention, the compound (1) is preferably used in the second hole transporting layer.

Dopant Material of Light Emitting Layer

The light emitting layer comprises a highly light-emitting material (dopant material) and may be formed from a various kind of materials. For example, a fluorescent emitting material and a phosphorescent emitting material are usable as the dopant material. The fluorescent emitting material is a compound capable of emitting light from a singlet excited state, and the phosphorescent emitting material is a compound capable of emitting light from a triplet excited state.

Examples of blue fluorescent emitting material for use in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9yl)-4'-(10-phenyl-9-anthryl)triphenylamine (YGAPA), and 4-(10-phenyl-9-anthryl)-4'-(9-phenyl-9H-carbazole-3-yl)triphenylamine (PCBAPA).

Examples of green fluorescent emitting material for use in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material for use in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material for use in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIr$_6$), bis[2-(4',6'-difluorophenyl)pyridinato-N,C2'] iridium(III) picolinato (FIrpic), bis[2-(3',5'-bistrifluoromethylphenyl)pyrithnato-N,C2']iridium (III) picolinato ar(CF$_3$ppy)$_2$(pic)), and bis[2-(4',6'-difluorophenyl)pyridinato-N,C2']iridium(III) acetylacetonato (FIracac).

Examples of green phosphorescent emitting material for use in the light emitting layer include an iridium complex, such as tris(2-phenylpyridinato-N,C2')iridium(III) (Ir(ppy)$_3$), bis(2-phenylpyridinato-N,C2')iridium(III) acetylacetonato (Ir(ppy)$_2$(acac)), bis(1,2-diphenyl-1H-benzimidazolato)iridium(III) acetylacetonato (Ir(pbi)$_2$(acac)), and bis(benzo[h]quinolinato)iridium(III) acetylacetonato (Ir(bzq)$_2$(acac)).

Examples of red phosphorescent emitting material for use in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato (Ir(btp)$_2$(acac)), bis(1-phenylisoquinolinato-N,C2')iridium(III) acetylacetonato (Ir(piq)$_2$(acac)), (acetylacetonato)bis[2,3 -bis(4-fluorophenyl)quinoxalinato]iridium(III) (Ir(Fdpq)$_2$(acac)), and 2,3,7,8,12,13,17,18-octaethyl-21H,23H-porphyrin platinum(II) (PtOEP).

Examples of red phosphorescent emitting material for use in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato (Ir(btp)$_2$(acac)), bis(1-phenylisoquinolinato-N,C2')iridium(III) acetylacetonato (Ir(piq)$_2$(acac)), (acetylacetonato)bis[2,3 -bis(4-fluorophenyl)quinoxalinato]iridium(III) (Ir(Fdpq)$_2$(acac)), and 2,3,7,8,12,13,17,18-octaethyl-21H,23H-porphyrin platinum(II) (PtOEP).

A rare earth metal complex, such as tris(acetylacetonato)(monophenanthroline)terbium(III) (Tb(acac)$_3$(Phen)), tris(1,3-diphenyl-1,3-propanedionato)(monophenanthroline)europium (III) (Eu(DBM)$_3$(Phen)), and tris [1-(2-thenoyl)-3,3,3-trifluoro acetonato](monophenanthroline)europium(III) (Eu(TTA)$_3$(Phen)), emits light from the rare earth metal ion (electron transition between different multiple states), and therefore, usable as a phosphorescent emitting compound.

Host Material for Light Emitting Layer

The light emitting layer may be formed by dispersing the dopant material mentioned above in another material (host material). The host material preferably has a lowest unoccupied molecular orbital level (LUMO level) higher than that of the dopant material and a highest occupied molecular orbital level (HOMO level) lower than that of the dopant material.

The host material may include, for example, (1) a metal complex, such as an aluminum complex, a beryllium complex, and a zinc complex;
(2) a heterocyclic compound, such as an oxadiazole derivative, a benzimidazole derivative, and a phenanthroline derivative;
(3) a fused aromatic compound, such as a carbazole derivative, an anthracene derivative, a phenanthrene derivative, a pyrene derivative, and a chrysene derivative; and (4) an aromatic amine compound, such as a triarylamine derivative and a fused aromatic polycyclic amine derivative.

Examples thereof include:

a metal complex, such as tris(8-quinolinolato)aluminum (III) (Alq), tris(4-methyl-8-quinolinolato)aluminum(III) (Almq$_3$), bis(10-hydroxybenzo[h]quinolinato)beryllium(II) (BeBq$_2$), bis(2-methyl-8-quinolinolato)(4-phenylphenolato)aluminum(III) (BAlq), bis(8-quinolinolato)zinc(II) (Znq), bis[2-(2-benzoxazolyl)phenolato]zinc(II) (ZnPBO), and bis[2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2''-(1,3,5-benzenetriyl)tris(1-phenyl-1H-benzimidazole) (TPBI), bathophenanthroline (BPhen), and bathocuproin (BCP);

a fused aromatic compound, such as 9-[4(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3''-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), 4,4'-bis[N-(1-anthryl)-N-phenylamino]biphenyl (NPB or α-NPD), N,N'-bis(3-methylphenyl)-N,N'-diphenyl-[1,1'-biphenyl]-4,4'-diamine (TPD), 4,4'-bis[N-(9,9-dimethylfluoren-2-yl)-N-phenylamino]biphenyl (DFLDPBi), and 4,4'-bis[N-(spiro-9,9'-bifluorene-2-yl)-N-phenylamino]biphenyl (BSPB). The host material may be used alone or in combination of two or more.

Electron Transporting Layer

The electron transporting layer comprises a highly electron-transporting material (electron transporting material). Examples thereof are:

(1) a metal complex, such as an aluminum complex, a beryllium complex, and a zinc complex;
(2) a heteroaromatic compound, such as an imidazole derivative, a benzimidazole derivative, an azine derivative, a carbazole derivative, and a phenanthroline derivative; and
(3) a macromolecular compound.

Examples of the metal complex include tris(8-quinolinolato)aluminum (III) (Alq), tris(4-methyl-8-quinolinolato)aluminum (Almq$_3$), bis(10-hydroxybenzo[h]quinolinato)beryllium (BeBq$_2$), bis(2-methyl-8-quinolinato)(4-phenylphenolato)aluminum (III) (BAlq), bis(8-quinolinato)zinc(II) (Znq), bis[2-(2-benzoxazolyl)phenolato]zinc(II) (ZnPBO), and bis[2-(2-benzothiazolyl)phenolato]zinc(II) (ZnBTZ).

Examples of the heteroaromatic compound include 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs).

Examples of the macromolecular compound include poly[(9,9-dihexylfluorene-2,7-diyl)-co-(pyridine-3,5-diyl)] (PF-Py), and poly[(9,9-dioctylfluorene-2,7-diyl)-co-(2,2'-bipyridine-6,6'-diyl)] (PF-BPy).

The above compounds have an electron mobility of mainly $10^{-6}$ cm$^2$/Vs or more. Materials other than those mentioned above are also usable in the electron transporting layer if their electron transporting ability is higher than their hole transporting ability. The electron transporting layer may be a single layer or a laminate of two or more layers each comprising the material mentioned above.

Electron Injecting Layer

The electron injecting layer comprises a highly electron-injecting material, for example, an alkali metal, an alkaline earth metal, and a compound of these metals, such as lithium (Li), cesium (Cs), calcium (Ca), lithium fluoride (LiF), cesium fluoride (CsF), calcium fluoride(CaF2), and lithium oxide (LiOx). In addition, an electron transporting material which is doped with an alkali metal, an alkaline earth metal or a compound thereof, for example, Alq doped with magnesium (Mg), is also usable. By using such a material, electrons are efficiently injected from the cathode.

A composite material obtained by mixing an organic compound and an electron donor is also usable in the electron injecting layer. Such a composite material is excellent in the electron injecting ability and the electron transporting ability, because the organic compound receives electrons from the electron donor. The organic compound is preferably a material excellent in transporting the received electrons. Examples thereof are the materials for the electron transporting layer mentioned above, such as the metal complex and the aromatic heterocyclic compound. Any material capable of giving its electron to another organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include a metal of the group 1 or 2 of the periodic table, for example, an alkali metal, such as lithium (Li) and cesium (Cs), an alkaline earth metal, such as magnesium (Mg), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof can be made into the cathode by a vacuum vapor deposition or a sputtering method. When a silver paste, etc. is used, a coating method and an inkjet method are usable.

When the electron injecting layer is formed, the material for the cathode can be selected independently from the work function and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Insulating Layer

Since electric field is applied to the ultra-thin films of organic EL devices, the pixel defects due to leak and short circuit tends to occur. To prevent the defects, an insulating thin film layer is preferably interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be made into laminated layers.

Space Layer

For example, in an organic EL device wherein a fluorescent emitting layer and a phosphorescent emitting layer are laminated, a space layer is disposed between the fluorescent emitting layer and the phosphorescent emitting layer to prevent the diffusion of excitons generated in the phosphorescent emitting layer to the fluorescent emitting layer or to control the carrier balance. The space layer may be disposed between two or more phosphorescent emitting layers.

Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

In the organic EL device, a blocking layer, such as an electron blocking layer, a hole blocking layer, and a triplet blocking layer, may be provided in the portion adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The triplet blocking layer prevents the diffusion of excitons generated in the light emitting layer to adjacent layers and has a function of confining the excitons in the light emitting layer. The compound (1) of the invention is also suitable as the material for the electron blocking layer and the triplet blocking layer.

Each layer of the organic EL device can be formed by a known method, such as a vapor deposition method and a coating method. For example, each layer can be formed by a known vapor deposition method, such as a vacuum vapor deposition method and a molecular beam evaporation method (MBE method), and a known coating method using a solution of the compound for forming the layer, such as a dipping method, a spin coating method, a casting method, a bar coating method, and a roll coating method.

The thickness of each layer is not particularly limited and preferably 5 nm to 10 μm, more preferably 10 nm to 0.2 μm, because an excessively small thickness may cause defects such as pin holes and an excessively large thickness may require a high driving voltage.

The organic EL device can be used in an electronic device, for example, as display parts, such as organic EL panel module, display devices of television sets, mobile phones, personal computer, etc., and light emitting sources of lighting equipment and vehicle lighting equipment.

EXAMPLES

The invention will be described in more detail with reference to the examples. It should be noted that the scope of the invention is not limited to the following examples.

Intermediate Synthesis 1 (Synthesis of Intermediate 1)

Under argon atmosphere, into a mixture of 32.4 g (100.0 mmol) of N-(4-bromophenyl)-4-phenylaniline, 30.1 g (105.0 mmol) of 4-(carbazole-9-yl)phenylboronic acid, and 2.31 g (2.00 mmol) of $Pd[PPh_3]_4$, 150 ml of toluene, 150 ml of dimethoxyethane, and 150 ml (300.0 mmol) of a 2 M aqueous solution of $Na_2CO_3$ were added. The resultant mixture was stirred for 10 h by refluxing under heating.

After the reaction, the reaction liquid was cooled to room temperature and extracted with dichloromethane in a separating funnel. The organic layer was dried over $MgSO_4$, filtered, and then concentrated. The residue was purified by silica gel column chromatography to obtain 34.5 g of a white solid, which was identified as the following intermediate 1 by FD-MS analysis (field desorption mass spectrometry) (yield: 71%).

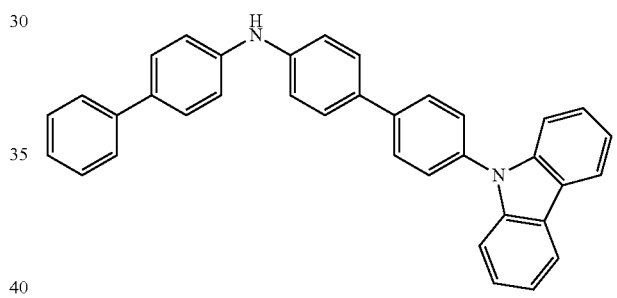

Intermediat 1

Intermediate Synthesis 2 (Synthesis of Intermediate 2)

The procedures of Intermediate Synthesis 1 were repeated except for using 30.1 g of 3-(carbazole-9-yl)phenylboronic acid in place of 4-(carbazole-9-yl)phenylboronic acid to obtain 32.3 g of a white solid, which was identified as the following intermediate 2 by FD-MS analysis (yield: 66%).

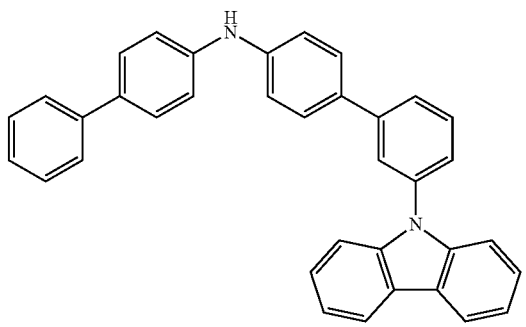

Intermediate 2

Synthesis Example 1 (Synthesis of Aromatic Amine Derivative (H1))

Under argon atmosphere, into a mixture of 3.1 g (10.0 mmol) of 4-bromo-1,1':4',1"-terphenyl, 4.9 g (10.0 mmol) of the intermediate 1, 0.14 g (0.15 mmol) of Pd$_2$(dba)$_3$, 0.087 g (0.3 mmol) of P(tBu)$_3$HBF$_4$, and 1.9 g (20.0 mmol) of sodium t-butoxide, 50 ml of anhydrous xylene was added. The resultant mixture was refluxed for 8 h under heating.

After the reaction, the reaction liquid was cooled to 50° C. and filtered through celite/silica gel. The filtrate was concentrated and the obtained residue was purified by silica gel column chromatography to obtain a white solid. The crude product was recrystallized from toluene to obtain 2.5 g of a white crystal, which was identified as the following aromatic amine derivative (H1) by FD-MS analysis (yield: 35%).

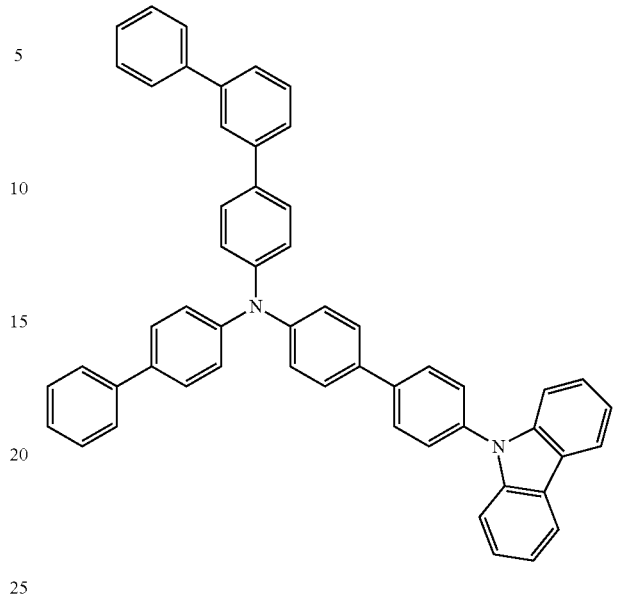

H2

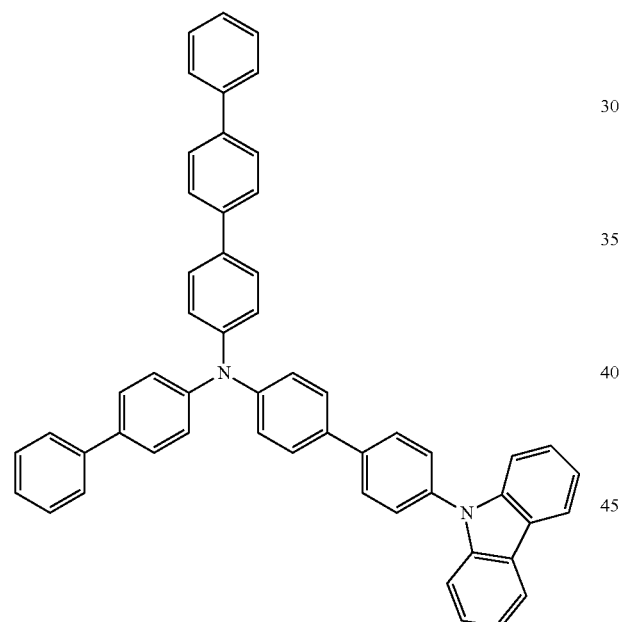

H1

Synthesis Example 2 (Synthesis of Aromatic Amine Derivative (H2))

The procedures of Synthesis Example 1 were repeated except for using 3.1 g of 4-bromo-1,1':3',1"-terphenyl in place of 4-bromo-1,1':4',1"-terphenyl to obtain 2.1 g of a white crystal, which was identified as the following aromatic amine derivative (H2) by FD-MS analysis (yield: 30%).

Synthesis Example 3 (Synthesis of Aromatic Amine Derivative (H3))

The procedures of Synthesis Example 1 were repeated except for using 4.9 g of the intermediate 2 in place of the intermediate 1 to obtain 2.0 g of a white crystal, which was identified as the following aromatic amine derivative (H3) by FD-MS analysis (yield: 28%).

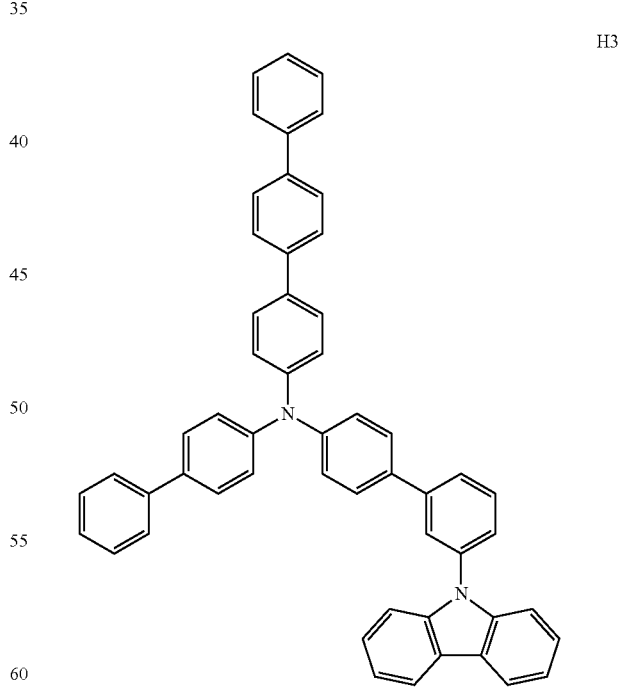

H3

Synthesis Example 4 (Synthesis of Aromatic Amine Derivative (H4))

The procedures of Synthesis Example 1 were repeated except for using 3.1 g of 4-bromo-1,1':3',1"-in place of 4-bromo-1,1':4',1''-terphenyl and using 4.9 g of the intermediate 2 in place of the intermediate 1 to obtain 1.8 g of a white crystal, which was identified as the following aromatic amine derivative (H4) by FD-MS analysis (yield: 25%).

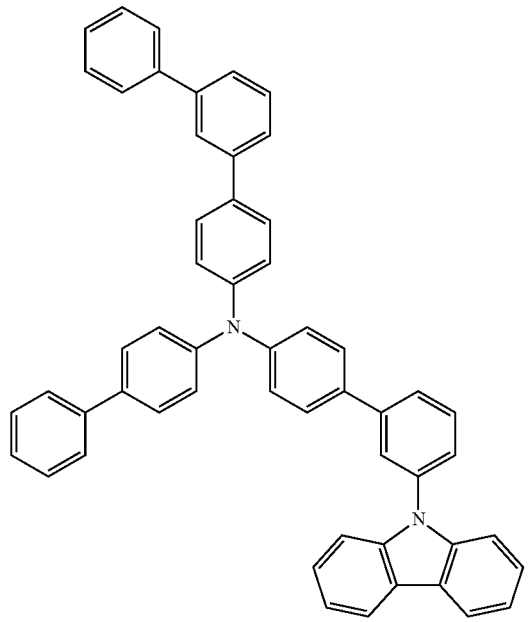

H4

Example 1

Production of Organic EL Device

A glass substrate of 25 mm×75 mm×1.1 mm thick having ITO transparent electrode (product of Geomatec Company) was ultrasonically cleaned in isopropyl alcohol for 5 min and then UV (Ultraviolet)/ozone cleaned for 30 min.

The cleaned glass substrate having a transparent electrode line was mounted to a substrate holder of a vacuum vapor deposition apparatus. First, the electron accepting compound (A) was vapor-deposited so as to cover the transparent electrode to form a film A with a thickness of 5 nm.

On the film A, the aromatic amine derivative (X1) (first hole transporting material) was vapor-deposited to form a first hole transporting layer with a thickness of 80 nm. Successively after forming the first hole transporting layer, the aromatic amine derivative (H1) (second hole transporting material) was vapor-deposited to form a second hole transporting layer with a thickness of 10 nm.

On the hole transporting layer, the host compound (BH) and the dopant compound (BD) were vapor co-deposited to form a light emitting layer with a thickness of 25 nm. The concentration of the dopant compound (BD) was 4% by mass.

On the light emitting layer, the compound (ET1) was vapor-deposited into a thickness of 10 nm, then the compound (ET2) was vapor-deposited into a thickness of 15 nm, and LiF was vapor-deposited into a thickness of 1 nm to form an electron transporting/injecting layer. Thereafter, metallic Al was vapor-deposited into a thickness of 80 nm to form a cathode, thereby producing an organic EL device.

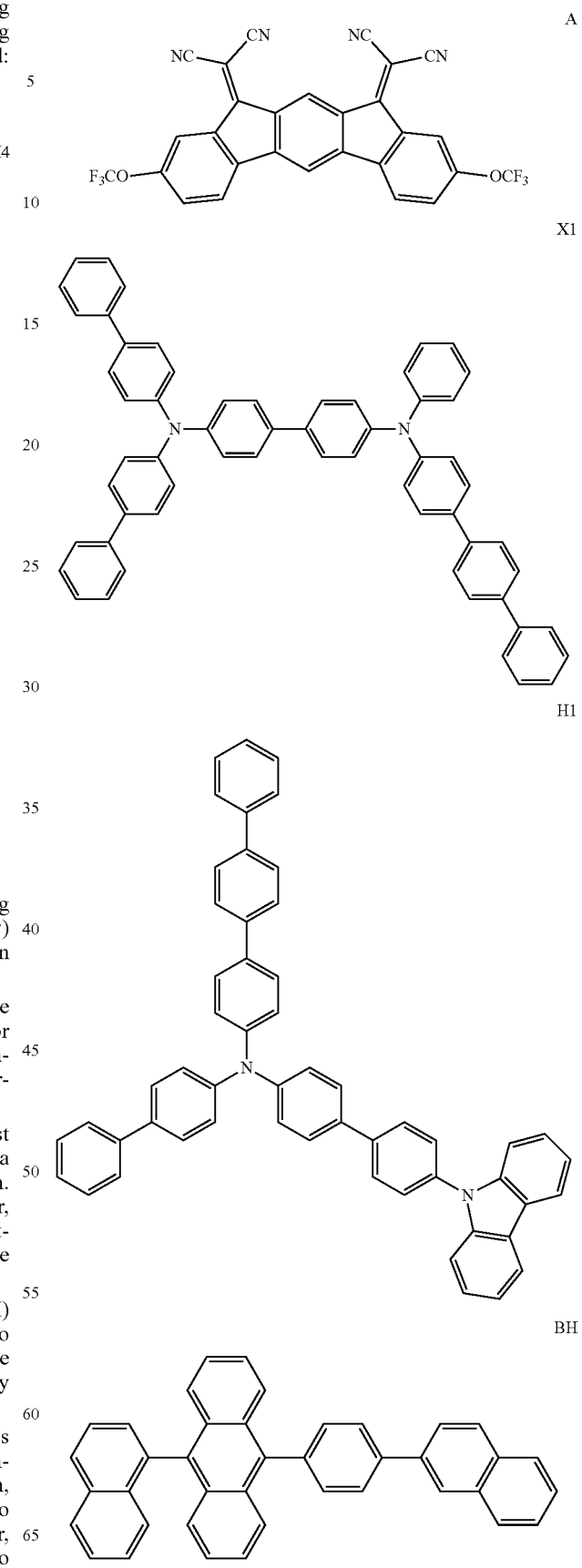

A

X1

H1

BH

BD

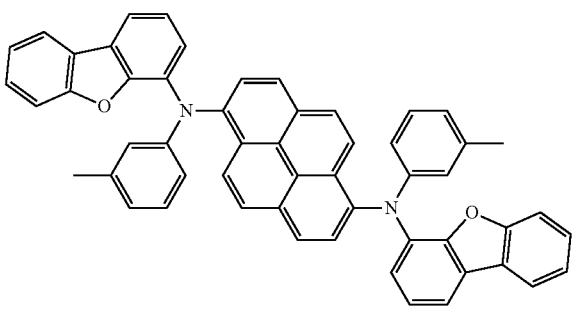

ET1

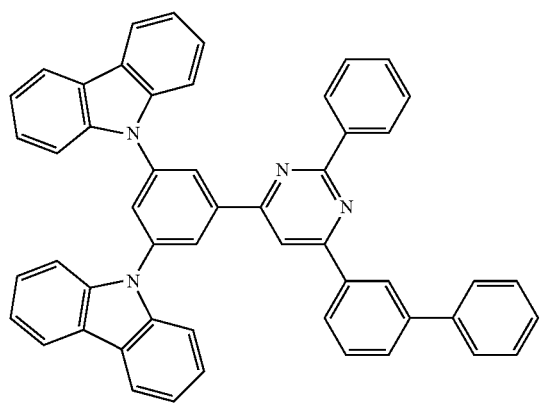

ET2

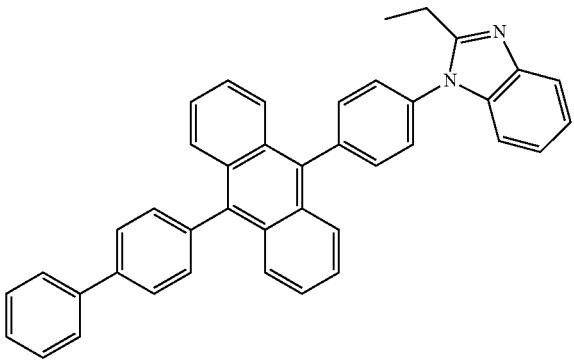

Examples 2 to 4

The organic EL device of each of Examples 2 to 4 was produced in the same manner as in Example 1 except for using each aromatic amine derivative described in Table 1 as the second hole transporting material.

Comparative Example 1

The organic EL device of Comparative Example 1 was produced in the same manner as in Example 1 except for using the comparative compound 1 as the second hole transporting material.

Comparative Compound 1

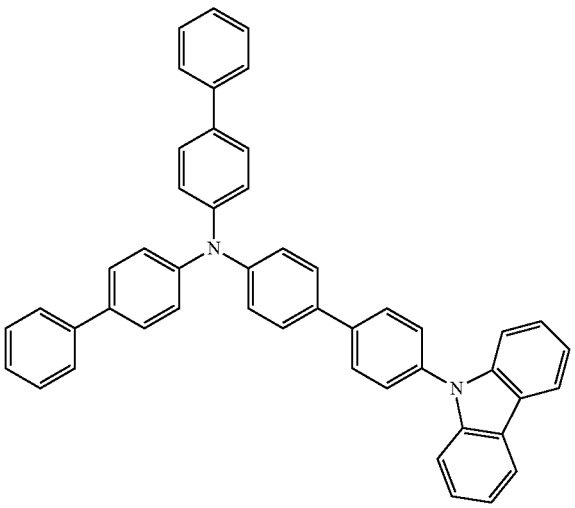

Evaluation of Emission Performance of Organic EL Device

Each of the organic EL devices thus produced was allowed to emit light by operating at direct current to measure the luminance (L) and the current density. Using the measured results, the emission efficiency (cd/A) and the driving voltage (V) at a current density of 10 mA/cm$^2$ were determined. In addition, the 90% lifetime was measured by driving the device at a current density of 50 mA/cm$^2$. The 90% lifetime is the time taken until the luminance is reduced to 90% of the initial luminance when driving the device at a constant current. The results are shown in Table 1.

TABLE 1

| | | | Results | | |
|---|---|---|---|---|---|
| | First hole transporting material | Second hole transporting material | Emission efficiency (cd/A) @10 mA/cm$^2$ | Driving voltage (V) @10 mA/cm$^2$ | 90% Lifetime (h) |
| Examples | | | | | |
| 1 | X1 | H1 | 7.1 | 3.4 | 300 |
| 2 | X1 | H2 | 7.4 | 3.7 | 240 |
| 3 | X1 | H3 | 7.5 | 3.6 | 320 |
| 4 | X1 | H4 | 7.8 | 3.9 | 260 |
| Comparative Example | | | | | |
| 1 | X1 | Comparative compound 1 | 7.0 | 3.6 | 220 |

As seen from Table 1, the aromatic amine derivative of the invention provides organic EL devices which are operated at a low driving voltage and have a high efficiency and a long lifetime.

REFERENCE SIGNS LIST

1: Organic EL device
2: Substrate
3: Anode
4: Cathode
5: Light emitting layer
6: Anode-side organic thin film layer
7: Cathode-side organic thin film layer
10: Emission unit

The invention claimed is:
1. A compound represented by formula (A) or (B):

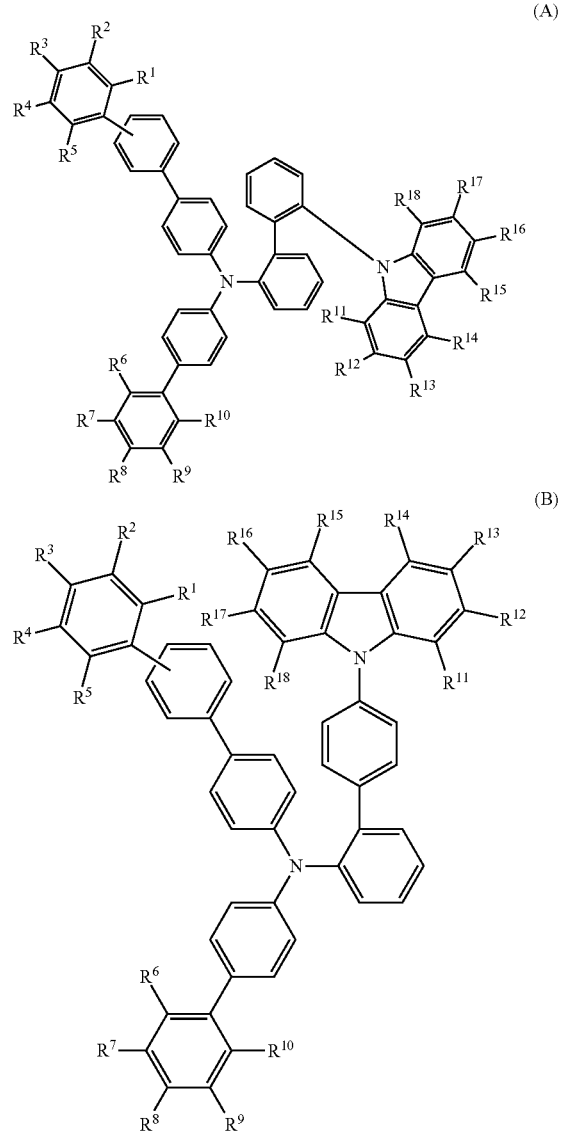

wherein:
each of $R^1$ to $R^5$ is independently a hydrogen atom, a substituted or unsubstituted alkyl group having 1 to 20 carbon atoms, a substituted or unsubstituted aryl group having 6 to 30 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 30 ring carbon atoms, a halogen atom, or a cyano group, and adjacent two selected from $R^1$ to $R^5$ are not bonded to each other thereby failing to form a ring structure;
each of $R^6$ to $R^{10}$ is independently a hydrogen atom, a substituted or unsubstituted alkyl group having 1 to 20 carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 30 ring carbon atoms, a halogen atom, or a cyano group, or adjacent two selected from $R^6$ to $R^{10}$ form a ring structure by being bonded to each other or do not form a ring structure; and
each of $R^{11}$ to $R^{18}$ is independently a hydrogen atom, a substituted or unsubstituted alkyl group having 1 to 20 carbon atoms, a substituted or unsubstituted aryl group having 6 to 30 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 30 ring carbon atoms, a halogen atom, or a cyano group, or adjacent two selected from $R^{11}$ to $R^{18}$ form a ring structure by being bonded to each other or do not form a ring structure.

2. The compound according to claim 1, wherein each of $R^1$ to $R^5$ is independently a hydrogen atom, an alkyl group having 1 to 20 carbon atoms, an aryl group having 6 to 30 ring carbon atoms, a haloalkyl group having 1 to 20 carbon atoms, or a halogen atom.

3. The compound according to claim 1, wherein each of $R^6$ to $R^{10}$ is independently a hydrogen atom, an alkyl group having 1 to 20 carbon atoms, a haloalkyl group having 1 to 20 carbon atoms, or a halogen atom.

4. The compound according to claim 1, wherein each of $R^{11}$ to $R^{18}$ is independently a hydrogen atom, an alkyl group having 1 to 20 carbon atoms, an aryl group having 6 to 30 ring carbon atoms, a haloalkyl group having 1 to 20 carbon atoms, or a halogen atom.

5. The compound according to claim 1, wherein:
the alkyl group having 1 to 20 carbon atoms of the substituted or unsubstituted alkyl group having 1 to 20 carbon atoms for $R^1$ to $R^5$, $R^6$ to $R^{10}$, and $R^{11}$ to $R^{18}$ is selected from the group consisting of a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups);
the aryl group having 6 to 30 ring carbon atoms of the substituted or unsubstituted aryl group having 6 to 30 ring carbon atoms for $R^1$ to $R^5$ and $R^{11}$ to $R^{18}$ is selected from the group consisting of a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a triphenylenyl group, a phenalenyl group, a fluorenyl group, a pyrenyl group, a chrysenyl group, a benzochrysenyl group, a s-indacenyl group, an as-indacenyl group, a fluoranthenyl group, a pentacenyl group, a picenyl group, and a pentaphenyl group;
the haloalkyl group having 1 to 20 carbon atoms of the substituted or unsubstituted haloalkyl group having 1 to 20 carbon atoms for $R^1$ to $R^5$, $R^6$ to $R^{10}$, and $R^{11}$ to $R^{18}$ is selected from the group consisting of a heptafluoropropyl group (inclusive of isomeric groups), a pentafluoroethyl group, a 2,2,2-trifluoroethyl group, and a trifluoromethyl group;

the alkoxy group having 1 to 20 carbon atoms of the substituted or unsubstituted alkoxy group having 1 to 20 carbon atoms for $R^1$ to $R^5$, $R^6$ to $R^{10}$, and $R^{11}$ to $R^{18}$ is selected from the group consisting of a t-butoxy group, a propoxy group (inclusive of isomeric groups), an ethoxy group, and a methoxy group;

the haloalkoxy group having 1 to 20 carbon atoms of the substituted or unsubstituted haloalkoxy group having 1 to 20 carbon atoms for $R^1$ to $R^5$, $R^6$ to $R^{10}$, and $R^{11}$ to $R^{18}$ is selected from the group consisting of a heptafluoropropoxy group (inclusive of isomeric groups), a pentafluoroethoxy group, a 2,2,2-trifluoroethoxy group, and a trifluoromethoxy group;

the aryl group in the aryloxy group having 6 to 30 ring carbon atoms of the substituted or unsubstituted aryloxy group having 6 to 30 ring carbon atoms for $R^1$ to $R^5$, $R^6$ to $R^{10}$, and $R^{11}$ to $R^{18}$ is selected from the group consisting of a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a triphenylenyl group, a phenalenyl group, a fluorenyl group, a pyrenyl group, a chrysenyl group, a benzochrysenyl group, a s-indacenyl group, an as-indacenyl group, a fluoranthenyl group, a pentacenyl group, a picenyl group, and a pentaphenyl group; and the halogen atom for $R^1$ to $R^5$, $R^6$ to $R^{10}$, and $R^{11}$ to $R^{18}$ is selected from the group consisting of a fluorine atom, a chlorine atom, a bromine atom, and an iodine atom.

6. The compound according to claim 1, wherein an optional substituent referred to by "substituted or unsubstituted" is at least one selected from the group consisting of an alkyl group having 1 to 20 carbon atoms, an aryl group having 6 to 30 ring carbon atoms, a haloalkyl group having 1 to 20 carbon atoms, an alkoxy group having 1 to 20 carbon atoms, a haloalkoxy group having 1 to 20 carbon atoms, an aryloxy group having 6 to 30 ring carbon atoms, a halogen atom, and a cyano group.

7. The compound according to claim 1, wherein each of $R^1$ to $R^5$, $R^6$ to $R^{10}$, and $R^{11}$ to $R^{18}$ is a hydrogen atom.

8. The compound according to claim 1, wherein adjacent two selected from $R^6$ to $R^{10}$ do not form a ring structure.

9. The compound according to claim 1, wherein adjacent two selected from $R^{11}$ to $R^{18}$ do not form a ring structure.

10. A material for organic electroluminescence devices, the material comprising the compound according to claim 1.

11. An organic electroluminescence device, comprising a cathode, an anode, and an organic thin film layer between the cathode and the anode, wherein the organic thin film layer comprises one or more layers, the organic thin film layer comprises a light emitting layer, and at least one layer of the organic thin film layer comprises the compound according to claim 1.

12. The organic electroluminescence device according to claim 11, wherein the thin film layer comprises a hole injecting layer, a hole transporting layer, or both, and the hole injecting layer, the hole transporting layer, or both comprise the compound.

13. The organic electroluminescence device according to claim 11, wherein the light emitting layer comprises a phosphorescent dopant.

14. The organic electroluminescence device according to claim 11, wherein the light emitting layer comprises a fluorescent dopant.

15. An electronic device, comprising the organic electroluminescence device according to claim 11.

16. The compound according to claim 1, the compound being selected from the following compounds:

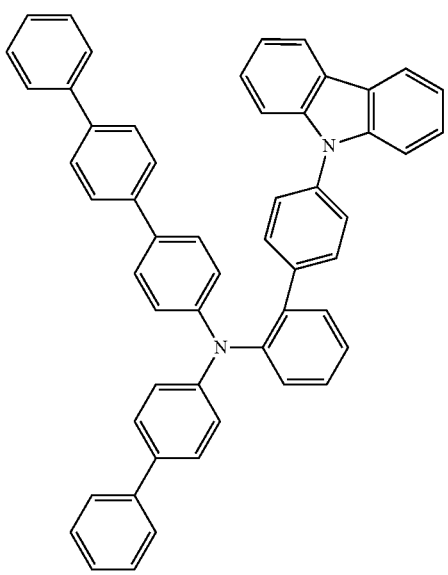

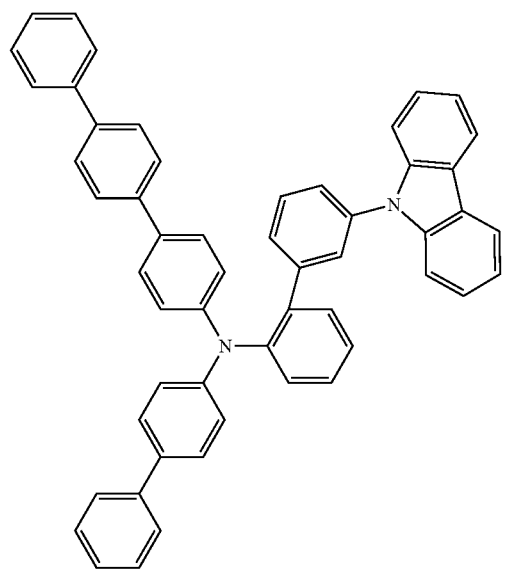

143
-continued
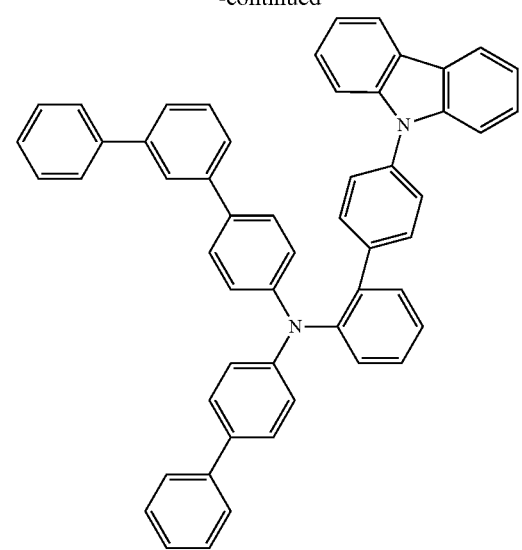
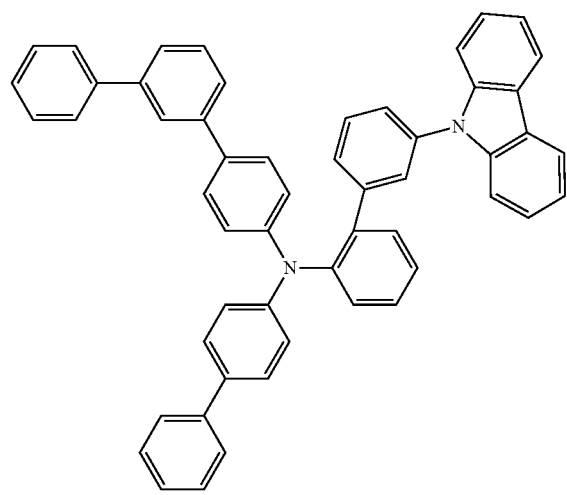
144
-continued
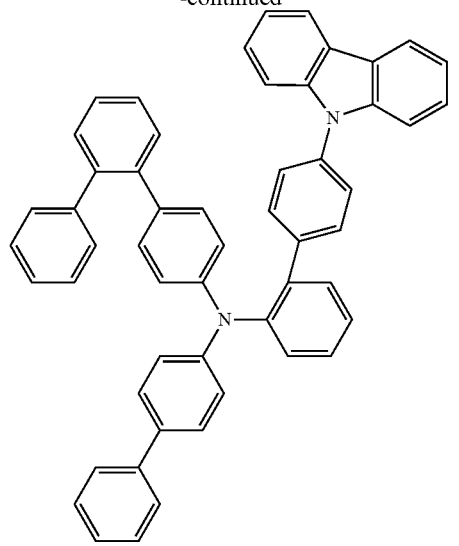
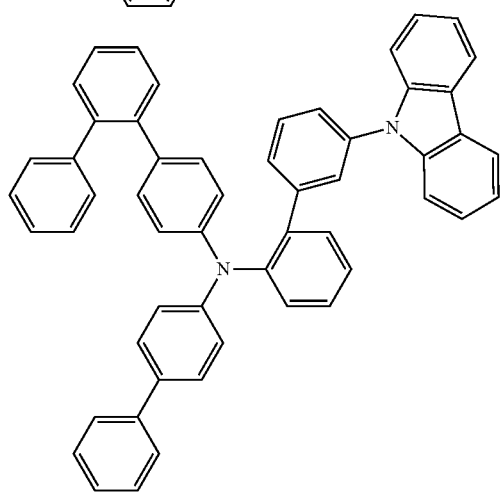
* * * * *